(12) United States Patent
Lu et al.

(10) Patent No.: US 10,941,203 B2
(45) Date of Patent: Mar. 9, 2021

(54) ANTI-TRKB AGONIST ANTIBODIES BINDING TO D5 DOMAIN OF TRKB AND METHODS OF PROMOTING NEURONAL SURVIVAL IN MOTOR NEURON INJURY, STROKE OR GLAUCOMA

(71) Applicant: TSINGHUA UNIVERSITY, Beijing (CN)

(72) Inventors: Bai Lu, Beijing (CN); Wei Guo, Beijing (CN); Hongyang Yao, Beijing (CN)

( * ) Notice: Subject to any disclaimer, the term of this patent is extended or adjusted under 35 U.S.C. 154(b) by 0 days.

(21) Appl. No.: 16/492,954

(22) PCT Filed: Mar. 15, 2018

(86) PCT No.: PCT/CN2018/079109
§ 371 (c)(1),
(2) Date: Sep. 11, 2019

(87) PCT Pub. No.: WO2018/166495
PCT Pub. Date: Sep. 20, 2018

(65) Prior Publication Data
US 2020/0017590 A1    Jan. 16, 2020

(30) Foreign Application Priority Data
Mar. 15, 2017 (WO) ............... PCT/CN2017/076728

(51) Int. Cl.
*A61K 39/395* (2006.01)
*A61K 39/00* (2006.01)
(Continued)

(52) U.S. Cl.
CPC ........ *C07K 16/2863* (2013.01); *A61K 38/185* (2013.01); *A61P 9/10* (2018.01); *A61P 25/00* (2018.01); *A61P 25/02* (2018.01); *A61P 25/28* (2018.01); *A61P 27/00* (2018.01); *A61P 27/02* (2018.01); *A61P 27/06* (2018.01); *C07K 14/48* (2013.01); *C07K 16/00* (2013.01); *C07K 16/2878* (2013.01); *A61K 9/0048* (2013.01); *A61K 38/177* (2013.01); *A61K 38/1709* (2013.01); *A61K 38/18* (2013.01); *A61K 39/395* (2013.01); *A61K 2039/505* (2013.01); *A61K 2039/507* (2013.01); *A61L 27/383* (2013.01); *A61L 2300/414* (2013.01); *A61P 21/00* (2018.01); *A61P 25/14* (2018.01); *A61P 25/16* (2018.01); *C07K 14/47* (2013.01); *C07K 14/705* (2013.01); *C07K 14/70503* (2013.01); *C07K 14/70578* (2013.01); *C07K 16/18* (2013.01); *C07K 16/28* (2013.01); *C07K 2317/21* (2013.01); *C07K 2317/24* (2013.01); *C07K 2317/30* (2013.01); *C07K 2317/35* (2013.01); *C07K 2317/50* (2013.01); *C07K 2317/51* (2013.01); *C07K 2317/515* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/62* (2013.01); *C07K 2317/622* (2013.01); *C07K 2317/624* (2013.01); *C07K 2317/626* (2013.01);
(Continued)

(58) Field of Classification Search
CPC .......... A61K 2039/505; A61K 39/3955; A61K 38/185; A61K 47/6849; A61K 47/6851; A61K 38/00; A61K 39/39591; A61K 9/0046; C07K 16/2863; C07K 2317/34; C07K 2317/75; C07K 2317/21; C07K 2317/565; C07K 2317/55; C07K 2317/92; C07K 16/32; C07K 2317/33; C07K 2317/622; C07K 16/2878; C07K 16/28; C07K 16/286; C07K 2317/24; C07K 2317/71; C07K 2317/94; A61P 25/00; A61P 25/28; A61P 35/00; A61P 27/02; A61P 3/00; A61P 43/00; G01N 2333/475; G01N 33/566
See application file for complete search history.

(56) References Cited

U.S. PATENT DOCUMENTS

RE30,985 E     6/1982   Pye
4,560,655 A   12/1985   Baker
(Continued)

FOREIGN PATENT DOCUMENTS

EP     0125023 A1   11/1984
EP     0183070 A2    6/1986
(Continued)

OTHER PUBLICATIONS

Falkenburger et al., J. Neural. Transm, 2006; 70:261-268.*
(Continued)

*Primary Examiner* — Chang-Yu Wang
(74) *Attorney, Agent, or Firm* — Jun He Law Offices P.C.; James J. Zhu

(57) ABSTRACT

Provided is an isolated TrkB agonist antibody that binds to an epitope contained in one of the extracellular domains of TrkB and is capable of activating TrkB, wherein the extracellular domains comprises extracellular D1, D2, D3, D4, D5 domains and juxtamembrane domain of TrkB. Methods of using the TrkB agonist antibody in treating or reducing the risk of a TrkB associated conditions in a subject, wherein said condition is selected from cell differentiation, synaptic development, neural injury repairing and/or neurite branching.

15 Claims, 18 Drawing Sheets
Specification includes a Sequence Listing.

(51) Int. Cl.

| | | |
|---|---|---|
| C12P 21/08 | (2006.01) | |
| G01N 33/53 | (2006.01) | |
| A61K 49/00 | (2006.01) | |
| A61K 49/16 | (2006.01) | |
| C07K 14/00 | (2006.01) | |
| A61K 38/00 | (2006.01) | |
| C07K 16/28 | (2006.01) | |
| A61P 25/28 | (2006.01) | |
| A61K 38/18 | (2006.01) | |
| A61P 25/00 | (2006.01) | |
| A61P 25/02 | (2006.01) | |
| A61P 27/00 | (2006.01) | |
| A61P 27/06 | (2006.01) | |
| A61P 27/02 | (2006.01) | |
| C07K 16/00 | (2006.01) | |
| C07K 14/48 | (2006.01) | |
| A61P 9/10 | (2006.01) | |
| C07K 16/18 | (2006.01) | |
| A61P 25/14 | (2006.01) | |
| A61K 9/00 | (2006.01) | |
| A61K 38/17 | (2006.01) | |
| C07K 14/705 | (2006.01) | |
| C07K 14/47 | (2006.01) | |
| A61P 25/16 | (2006.01) | |
| C12N 5/0793 | (2010.01) | |
| A61P 21/00 | (2006.01) | |
| A61L 27/38 | (2006.01) | |

(52) U.S. Cl.
CPC ...... *C07K 2317/75* (2013.01); *C07K 2317/92* (2013.01); *C07K 2319/00* (2013.01); *C07K 2319/31* (2013.01); *C12N 5/0619* (2013.01); *C12Y 207/10001* (2013.01); *G01N 2333/46* (2013.01); *G01N 2333/70575* (2013.01); *G01N 2500/10* (2013.01)

(56) References Cited

U.S. PATENT DOCUMENTS

| | | | |
|---|---|---|---|
| 4,657,760 A | 4/1987 | Kung et al. | |
| 4,657,866 A | 4/1987 | Kumar | |
| 4,767,704 A | 8/1988 | Cleveland et al. | |
| 4,816,397 A | 3/1989 | Boss et al. | |
| 4,816,567 A | 3/1989 | Cabilly et al. | |
| 4,927,762 A | 5/1990 | Darfler | |
| 5,122,469 A | 6/1992 | Mather et al. | |
| 5,206,344 A | 4/1993 | Katre et al. | |
| 5,225,212 A | 7/1993 | Martin et al. | |
| 5,225,539 A | 7/1993 | Winter | |
| 5,530,101 A | 6/1996 | Queen et al. | |
| 5,807,715 A | 9/1998 | Morrison et al. | |
| 5,859,205 A | 1/1999 | Adair et al. | |
| 6,005,079 A | 12/1999 | Casterman et al. | |
| 6,407,213 B1 | 6/2002 | Carter et al. | |
| 6,881,557 B2 | 4/2005 | Foote | |
| 7,244,592 B2 | 7/2007 | Hoogenboom et al. | |
| 7,384,632 B2* | 6/2008 | Devaux | C07K 16/32 424/142.1 |
| 7,615,383 B2* | 11/2009 | Devaux | A61P 21/00 436/547 |
| 9,200,080 B2* | 12/2015 | Saragovi | A61P 25/28 |
| 9,914,781 B1* | 3/2018 | Bhinder | C07K 16/2863 |
| 2004/0137513 A1* | 7/2004 | Devaux | A61P 25/02 435/7.1 |
| 2007/0036794 A1* | 2/2007 | Devaux | A61P 25/28 424/146.1 |
| 2010/0003261 A1* | 1/2010 | Devaux | A61P 21/00 424/141.1 |
| 2010/0196390 A1 | 8/2010 | Lin et al. | |
| 2012/0045443 A1* | 2/2012 | Devaux | A61P 9/00 424/143.1 |
| 2017/0029511 A1* | 2/2017 | Saragovi | A61K 39/39591 |
| 2018/0000950 A1* | 1/2018 | Savel | A61K 47/44 |
| 2020/0017590 A1* | 1/2020 | Lu | A61P 3/00 |

FOREIGN PATENT DOCUMENTS

| | | |
|---|---|---|
| EP | 0239400 A2 | 9/1987 |
| EP | 0244234 A2 | 11/1987 |
| EP | 0402226 A1 | 12/1990 |
| EP | 0404097 A2 | 12/1990 |
| WO | 8700195 A1 | 1/1987 |
| WO | 9003430 A1 | 4/1990 |
| WO | 9007861 A1 | 7/1990 |
| WO | 9311161 A1 | 6/1993 |
| WO | 9404678 A1 | 3/1994 |
| WO | 9425591 A1 | 11/1994 |
| WO | 9602576 A1 | 2/1996 |
| WO | 2006133164 A2 | 12/2006 |
| WO | 2011/103667 A1 | 9/2011 |
| WO | 2017192538 A1 | 11/2017 |

OTHER PUBLICATIONS

Tayebati, Mech. Ageing Dev. 2006. 127: 100-8.*
Sarter, Neurosci. and Biobehav. Rev. 2004. 28: 645-650.*
Swerdlow, Clin. Interv. Ageing 2007; 2:347-359.*
Atwood et al., J. Alzheimer's Disease; 2015; 47:33-47.*
Henstridge et al., Nat. Rev. Neurosci. 2019; 20: 94-107.*
Anger. Neurotoxicology 1991. 12: 403-13.*
Moore et al., Annu. Rev. Neurosci. 2005; 28:57-87.*
Jagmag et al., Front. Neurosci. 2016; 9:503. Doi:10.3389/fnins.2015.00503.*
Potashikin et al., Parkinson's Disease, 2011; 658083; doi:104061/2011/658083.*
Rudikoff et al.,Proc. Natl. Acad. Sci. USA 1982 vol. 79: p. 1979.*
Kandratavicius et al.. Neurospyschia. Dis. & Treatment; 2014; 10:1693-105.*
French, Epilepsy Curr. 2006; 6:177-180.*
Kwan et al., Epilepsia; 2009; 50:57-62.*
Kang et al., Austin J. Cerebrovasc.Dis. Stroke. 2014; 1: 1-11.*
The fact sheet of refractory seizure or epilepsy (retrieved from the web site of Johns Hopkins Medicine: www.hopkinsmedicine.org/health/conditions-and-diseases/epilepsy/refractory-epilepsy on Mar. 29, 2018.*
MacCallum et al.,J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al.,J. Mol. Biol. 2002; 320: 415-428.*
Holm et al., Mol. Immunol., 2007; 44: 1075-1084.*
Chen et al.,J. Mol. Bio., 1999; 293: 865-881.*
Wu et al., J. Mol. Biol., 1999; 294:151-162.*
Bowie et al. Science, 1990, 247:1306-1310.*
Burgess et al. J of Cell Bio. 111:2129-2138, 1990.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Haider et al. Cureus, 2017; 9:e1028.DOI 10.7759/cureus.1028.*
Chen et al. Animal Models of Acute Neurological INjury 2nd Edition, Springer Nature Switzerland AG2009, 2019.*
Van Damme et al. Disease Models & Mechanisms 2017; 10:537-549. doi:10.1242/dmm.029058.*
Stephenson et al. Drug Discovery Today: Disease Models: Models of Neuroimmune and Neurodegenerative Diseases, 2017, 25-26. doi.org/10.1016/j.ddmod.2018.10.001.*
Guo et al. Neurobiol. Dis. 2019; 132:104590. doi.org/10.1016/j.nbd.2019.104590.*
Pradhan et al. Front. Cell. Neurosci. 2019, doi.10.3389/fncel.2019.00368.*
Morrice et al. Neural Reg. Res. 2018. doi:10.4103/1673-5374.241445.*

(56) References Cited

OTHER PUBLICATIONS

Leske, M. C. et al., "Early manifest glaucoma trial", Ophthalmology (Nov. 1999), vol. 106(11), pp. 2144-2153.
Johnson, E. C. et al., "Chronology of optic nerve head and retinal responses to elevated intraocular pressure", Investigative Ophthalmology and Visual Science (Feb. 2000), vol. 41(2), pp. 431-442.
Quigley, H. A. et al., "Retrograde axonal transport of BDNF in retinal ganglion cells is blocked by acute IOP elevation in rats", Investigative ophthalmology & visual science (Oct. 2000), vol. 41(11), pp. 3460-3466.
Pease, M. E. et al., "Obstructed axonal transport of BDNF and its receptor TrkB in experimental glaucoma", Investigative ophthalmology & visual science (Mar. 2000), vol. 41(3), pp. 764-774.
Guo, Y. et al., "Does elevated intraocular pressure reduce retinal TRKB-mediated survival signaling in experimental glaucoma?", Experimental Eye Research (2009), vol. 89, pp. 921-933.
Shi, Y. et al., "Continuous hidden process model for time series expression experiments", Bioinformatics (2007), vol. 23, pp. i459-i467.
Sposato, V. et al., "Reduced NGF level and TrkA protein and TrkA gene expression in the optic nerve of rats with experimentally induced glaucoma", Neuroscience Letters (2008), vol. 446, pp. 20-24.
Iwabe, S. et al., "Retrograde axonal transport obstruction of brain-derived neurotrophic factor (BDNF) and its TrkB receptor in the retina and optic nerve of American Cocker Spaniel dogs with spontaneous glaucoma", Veterinary Ophthalmology (2007), vol. 10, Supplement 1, pp. 12-19.
Srinivasan, B. et al., "Microglia-derived pronerve growth factor promotes photoreceptor cell death via p75 neurotrophin receptor", The Journal of Biological Chemistry (Oct. 2004), vol. 279(40), pp. 41839-41845.
Frezzotti, P. et al., "Structural and Functional Brain Changes beyond Visual System in Patients with Advanced Glaucoma", PLoS ONE (Aug. 2014), vol. 9(8), p. e105931, pp. 1-11.
Georgiou, A. L. et al., "Changes in NMDA receptor contribution to synaptic transmission in the brain in a rat model of glaucoma", Neurobiology of Disease (2010), vol. 39, pp. 344-351.
Williams, A. L. et al., "Evidence for widespread structural brain changes in glaucoma: A preliminary voxel-based MRI study", Investigative Ophthalmology and Visual Science (Aug. 2013), vol. 54(8), pp. 5880-5887.
Camu, W. et al., "Purification of embryonic rat motoneurons by panning on a monoclonal antibody to the low-affinity NGF receptor", Journal of Neuroscience Methods (1992), vol. 44, pp. 59-70.
International Search Report of PCT Application No. PCT/CN2018/079109, dated Jun. 20, 2018.
Chao, G. et al., "Isolating and engineering human antibodies using yeast surface display", Nature Protocols (2006), vol. 1(2), pp. 755-768.
Mondon, P. et al., "Human antibody libraries: A race to engineer and explore a larger diversity", Frontiers in Bioscience (2008), vol. 13, p. 1117-1129.
Graham, F. L. et al., "Characteristics of a Human Cell Line Transformed by DNA from Human Adenovirus Type 5", Journal of General Virology (1977), vol. 36, pp. 59-72.
Urlaub, G. et al., "Isolation of Chinese hamster cell mutants deficient in dihydrofolate reductase activity", Proceedings of the National Academy of Sciences of the United States of America (1980), vol. 77(7), pp. 4216-4220.
Mather, J. P. et al., "Establishment and Characterization of Two Distinct Mouse Testicular Epithelial Cell Lines", Biology of Reproduction (1980), vol. 23, pp. 243-252.
Mather, J. P. et al., "Culture of Testicular Cells in Hormone-Supplemented Serum-Free Medium", Annals New York Academy of Sciences (1982), vol. 383, pp. 44-68.
Ham, R. G. et al., "[5] Media and growth requirements", Methods in Enzymology (1979), vol. LVIII, pp. 44-93.
Barnes, D. et al., "Methods for growth of cultured cells in serum-free medium", Analytical Biochemistry (1980), vol. 102, pp. 255-270.
Carter, P. et al., "High Level *Escherichia coli* Expression and Production of a Bivalent Humanized Antibody Fragment", Nature Biotechnology (Feb. 1992), vol. 10, pp. 163-167.
Lindmark, R. et al., "Binding of immunoglobulins to protein A and immunoglobulin levels in mammalian sera", Journal of Immunological Methods (1983), vol. 62, pp. 1-13.
Guss, B. et al., "Structure of the IgG-binding regions of streptococcal protein G", The EMBO Journal (1986), vol. 5(7), pp. 1567-1575.
Langer, R. et al., "Polymer-controlled drug delivery systems", Accounts of Chemical Research (1993), vol. 26, pp. 537-542.
Karran, E. et al., "A critique of the drug discovery and phase 3 clinical programs targeting the amyloid hypothesis for Alzheimer disease", Annals of Neurology (Aug. 2014), vol. 76(2), pp. 185-205.
Mullard, A. et al., "Sting of Alzheimer's failures offset by upcoming prevention trials", Nature Reviews Drug Discovery (Sep. 2012), vol. 11, pp. 657-660.
Lu, B. et al., "BDNF-based synaptic repair as a disease-modifying strategy for neurodegenerative diseases", Nature Reviews Neuroscience (2013), vol. 14, pp. 1-16.
Sheng, Z.-H. et al., "Mitochondrial transport in neurons: impact on synaptic homeostasis and neurodegeneration", Nature Reviews Neuroscience (2012), vol. 13(2), pp. 77-93.
Chao, M. V. et al., "Neurotrophin survival signaling mechanisms", Journal of Alzheimer's Disease(2004), vol. 6, pp. S7-S11.
Poo, M. ming et al., "Neurotrophins as synaptic modulators", Nature Reviews Neuroscience (2001), vol. 2, pp. 24-32.
Egan, M. F. et al., "The BDNF val66met Polymorphism Affects Activity-Dependent Secretion of BDNF and Human Memory and Hippocampal Function", Cell (Jan. 2003), vol. 112, pp. 257-269.
Dennis, N. A. et al., "Brain-derived neurotrophic factor val66met polymorphism and hippocampal activation during episodic encoding and retrieval tasks", Hippocampus (2011), vol. 21(9), pp. 980-989.
Sanchez, M. M. et al., "BDNF polymorphism predicts the rate of decline in skilled task performance and hippocampal volume in healthy individuals", Translational Psychiatry (2011), vol. 1, p.e51, pp. 1-8.
Voineskos, A. N. et al., "The Brain-Derived Neurotrophic Factor Val66Met Polymorphism and Prediction of Neural Risk for Alzheimer Disease", Archives of General Psychiatry (Feb. 2011), vol. 68(2), p. 198-206.
Yang, X. et al., "Impact of Brain-Derived Neurotrophic Factor Val66Met Polymorphism on Cortical Thickness and Voxel-Based Morphometry in Healthy Chinese Young Adults", PLoS ONE (Jun. 2012), vol. 7(6), p. e37777, pp. 1-8.
Nagappan, G. et al., "Control of extracellular cleavage of ProBDNF by high frequency neuronal activity", Proceedings of the National Academy of Sciences (Jan. 2009), vol. 106(4), pp. 1267-1272.
Nagahara, A. H. et al., "Potential therapeutic uses of BDNF in neurological and psychiatric disorders", Nature Reviews Drug Discovery (Mar. 2011), vol. 10, pp. 209-219.
Wijesekera, L. C. et al., "Amyotrophic lateral sclerosis", Orphanet Journal of Rare Diseases (2009), vol. 4, pp. 1-22.
Boillée, S. et al., "ALS: A Disease of Motor Neurons and Their Nonneuronal Neighbors", Neuron (Oct. 2006), vol. 52, pp. 39-59.
Mitchell, J. et al., "Amyotrophic lateral sclerosis", The Lancet (Jun. 2007), vol. 369, pp. 2031-2041.
Rosen, D. R. et al., "Mutations in Cu/Zn superoxide dismutase gene are associated with familial amyotrophic lateral sclerosis", Nature (1993), vol. 364, pp. 362-362.
Couthouis, J. et al., "A yeast functional screen predicts new candidate ALS disease genes", PNAS (Dec. 2011), vol. 108(52), pp. 20881-20890.
Carlesi, C. et al., "Strategies for clinical approach to neurodegeneration in amyotrophic lateral sclerosis", Archives Italiennes de Biologie (2011), vol. 149, pp. 151-167.
Miller, R. G. et al., "Riluzole for amyotrophic lateral sclerosis (ALS)/motor neuron disease (MND)", The Cochrane Collaboration (2007), Issue 1, pp. 1-29.

(56) References Cited

OTHER PUBLICATIONS

Mutoh, T. et al., "Decreased phosphorylation levels of TrkB neurotrophin receptor in the spinal cords from patients with amyotrophic lateral sclerosis", Neurochemical Research (2000), vol. 25(2), pp. 239-245.
Küst, B. M. et al., "Elevated Levels of Neurotrophins in Human Biceps Brachii Tissue of Amyotrophic Lateral Sclerosis", Experimental Neurology (2002), vol. 177, pp. 419-427.
Kwiatkowski, T. J. et al., "Mutations in the FUS/TLS Gene on Chromosome 16 Cause Familial Amyotrophic Lateral Sclerosis", Science (2009), vol. 323, pp. 1205-1208.
Vance, C. et al., "Mutations in FUS, an RNA Processing Protein, Cause Familial Amyotrophic Lateral Sclerosis Type 6", Science (Feb. 2009), vol. 323(5918), pp. 1208-1211.
Lagier-Tourenne, C. et al., "Divergent roles of ALS-linked proteins FUS/TLS and TDP-43 intersect in processing long pre-mRNAs", Nature Neuroscience (2012), doi:10.1038/nn.3230, pp. 1-12.
Qiu, H. et al., "ALS-associated mutation FUS-R521C causes DNA damage and RNA splicing defects", Journal of Clinical Investigation (Mar. 2014), vol. 124(3), pp. 981-999.
Gharami, K. et al., "Brain-derived neurotrophic factor over-expression in the forebrain ameliorates Huntington's disease phenotypes in mice", Journal of Neurochemistry (Apr. 2008), vol. 105(2), pp. 369-379.
Xie, Y. et al., "BDNF Overexpression in the Forebrain Rescues Huntington's Disease Phenotypes in YAC128 Mice", Journal of Neuroscience (Nov. 2010), vol. 30(44), pp. 14708-14718.
Thoenen, H. et al., "Neurotrophins: from enthusiastic expectations through sobering experiences to rational therapeutic approaches", Nature Neuroscience supplement (Nov. 2002), vol. 5, pp. 1046-1050.
Gransee, H. M. et al., "Targeted Delivery of TrkB Receptor to Phrenic Motoneurons Enhances Functional Recovery of Rhythmic Phrenic Activity after Cervical Spinal Hemisection", PLoS ONE (May 2013), vol. 8(5), p. e64755. pp. 1-10.
Kishino, A. et al., "BDNF Prevents and Reverses Adult Rat Motor Neuron Degeneration and Induces Axonal Outgrowth", Experimental Neurology (1997), vol. 144, pp. 273-286.
Mantilla, C. B. et al., "Motoneuron BDNF/TrkB signaling enhances functional recovery after cervical spinal cord injury", Experimental Neurology (Sep. 2013), vol. 247, pp. 101-109.
Ochs, G. et al., "A phase I/II trial of recombinant methionyl human brain derived neurotrophic factor administered by intrathecal infusion to patients with amyotrophic lateral sclerosis", Amyotrophic Lateral Sclerosis and Other Motor Neuron Disorders (Jan. 2000), vol. 1(3), pp. 201-206.
Dittrich, F. et al., "Pharmacokinetics of Intrathecally Applied BDNF and Effects on Spinal Motoneurons", Experimental Neurology (1996), vol. 141, pp. 225-239.
Knusel, B. et al., "Ligand-induced down-regulation of trk messenger RNA, protein and tyrosine phosphorylation in rat cortical neurons", Neuroscience (1997), vol. 78(3), pp. 851-862.
Longo, F. M. et al., "Small-molecule modulation of neurotrophin receptors: a strategy for the treatment of neurological disease", Nature Reviews Drug Discovery (Jul. 2013), vol. 12, pp. 507-525.
Clary, D. O. et al., "TrkA cross-linking mimics neuronal responses to nerve growth factor", Molecular Biology of the Cell (May 1994), vol. 5, pp. 549-563.
Lesauteur, L. et al., "Potent human p140-TrkA agonists derived from an anti-receptor monoclonal antibody", The Journal of Neuroscience (Feb. 1996), vol. 16(4), pp. 1308-1316.
Lu, B. et al., "The yin and yang of neurotrophin action", Nature Reviews Neuroscience (Aug. 2005), vol. 6, pp. 603-614.
Dandona, L. et al., "Revision of visual impairment definitions in the International Statistical Classification of Diseases", BMC Medicine (2006), vol. 4, p. 1-7.
Quigley, H. A., "Number of people with glaucoma worldwide", British Journal of Ophthalmology (1996), vol. 80, pp. 389-393.
Quigley, H. A. et al., "The Number of people with glaucoma worldwide in 2010 and 2020", British Journal of Ophthalmology (2006), vol. 90, pp. 262-267.
Casson, R. J. et al., "Definition of glaucoma: clinical and experimental concepts", Clinical & Experimental Ophthalmology (2012), vol. 40, pp. 341-349.
Barkan, O. et al., "Micro-Surgery in Chronic Simple Glaucoma", California and Western Medicine (Jan. 1938), vol. 48(1), pp. 10-12.
Heijl, A. et al., "Reduction of Intraocular Pressure and Glaucoma Progression", Arch Ophthalmol (2002), vol. 120, pp. 1268-1279.
Al-Lazikani, B. et al., "Standard conformations for the canonical structures of immunoglobulins", Journal of Molecular Biology (1997), vol. 273, pp. 927-948.
Chothia, C. et al., "Domain association in immunoglobulin molecules", Journal of Molecular Biology (1985), vol. 186, pp. 651-663.
Chothia, C. et al., "Canonical structures for the hypervariable regions of immunoglobulins", Journal of Molecular Biology (1987), vol. 196, pp. 901-917.
Chothia, C. et al., "Conformations of immunoglobulin hypervariable regions", Nature (1989), vol. 342, pp. 877-883.
Huston, J. S. et al., "Protein engineering of antibody binding sites: Recovery of specific activity in an anti-digoxin single-chain Fv analogue produced in *Escherichia coli*.", Proceedings of the National Academy of Sciences (1988), vol. 85, pp. 5879-5883.
Riechmann, L. et al., "Single domain antibodies: comparison of camel VH and camelised human VH domains", Journal of Immunological Methods (1999), vol. 231, pp. 25-38.
Muyldermans, S. et al., "Single domain camel antibodies: current status", Reviews in Molecular Biotechnology (2001), vol. 74, pp. 277-302.
Henry, K. A. et al., "Stability-Diversity Tradeoffs Impose Fundamental Constraints on Selection of Synthetic Human VH/VL Single-Domain Antibodies from In Vitro Display Libraries", Frontiers in Immunology (2017), vol. 8, pp. 1-15.
Holliger, P. et al., ""Diabodies": small bivalent and bispecific antibody fragments", Proceedings of the National Academy of Sciences (1993), vol. 90, pp. 6444-6448.
Salmerón, A. et al., "A conformational epitope expressed upon association of CD3-epsilon with either CD3-delta or CD3-gamma is the main target for recognition by anti-CD3 monoclonal antibodies", The Journal of immunology(1991), vol. 147, pp. 3047-3052.
Altschul, S. F. et al., "Basic local alignment search tool", Journal of Molecular Biology (1990), vol. 215, pp. 403-410.
Altschul, S. F. et al., "Gapped BLAST and PSI-BLAST: a new generation of protein database search programs", Nucleic Acids Research (1997), vol. 25(17), pp. 3389-3402.
Higgins, D. G. et al., "[22] Using CLUSTAL for multiple sequence alignments", Methods in Enzymology (1996), vol. 266, pp. 383-402.
Larkin, M. A. et al., "Clustal W and Clustal X version 2.0", Bioinformatics (2007), vol. 23(21), pp. 2947-2948.
Shields, R. L. et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry (2001), vol. 276(9), pp. 6591-6604.
Hempstead, B. L. et al., "Brain-Derived Neurotrophic Factor: Three Ligands, Many Actions", Transactions of the American Clinical and Climatological Association (2015), vol. 126, pp. 9-19.
McAllister, A. K. et al., "Eurotrophins and Synaptic Plasticity", Annual Review of Neuroscience (1999), vol. 22, pp. 295-318.
Nagappan, G. et al., "Activity-dependent modulation of the BDNF receptor TrkB: mechanisms and implications", Trends in Neurosciences (Sep. 2005), vol. 28(9), pp. 464-471.
Huang, E. J. et al., "Neurotrophins: Roles in Neuronal Development and Function", Annual Review of Neuroscience (2001), vol. 24, pp. 677-736.
Kaplan, D. R. et al., "Neurotrophin signal transduction in the nervous system", Current Opinion in Neurobiology (2000), vol. 10, pp. 381-391.
Ibáñez, C. F. et al., "An extended surface of binding to Trk tyrosine kinase receptors in NGF and BDNF allows the engineering of a multifunctional pan-neurotrophin", The EMBO Journal (1993), vol. 12(6), pp. 2281-2293.

(56) References Cited

OTHER PUBLICATIONS

McDonald, N. Q. et al., "New protein fold revealed by a 2.3-Å resolution crystal structure of nerve growth factor", Nature (Dec. 1991), vol. 354, pp. 411-414.

Radziejewski, C. et al., "Dimeric structure and conformational stability of brain-derived neurotrophic factor and neurotrophin-3", Biochemistry (1992), vol. 31, pp. 4431-4436.

Banfield, M. J. et al., "Specificity in Trk Receptor:Neurotrophin Interactions: The Crystal Structure of TrkB-d5 in Complex with Neurotrophin-4/5", Structure (Dec. 2001), vol. 9, pp. 1191-1199.

McCarty, J. H. et al., "Activation loop tyrosines contribute varying roles to TrkB autophosphorylation and signal transduction", Oncogene (1998), vol. 16, pp. 1691-1700.

Easton, J. B. et al., "Brain-derived Neurotrophic Factor Induces Phosphorylation of Fibroblast Growth Factor Receptor Substrate 2", The Journal of Biological Chemistry (Apr. 1999), vol. 274(16), pp. 11321-11327.

Cowley, S. et al., "Activation of MAP kinase kinase is necessary and sufficient for PC12 differentiation and for transformation of NIH 3T3 cells", Cell (Jun. 1994), vol. 77, pp. 841852.

Ballif, B. A. et al., "Molecular mechanisms mediating mammalian mitogen-activated protein kinase (MAPK) kinase (MEK)-MAPK cell survival signals", Cell growth & differentiation (Aug. 2001), vol. 12, pp. 397-408.

Van Weeren, P. C. et al., "Essential Role for Protein Kinase B (PKB) in Insulin-induced Glycogen Synthase Kinase 3 Inactivation", The Journal of Biological Chemistry (May 1998), vol. 273(21), pp. 13150-13156.

Lin, Y.-T. et al., "Up-regulation of dorsal root ganglia BDNF and trkB receptor in inflammatory pain: an in vivo and in vitro study", Journal of Neuroinflammation (2011), vol. 8, p. 126.

Gupta, V. K. et al., "TrkB Receptor Signalling: Implications in Neurodegenerative, Psychiatric and Proliferative Disorders", International Journal of Molecular Sciences (2013), vol. 14, pp. 10122-10142.

Lucidi-Phillipi, C. A. et al., "TrkA Activation Is Sufficient to Rescue Axotomized Cholinergic Neurons", Neuron (Mar. 1996), vol. 16(3), pp. 653-663.

Reichardt, L. F. et al., "Neurotrophin-regulated signalling pathways", Philosophical Transactions of the Royal Society B: Biological Sciences (Sep. 2006), vol. 361, pp. 1545-1564.

Qian, M. D. et al., "Novel Agonist Monoclonal Antibodies Activate TrkB Receptors and Demonstrate Potent Neurotrophic Activities", The Journal of Neuroscience (Sep. 2006), vol. 26(37), pp. 9394-9403.

Hu, Y. et al., "Neurotrophic Effect of a Novel TrkB Agonist on Retinal Ganglion Cells", Investigative Opthalmology & Visual Science (Mar. 2010), vol. 51(3), p. 1747-1754.

Kim, G. S. et al., "TrkB Agonist Antibody Pretreatment Enhances Neuronal Survival and Long-Term Sensory Motor Function Following Hypoxic Ischemic Injury in Neonatal Rats", PLOS ONE (Feb. 2014). Edited by P. Gressens, vol. 9(2), p. e88962, pp. 1-9.

Todd, D. et al., "A Monoclonal Antibody TrkB Receptor Agonist as a Potential Therapeutic for Huntington's Disease", PLOS ONE (Feb. 2014). vol. 9(2), p. e87923, pp. 1-9.

Köhler, G. et al., "Derivation of specific antibody-producing tissue culture and tumor lines by cell fusion", European Journal of Immunology (1976), vol. 6, pp. 511-519.

Neuberger, M. et al., "Generating high-avidity human Mabs in mice", Nature Biotechnology (Jul. 1996), vol. 14, pp. 826.

Lonberg, N. et al., "Transgenic Approaches to Human Monoclonal Antibodies", Handbook of Experimental Pharmacology (1994), vol. 113, pp. 49-101.

Lonberg, N. et al., "Human antibodies from transgenic mice", International Reviews of Immunology(1995), vol. 13, pp. 65-93.

Supplementary Partial European Search Report of European application No. 18766882.7, dated Nov. 13, 2020.

* cited by examiner

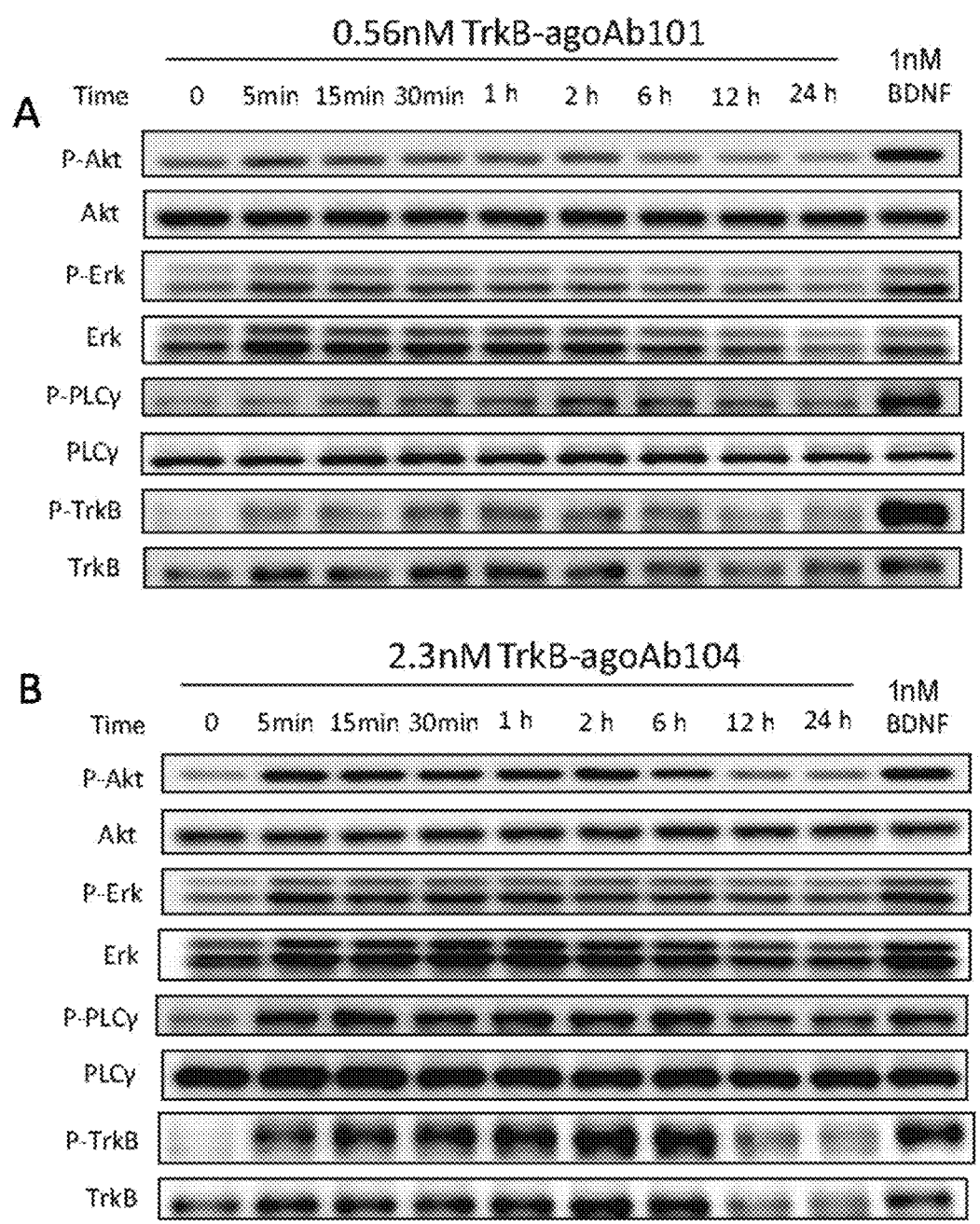
Figure 6A-B

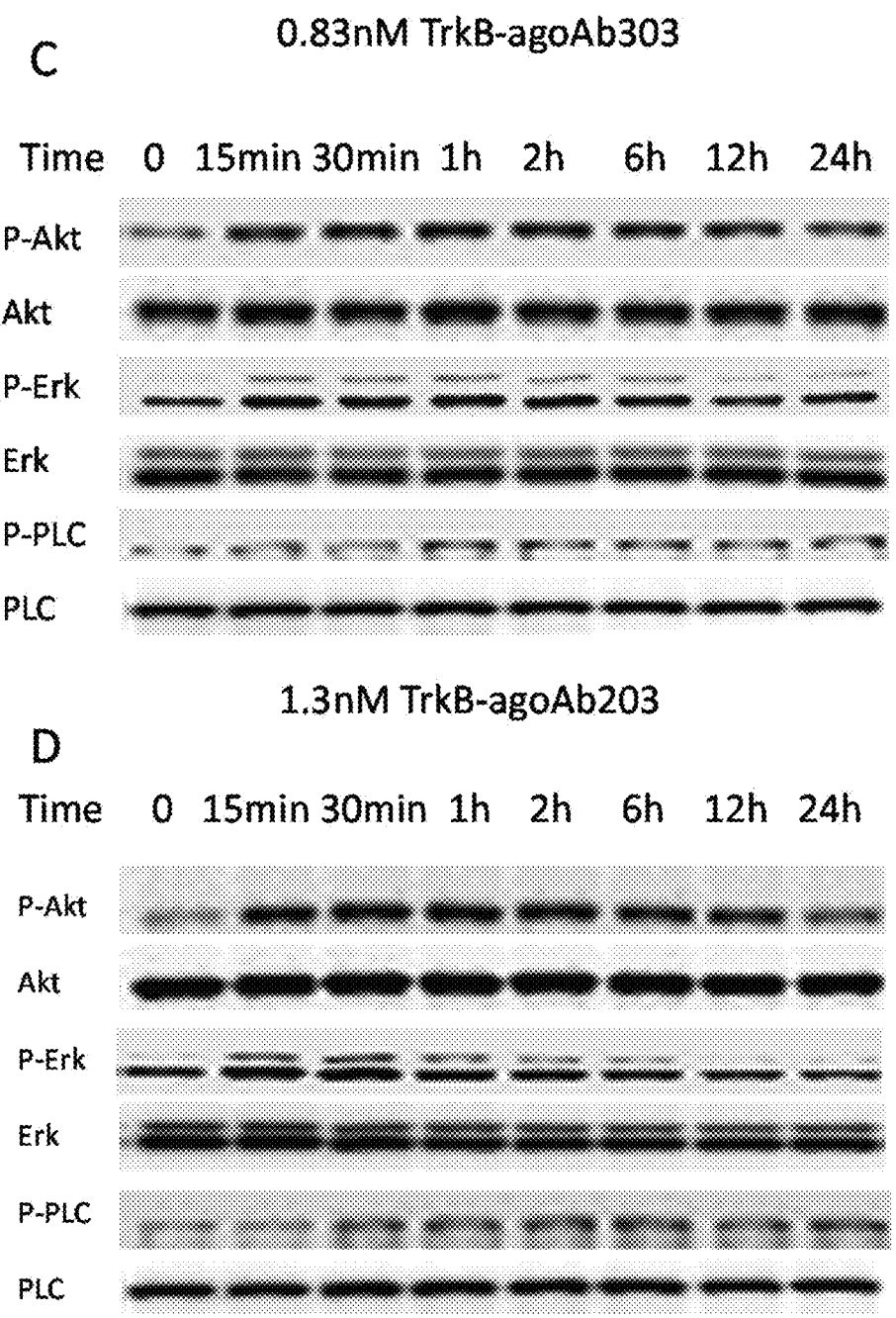
Figure 6C-D

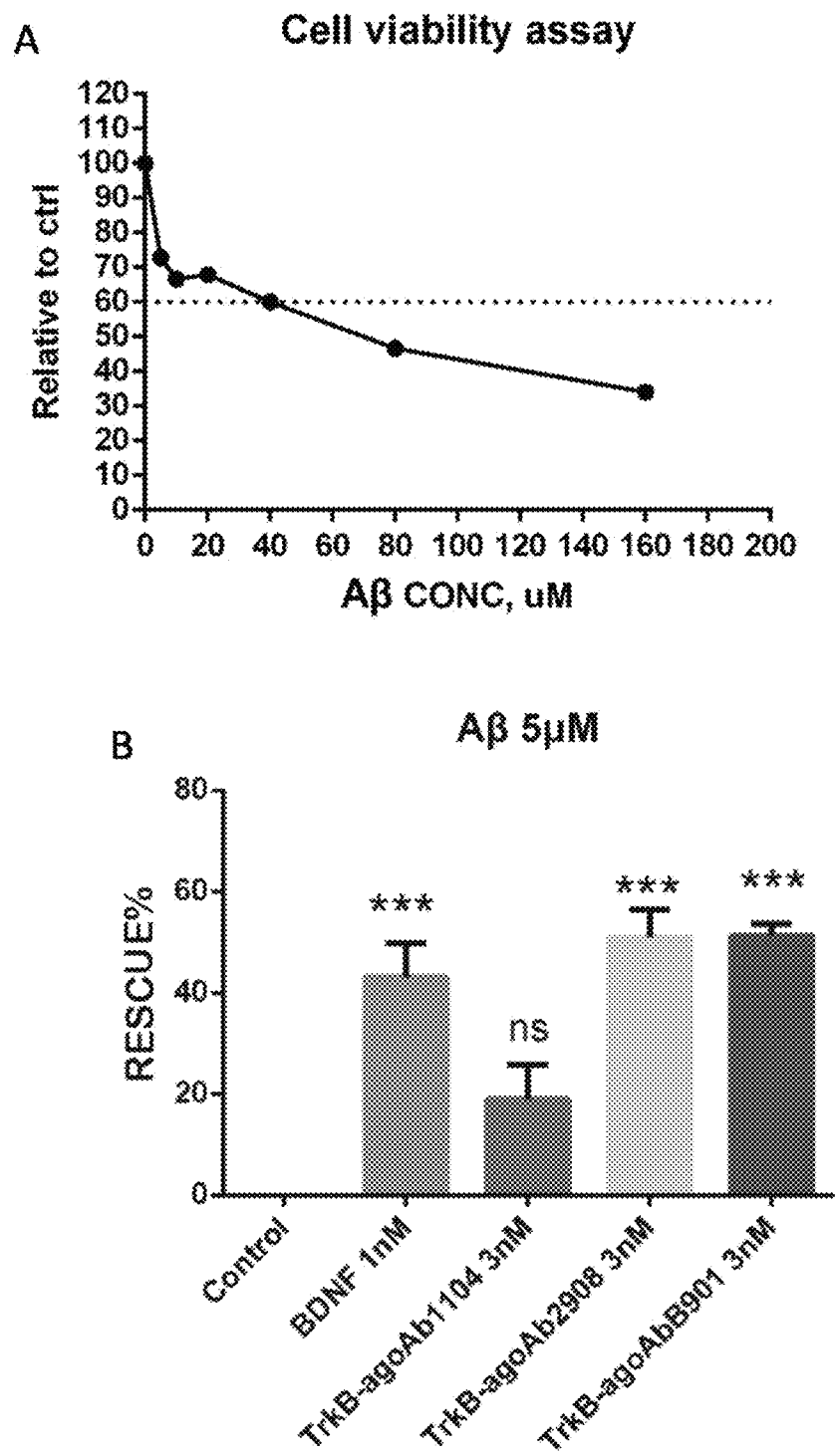
Figure 7A-B

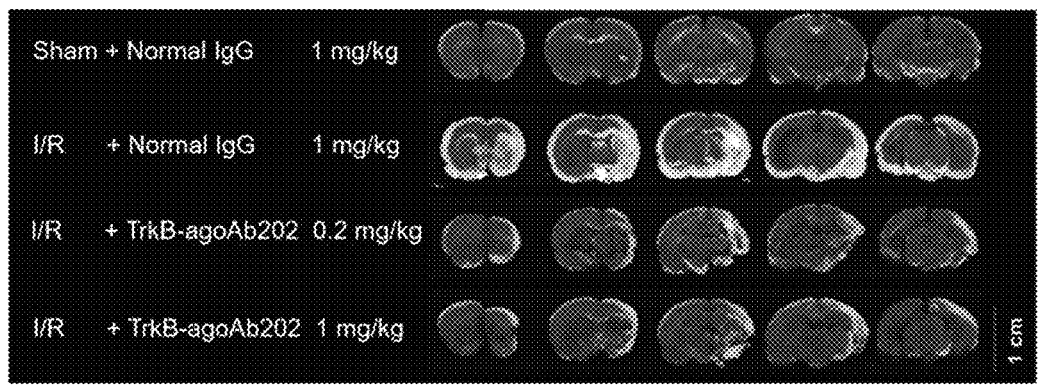
Figure 12
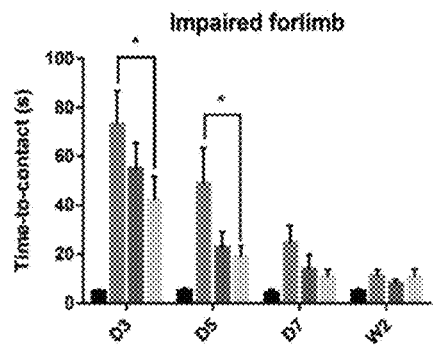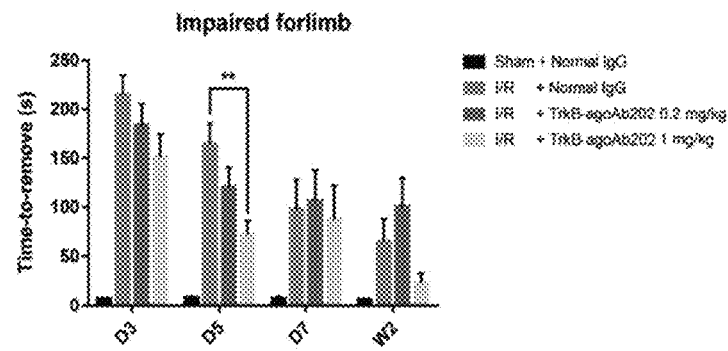
Figure 13

| Sequence ID NO | Description | Amino acid sequences |
|---|---|---|
| 1 | Extracellular domain of human TrkB, residues 32-430 (TrkB ECD) | PTSCKCSASRIWCSDPSPGIVAFPRLEPNS VDPENITEIFIANQKRLEIINEDDVEAYVG LRNLTIVDSGLKFVAHKAFLKNSNLQHIN FTRNKLTSLSRKHFRHLDLSELILVGNPFT CSCDIMWIKTLQEAKSSPDTQDLYCLNES SKNIPLANLQIPNCGLPSANLAAPNLTVEE GKSITLSCSVAGDPVPNMYWDVGNLVSK HMNETSHTQGSLRITNISSDDSGKQISCVA ENLVGEDQDSVNLTVHFAPTITFLESPTSD HHWCIPFTVKGNPKPALQWFYNGAILNE SKYICTKIHVTNHTEYHGCLQLDNPTHM NNGDYTLIAKNEYGKDEKQISAHFMGWP GIDDGANPNYPDVIYEDYGTAANDIGDTT NRSNEIPSTDVTDKTGREH |
| 2 | D1 domain | PTSCKCSA SRIWCSDPSPGIVAFPRLEPNS |
| 3 | D2 domain | GLRNLTIVDSGLKFVAHKAFLKNSNLQHI NFTRNKLTSL SRKHFRH |
| 4 | D3 domain | NPFTCSCDIMWIKTLQEAKSSPDTQDLYC LNES SKNIPLANLQ IPNCGL |
| 5 | D4 domain | PSANLAAPNLTVEEGKSITLSCSVAGDPVP NMYWDVGNLVSKHMNETSHTQGSLRIT NISSDDS GKQISCVAENLVGEDQDSVNLT |
| 6 | D5 domain | TSDHHWCIPFTVKGNPKPALQWFYNGAI LNESKYICTKIHVTNHTEYHGCLQLDNPT HMNNGDYTLIAKN |
| 7 | Juxta-membrane domain | EYGKDEKQISAHFMGWPGIDDGANPNYP DVIYEDYGTAANDIGDTTNRSNEIPSTDV TDKTGREH |
| 8 | Truncated TrkB (TrkB-Δ5 AA: 366-822) | EYGKDEKQISAHFMGWPGIDDGANPNYP DVIYEDYGTAANDIGDTTNRSNEIPSTDV TDKTGREHLSVYAVVVIASVVGFCLLVM LFLLKLARHSKFGMKGPASVISNDDDSAS PLHHISNGSNTPSSSEGGPDAVIIGMTKIP VIENPQYFGITNSQLKPDTFVQHIKRHNIV LKRELGEGAFGKVFLAECYNLCPEQDKIL VAVKTLKDASDNARKDFHREAELLTNLQ HEHIVKFYGVCVEGDPLIMVFEYMKHGD LNKFLRAHGPDAVLMAEGNPPTELTQSQ MLHIAQQIAAGMVYLASQHFVHRDLATR NCLVGENLLVKIGDFGMSRDVYSTDYYR VGGHTMLPIRWMPPESIMYRKFTTESDV WSLGVVLWEIFTYGKQPWYQLSNNEVIE |

Figure 16

| | | CITQGRVLQRPRTCPQEVYELMLGCWQREPHMRKNIKGIHTLLQNLAKASPVYLDILG |
|---|---|---|
| 9 | TrkB-agoAb202 VL-CDR1 | QASESIGNGIA |
| 10 | TrkB-agoAb202 VL-CDR2 | YASYLAS |
| 11 | TrkB-agoAb202 VL-CDR3 | QGYYYGTSGDYA |
| 12 | TrkB-agoAb202 VH-CDR1 | RYWMN |
| 13 | TrkB-agoAb202 VH-CDR2 | TISTGDTTSYASWAKG |
| 14 | TrkB-agoAb202 VH-CDR3 | GDYQTASYFNL |
| 15 | TrkB-agoAb303 VL-CDR1 | RSSQNIVHSNGNTYLE |
| 16 | TrkB-agoAb303 VL-CDR2 | NVSNRFS |
| 17 | TrkB-agoAb303 VL-CDR3 | FQGSHFPWT |
| 18 | TrkB-agoAb303 VH-CDR1 | SYTMS |
| 19 | TrkB-agoAb303 VH-CDR2 | TISSGGDYTYFPDSVKG |
| 20 | TrkB-agoAb303 VH-CDR3 | ESGRGDFDY |
| 21 | TrkB-agoAb203 VL-CDR1 | QASESIGSYLA |
| 22 | TrkB-agoAb203 VL-CDR2 | RASTLAS |
| 23 | TrkB-agoAb203 VL-CDR3 | QQGFIGTNVDNT |
| 24 | TrkB-agoAb203 VH-CDR1 | NYWMI |
| 25 | TrkB-agoAb203 VH-CDR2 | SISTLSDNTWYANWVNG |
| 26 | TrkB-agoAb203 VH-CDR3 | GVGGVLGTSGMDP |
| 27 | TrkB-agoAb303 Light variable region (VL) | DVLMTQTPLSLPVSLGDQASISCRSSQNIVHSNGNTYLEWYLQKPGQSPNLLIYNVSNRFSGVPDRFSGSGSGTDFTLKISRVEAEDLGVYYCFQGSHFPWTFGGGTKLEIT |
| 28 | TrkB-agoAb303 | DVKLVESGGGLVKPGGSLKLSCAASGFTF |

Figure 16 (Cont'd)

| | Heavy variable region (VH) | SSYTMSWVRQTPEKRLEWVATISSGGDYTYFPDSVKGRFTMSRDNAKNALYLQMSSLKSEDTAMYYCTRESGRGDFDYWGQGTTLTVSS |
|---|---|---|
| 29 | TrkB-agoAb2908 VL-CDR1 | RASESVDNYGNSLMH |
| 30 | TrkB-agoAb2908 VL-CDR2 | LASNLES |
| 31 | TrkB-agoAb2908 VL-CDR3 | QQNNEDPPWT |
| 32 | TrkB-agoAb2908 VH-CDR1 | SSWMN |
| 33 | TrkB-agoAb2908 VH-CDR2 | RIYPGDGHTNYNGKFKG |
| 34 | TrkB-agoAb2908 VH-CDR3 | SGYGYGFDC |
| 35 | TrkB-agoAb2908 Light variable region (VL) | NIVLTQSPASLAVSLGQRATISCRASESVDNYGNSLMHWYQQKPGQPPKLLIYLASNLESGVPARFSGSGSRTDFTLTIDPVEADDAATYYCQQNNEDPPWTFGGGTKLEIKRADAAPTVSIFPPSSKLGV |
| 36 | TrkB-agoAb2908 Heavy variable region (VH) | QVQLQQSGPELVKPGASVKISCKASGYTFSSSWMNWVKQRPGQGLEWIGRIYPGDGHTNYNGKFKGKATLTADKSSSTAYMQLTSLTSVDSGVYFCARSGYGYGFDCWGQGTTLTVSSAKTTPPSVYPLVPGSLA |
| 37 | TrkB-agoAb1104 VL-CDR1 | RSSENIYSYLA |
| 38 | TrkB-agoAb1104 VL-CDR2 | NAKTLAE |
| 39 | TrkB-agoAb1104 VL-CDR3 | QHHYGPPYT |
| 40 | TrkB-agoAb1104 VH-CDR1 | RYWMQ |
| 41 | TrkB-agoAb1104 VH-CDR2 | AIYPGDGDTRYTQKFKG |
| 42 | TrkB-agoAb1104 VH-CDR3 | SGLGRAWFTY |
| 43 | TrkB-agoAb1104 Light chain variable region (VL) | DIQMTQSPASLSASVGETVTITCRSSENIYSYLAWYQQKQGKSPQLLVYNAKTLAEGVPSRFSGSGSGTQFSLKINSLQPEDFGSYYCQHHYGPPYTFGGGTKLEIK |
| 44 | TrkB-agoAb1104 Heavy variable | QVQLQQSGAELARPGASVKLSCKASGYTFTRYWMQWVKQRPGQGLEWIGAIYPGD |

Figure 16 (Cont'd)

| | region (VH) | GDTRYTQKFKGKATLTADKSSSTAYMQL SSLASEDSAVYYCAGSGLGRAWFTYWGQ GTLVTVSA |
|---|---|---|
| 45 | TrkB-agoAb901 VL-CDR1 | LASQTIGTLLA |
| 46 | TrkB-agoAb901 VL-CDR2 | AATTLAD |
| 47 | TrkB-agoAb901 VL-CDR3 | QQFYSTPYT |
| 48 | TrkB-agoAb901 VH-CDR1 | RYWMS |
| 49 | TrkB-agoAb901 VH-CDR2 | EINPDGSTINYTPSLKD |
| 50 | TrkB-agoAb901 VH-CDR3 | GNYYGSSLAWFAY |
| 51 | TrkB-agoAb901 Light chain variable region (VL) | DIQMTQSPASQSASLGESVTITCLASQTIG TLLAWYQQKPGKSPQLLIYAATTLADGVP SRFRGSGSGTKFSFKISSLQAEDFVSYYC QQFYSTPYTFGGGTKLEIK |
| 52 | TrkB-agoAb901 Heavy variable region (VH) | EVKLVESGGGLVQPGGSLKLSCAASGFDF SRYWMSWVRQAPGKGLEWIGEINPDGST INYTPSLKDKFIISRDNAKNTLYLQMSKV RSEDTALYYCARGNYYGSSLAWFAYWG QGTLVTVSA |
| 53 | TrkB-agoAb5702 VL-CDR1 | RASKSISKYLA |
| 54 | TrkB-agoAb5702 VL-CDR2 | SGSTLQS |
| 55 | TrkB-agoAb5702 VL-CDR3 | QQHNEFPLT |
| 56 | TrkB-agoAb5702 VH-CDR1 | SFGMH |
| 57 | TrkB-agoAb5702 VH-CDR2 | YITSGSNTIYYADTVKG |
| 58 | TrkB-agoAb5702 VH-CDR3 | DGYFLDALDY |
| 59 | TrkB-agoAb5702 Light chain variable region (VL) | DVQITQSPSYLAASPGETITINCRASKSISK YLAWYQEKPGKTNKLLIYSGSTLQSGIPS RFSGSGSGTDFTLTISSLEPEDFAMYYCQQ HNEFPLTFGAGTKLELK |
| 60 | TrkB-agoAb5702 Heavy variable region (VH) | DVQLVESGGGLVQPGGSRKLSCAASGFT FSSFGMHWVRQAPEKGLEWVAYITSGSN TIYYADTVKGRFTISRDNPKNTLFLQMTS LRSEDTALYYCARDGYFLDALDYWGQG |

Figure 16 (Cont'd)

| | | TSVTVSS |
|---|---|---|
| 61 | TrkB-agoAb6916 VL-CDR1 | SASSSINYTH |
| 62 | TrkB-agoAb6916 VL-CDR2 | DTSKLAS |
| 63 | TrkB-agoAb6916 VL-CDR3 | HQRSSYPWT |
| 64 | TrkB-agoAb6916 VH-CDR1 | SYWVE |
| 65 | TrkB-agoAb6916 VH-CDR2 | EILPGGGSTNYNEKFKG |
| 66 | TrkB-agoAb6916 VH-CDR3 | SDYWFAY |
| 67 | TrkB-agoAb6916 Light chain variable region (VL) | QIVLTQSPAIMSASPGEKVTMTCSASSSIN YTHWFQQKPGTSPKRWIYDTSKLASGVP VRFSGSGSGTSYSLTISSMEAEDAATYYC HQRSSYPWTFGGGTKLEIK |
| 68 | TrkB-agoAb6916 Heavy variable region (VH) | QVQLQQSGTELMKPGASVKISCKAAGYT ISSYWVEWVKQRPGHGLEWIGEILPGGG STNYNEKFKGKATFTADISSNTAYMQLSN LTSEDSAVYYCASSDYWFAYWGQGTLVT VSA |
| 69 | TrkB-agoAb7431 VL-CDR1 | GASQSVSASSYSYIH |
| 70 | TrkB-agoAb7431 VL-CDR2 | YASNLES |
| 71 | TrkB-agoAb7431 VL-CDR3 | QHSWEIPLT |
| 72 | TrkB-agoAb7431 VH-CDR1 | TNYVVN |
| 73 | TrkB-agoAb7431 VH-CDR2 | WINTNTGEPTYAEEFKG |
| 74 | TrkB-agoAb7431 VH-CDR3 | GGAHYFDY |
| 75 | TrkB-agoAb7431 Light chain variable region (VL) | DIVLTQSPASLAVSLGQRATISCGASQSVS ASSYSYIHWFQQKPGQPPKLLIKYASNLE SGVPARFSGSGSGTDFTLNIHPVEEVDTAT YYCQHSWEIPLTFGAGTKLELK |
| 76 | TrkB-agoAb7431 Heavy variable region (VH) | QIQLVQSGPELKKPGETVKISCKASGYTF TNYVVNWVKQAPGKGLKWMGWINTNT GEPTYAEEFKGRFAFSLETSASTAYLQINN LKNVDTATYFCARGGAHYFDYWGQGTT LTVSS |

Figure 16 (Cont'd)

SEQUENCE LISTING

<160> NUMBER OF SEQ ID NOS: 76

<210> SEQ ID NO 1
<211> LENGTH: 398
<212> TYPE: PRT
<213> ORGANISM: Homo sapiens

<400> SEQUENCE: 1

```
Pro Thr Ser Cys Lys Cys Ser Ala Ser Arg Ile Trp Cys Ser Asp Pro
1               5                   10                  15

Ser Pro Gly Ile Val Ala Phe Pro Arg Leu Glu Pro Asn Ser Val Asp
            20                  25                  30

Pro Glu Asn Ile Thr Glu Ile Phe Ile Ala Asn Gln Lys Arg Leu Glu
        35                  40                  45

Ile Ile Asn Glu Asp Asp Val Glu Ala Tyr Val Gly Leu Arg Asn Leu
    50                  55                  60

Thr Ile Val Asp Ser Gly Leu Lys Phe Val Ala His Lys Ala Phe Leu
65                  70                  75                  80

Lys Asn Ser Asn Leu Gln His Ile Asn Phe Thr Arg Asn Lys Leu Thr
                85                  90                  95

Ser Leu Ser Arg Lys His Phe Arg His Leu Asp Leu Ser Glu Leu Ile
            100                 105                 110

Leu Val Gly Asn Pro Phe Thr Cys Ser Cys Asp Ile Met Trp Ile Lys
        115                 120                 125

Thr Leu Gln Glu Ala Lys Ser Ser Pro Asp Thr Gln Asp Leu Tyr Cys
    130                 135                 140

Leu Asn Glu Ser Ser Lys Asn Ile Pro Leu Ala Asn Leu Gln Ile Pro
145                 150                 155                 160

Asn Cys Gly Leu Pro Ser Ala Asn Leu Ala Ala Pro Asn Leu Thr Val
                165                 170                 175

Glu Glu Gly Lys Ser Ile Thr Leu Ser Cys Ser Val Ala Gly Asp Pro
            180                 185                 190

Val Pro Asn Met Tyr Trp Asp Val Gly Asn Leu Val Ser Lys His Met
        195                 200                 205

Asn Glu Thr Ser His Thr Gln Gly Ser Leu Arg Ile Thr Asn Ile Ser
    210                 215                 220

Ser Asp Asp Ser Gly Lys Gln Ile Ser Cys Val Ala Glu Asn Leu Val
225                 230                 235                 240
```

Gly Glu Asp Gln Asp Ser Val Asn Leu Thr Val His Phe Ala Pro Thr
            245                 250                 255

Ile Thr Phe Leu Glu Ser Pro Thr Ser Asp His His Trp Cys Ile Pro
        260                 265                 270

Phe Thr Val Lys Gly Asn Pro Lys Pro Ala Leu Gln Trp Phe Tyr Asn
    275                 280                 285

Gly Ala Ile Leu Asn Glu Ser Lys Tyr Ile Cys Thr Lys Ile His Val
290                 295                 300

Thr Asn His Thr Glu Tyr His Gly Cys Leu Gln Leu Asp Asn Pro Thr
305                 310                 315                 320

His Met Asn Asn Gly Asp Tyr Thr Leu Ile Ala Lys Asn Glu Tyr Gly
                325                 330                 335

Lys Asp Glu Lys Gln Ile Ser Ala His Phe Met Gly Trp Pro Gly Ile
            340                 345                 350

Asp Asp Gly Ala Asn Pro Asn Tyr Pro Asp Val Ile Tyr Glu Asp Tyr
        355                 360                 365

Gly Thr Ala Ala Asn Asp Ile Gly Asp Thr Thr Asn Arg Ser Asn Glu
    370                 375                 380

Ile Pro Ser Thr Asp Val Thr Asp Lys Thr Gly Arg Glu His
385                 390                 395

<210> SEQ ID NO 2
<211> LENGTH: 30
<212> TYPE: PRT
<213> ORGANISM: Homo sapiens

<400> SEQUENCE: 2

Pro Thr Ser Cys Lys Cys Ser Ala Ser Arg Ile Trp Cys Ser Asp Pro
1               5                   10                  15

Ser Pro Gly Ile Val Ala Phe Pro Arg Leu Glu Pro Asn Ser
            20                  25                  30

<210> SEQ ID NO 3
<211> LENGTH: 46
<212> TYPE: PRT
<213> ORGANISM: Homo sapiens

<400> SEQUENCE: 3

Gly Leu Arg Asn Leu Thr Ile Val Asp Ser Gly Leu Lys Phe Val Ala
1               5                   10                  15

His Lys Ala Phe Leu Lys Asn Ser Asn Leu Gln His Ile Asn Phe Thr
            20                  25                  30

Arg Asn Lys Leu Thr Ser Leu Ser Arg Lys His Phe Arg His
        35                  40                  45

<210> SEQ ID NO 4
<211> LENGTH: 49
<212> TYPE: PRT
<213> ORGANISM: Homo sapiens

<400> SEQUENCE: 4

Asn Pro Phe Thr Cys Ser Cys Asp Ile Met Trp Ile Lys Thr Leu Gln
1               5                   10                  15

Glu Ala Lys Ser Ser Pro Asp Thr Gln Asp Leu Tyr Cys Leu Asn Glu
            20                  25                  30

Ser Ser Lys Asn Ile Pro Leu Ala Asn Leu Gln Ile Pro Asn Cys Gly
        35                  40                  45

Leu

<210> SEQ ID NO 5
<211> LENGTH: 86
<212> TYPE: PRT
<213> ORGANISM: Homo sapiens

<400> SEQUENCE: 5

Pro Ser Ala Asn Leu Ala Ala Pro Asn Leu Thr Val Glu Glu Gly Lys
1               5                   10                  15
Ser Ile Thr Leu Ser Cys Ser Val Ala Gly Asp Pro Val Pro Asn Met
            20                  25                  30
Tyr Trp Asp Val Gly Asn Leu Val Ser Lys His Met Asn Glu Thr Ser
        35                  40                  45
His Thr Gln Gly Ser Leu Arg Ile Thr Asn Ile Ser Ser Asp Asp Ser
    50                  55                  60
Gly Lys Gln Ile Ser Cys Val Ala Glu Asn Leu Val Gly Glu Asp Gln
65                  70                  75                  80
Asp Ser Val Asn Leu Thr
                85

<210> SEQ ID NO 6
<211> LENGTH: 70
<212> TYPE: PRT
<213> ORGANISM: Homo sapiens

<400> SEQUENCE: 6

Thr Ser Asp His His Trp Cys Ile Pro Phe Thr Val Lys Gly Asn Pro
1               5                   10                  15
Lys Pro Ala Leu Gln Trp Phe Tyr Asn Gly Ala Ile Leu Asn Glu Ser
            20                  25                  30
Lys Tyr Ile Cys Thr Lys Ile His Val Thr Asn His Thr Glu Tyr His
        35                  40                  45
Gly Cys Leu Gln Leu Asp Asn Pro Thr His Met Asn Asn Gly Asp Tyr
    50                  55                  60
Thr Leu Ile Ala Lys Asn
65                  70

<210> SEQ ID NO 7
<211> LENGTH: 65
<212> TYPE: PRT
<213> ORGANISM: Homo sapiens

<400> SEQUENCE: 7

Glu Tyr Gly Lys Asp Glu Lys Gln Ile Ser Ala His Phe Met Gly Trp
1               5                   10                  15
Pro Gly Ile Asp Asp Gly Ala Asn Pro Asn Tyr Pro Asp Val Ile Tyr
            20                  25                  30
Glu Asp Tyr Gly Thr Ala Ala Asn Asp Ile Gly Asp Thr Thr Asn Arg
        35                  40                  45
Ser Asn Glu Ile Pro Ser Thr Asp Val Thr Asp Lys Thr Gly Arg Glu
    50                  55                  60
His
65

<210> SEQ ID NO 8
<211> LENGTH: 457
<212> TYPE: PRT
<213> ORGANISM: Homo sapiens

<400> SEQUENCE: 8

```
Glu Tyr Gly Lys Asp Glu Lys Gln Ile Ser Ala His Phe Met Gly Trp
  1               5                  10                  15

Pro Gly Ile Asp Asp Gly Ala Asn Pro Asn Tyr Pro Asp Val Ile Tyr
             20                  25                  30

Glu Asp Tyr Gly Thr Ala Ala Asn Asp Ile Gly Asp Thr Thr Asn Arg
         35                  40                  45

Ser Asn Glu Ile Pro Ser Thr Asp Val Thr Asp Lys Thr Gly Arg Glu
 50                  55                  60

His Leu Ser Val Tyr Ala Val Val Ile Ala Ser Val Val Gly Phe
 65                  70                  75                  80

Cys Leu Leu Val Met Leu Phe Leu Leu Lys Leu Ala Arg His Ser Lys
                 85                  90                  95

Phe Gly Met Lys Gly Pro Ala Ser Val Ile Ser Asn Asp Asp Ser
            100                 105                 110

Ala Ser Pro Leu His His Ile Ser Asn Gly Ser Asn Thr Pro Ser Ser
            115                 120                 125

Ser Glu Gly Gly Pro Asp Ala Val Ile Ile Gly Met Thr Lys Ile Pro
130                 135                 140

Val Ile Glu Asn Pro Gln Tyr Phe Gly Ile Thr Asn Ser Gln Leu Lys
145                 150                 155                 160

Pro Asp Thr Phe Val Gln His Ile Lys Arg His Asn Ile Val Leu Lys
                165                 170                 175

Arg Glu Leu Gly Glu Gly Ala Phe Gly Lys Val Phe Leu Ala Glu Cys
                180                 185                 190

Tyr Asn Leu Cys Pro Glu Gln Asp Lys Ile Leu Val Ala Val Lys Thr
            195                 200                 205

Leu Lys Asp Ala Ser Asp Asn Ala Arg Lys Asp Phe His Arg Glu Ala
210                 215                 220

Glu Leu Leu Thr Asn Leu Gln His Glu His Ile Val Lys Phe Tyr Gly
225                 230                 235                 240

Val Cys Val Glu Gly Asp Pro Leu Ile Met Val Phe Glu Tyr Met Lys
                245                 250                 255

His Gly Asp Leu Asn Lys Phe Leu Arg Ala His Gly Pro Asp Ala Val
            260                 265                 270

Leu Met Ala Glu Gly Asn Pro Pro Thr Glu Leu Thr Gln Ser Gln Met
            275                 280                 285

Leu His Ile Ala Gln Gln Ile Ala Ala Gly Met Val Tyr Leu Ala Ser
290                 295                 300

Gln His Phe Val His Arg Asp Leu Ala Thr Arg Asn Cys Leu Val Gly
305                 310                 315                 320

Glu Asn Leu Leu Val Lys Ile Gly Asp Phe Gly Met Ser Arg Asp Val
                325                 330                 335

Tyr Ser Thr Asp Tyr Tyr Arg Val Gly Gly His Thr Met Leu Pro Ile
            340                 345                 350

Arg Trp Met Pro Pro Glu Ser Ile Met Tyr Arg Lys Phe Thr Thr Glu
            355                 360                 365

Ser Asp Val Trp Ser Leu Gly Val Val Leu Trp Glu Ile Phe Thr Tyr
370                 375                 380

Gly Lys Gln Pro Trp Tyr Gln Leu Ser Asn Asn Glu Val Ile Glu Cys
385                 390                 395                 400

Ile Thr Gln Gly Arg Val Leu Gln Arg Pro Arg Thr Cys Pro Gln Glu
            405                 410                 415
```

```
Val Tyr Glu Leu Met Leu Gly Cys Trp Gln Arg Glu Pro His Met Arg
            420                 425                 430

Lys Asn Ile Lys Gly Ile His Thr Leu Leu Gln Asn Leu Ala Lys Ala
            435                 440                 445

Ser Pro Val Tyr Leu Asp Ile Leu Gly
            450                 455

<210> SEQ ID NO 9
<211> LENGTH: 11
<212> TYPE: PRT
<213> ORGANISM: Mus musculus

<400> SEQUENCE: 9

Gln Ala Ser Glu Ser Ile Gly Asn Gly Ile Ala
1               5                   10

<210> SEQ ID NO 10
<211> LENGTH: 7
<212> TYPE: PRT
<213> ORGANISM: Mus musculus

<400> SEQUENCE: 10

Tyr Ala Ser Tyr Leu Ala Ser
1               5

<210> SEQ ID NO 11
<211> LENGTH: 12
<212> TYPE: PRT
<213> ORGANISM: Mus musculus

<400> SEQUENCE: 11

Gln Gly Tyr Tyr Tyr Gly Thr Ser Gly Asp Tyr Ala
1               5                   10

<210> SEQ ID NO 12
<211> LENGTH: 5
<212> TYPE: PRT
<213> ORGANISM: Mus musculus

<400> SEQUENCE: 12

Arg Tyr Trp Met Asn
1               5

<210> SEQ ID NO 13
<211> LENGTH: 16
<212> TYPE: PRT
<213> ORGANISM: Mus musculus

<400> SEQUENCE: 13

Thr Ile Ser Thr Gly Asp Thr Thr Ser Tyr Ala Ser Trp Ala Lys Gly
1               5                   10                  15

<210> SEQ ID NO 14
<211> LENGTH: 11
<212> TYPE: PRT
<213> ORGANISM: Mus musculus

<400> SEQUENCE: 14

Gly Asp Tyr Gln Thr Ala Ser Tyr Phe Asn Leu
1               5                   10

<210> SEQ ID NO 15
<211> LENGTH: 16
```

```
<212> TYPE: PRT
<213> ORGANISM: Mus musculus

<400> SEQUENCE: 15

Arg Ser Ser Gln Asn Ile Val His Ser Asn Gly Asn Thr Tyr Leu Glu
1               5                   10                  15

<210> SEQ ID NO 16
<211> LENGTH: 7
<212> TYPE: PRT
<213> ORGANISM: Mus musculus

<400> SEQUENCE: 16

Asn Val Ser Asn Arg Phe Ser
1               5

<210> SEQ ID NO 17
<211> LENGTH: 9
<212> TYPE: PRT
<213> ORGANISM: Mus musculus

<400> SEQUENCE: 17

Phe Gln Gly Ser His Phe Pro Trp Thr
1               5

<210> SEQ ID NO 18
<211> LENGTH: 5
<212> TYPE: PRT
<213> ORGANISM: Mus musculus

<400> SEQUENCE: 18

Ser Tyr Thr Met Ser
1               5

<210> SEQ ID NO 19
<211> LENGTH: 17
<212> TYPE: PRT
<213> ORGANISM: Mus musculus

<400> SEQUENCE: 19

Thr Ile Ser Ser Gly Gly Asp Tyr Thr Tyr Phe Pro Asp Ser Val Lys
1               5                   10                  15

Gly

<210> SEQ ID NO 20
<211> LENGTH: 9
<212> TYPE: PRT
<213> ORGANISM: Mus musculus

<400> SEQUENCE: 20

Glu Ser Gly Arg Gly Asp Phe Asp Tyr
1               5

<210> SEQ ID NO 21
<211> LENGTH: 11
<212> TYPE: PRT
<213> ORGANISM: Mus musculus

<400> SEQUENCE: 21

Gln Ala Ser Glu Ser Ile Gly Ser Tyr Leu Ala
1               5                   10

<210> SEQ ID NO 22
<211> LENGTH: 7
```

```
<212> TYPE: PRT
<213> ORGANISM: Mus musculus

<400> SEQUENCE: 22

Arg Ala Ser Thr Leu Ala Ser
1               5

<210> SEQ ID NO 23
<211> LENGTH: 12
<212> TYPE: PRT
<213> ORGANISM: Mus musculus

<400> SEQUENCE: 23

Gln Gln Gly Phe Ile Gly Thr Asn Val Asp Asn Thr
1               5                   10

<210> SEQ ID NO 24
<211> LENGTH: 5
<212> TYPE: PRT
<213> ORGANISM: Mus musculus

<400> SEQUENCE: 24

Asn Tyr Trp Met Ile
1               5

<210> SEQ ID NO 25
<211> LENGTH: 17
<212> TYPE: PRT
<213> ORGANISM: Mus musculus

<400> SEQUENCE: 25

Ser Ile Ser Thr Leu Ser Asp Asn Thr Trp Tyr Ala Asn Trp Val Asn
1               5                   10                  15

Gly

<210> SEQ ID NO 26
<211> LENGTH: 13
<212> TYPE: PRT
<213> ORGANISM: Mus musculus

<400> SEQUENCE: 26

Gly Val Gly Gly Val Leu Gly Thr Ser Gly Met Asp Pro
1               5                   10

<210> SEQ ID NO 27
<211> LENGTH: 112
<212> TYPE: PRT
<213> ORGANISM: Mus musculus

<400> SEQUENCE: 27

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Asn Leu Leu Ile Tyr Asn Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95
```

Ser His Phe Pro Trp Thr Phe Gly Gly Gly Thr Lys Leu Glu Ile Thr
            100                 105                 110

<210> SEQ ID NO 28
<211> LENGTH: 118
<212> TYPE: PRT
<213> ORGANISM: Mus musculus

<400> SEQUENCE: 28

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Asp Tyr Thr Tyr Phe Pro Asp Ser Val
    50                  55                  60

Lys Gly Arg Phe Thr Met Ser Arg Asp Asn Ala Lys Asn Ala Leu Tyr
65                  70                  75                  80

Leu Gln Met Ser Ser Leu Lys Ser Glu Asp Thr Ala Met Tyr Tyr Cys
                85                  90                  95

Thr Arg Glu Ser Gly Arg Gly Asp Phe Asp Tyr Trp Gly Gln Gly Thr
            100                 105                 110

Thr Leu Thr Val Ser Ser
        115

<210> SEQ ID NO 29
<211> LENGTH: 15
<212> TYPE: PRT
<213> ORGANISM: Mus musculus

<400> SEQUENCE: 29

Arg Ala Ser Glu Ser Val Asp Asn Tyr Gly Asn Ser Leu Met His
1               5                   10                  15

<210> SEQ ID NO 30
<211> LENGTH: 7
<212> TYPE: PRT
<213> ORGANISM: Mus musculus

<400> SEQUENCE: 30

Leu Ala Ser Asn Leu Glu Ser
1               5

<210> SEQ ID NO 31
<211> LENGTH: 10
<212> TYPE: PRT
<213> ORGANISM: Mus musculus

<400> SEQUENCE: 31

Gln Gln Asn Asn Glu Asp Pro Pro Trp Thr
1               5                   10

<210> SEQ ID NO 32
<211> LENGTH: 5
<212> TYPE: PRT
<213> ORGANISM: Mus musculus

<400> SEQUENCE: 32

Ser Ser Trp Met Asn
1               5

<210> SEQ ID NO 33
<211> LENGTH: 17
<212> TYPE: PRT
<213> ORGANISM: Mus musculus

<400> SEQUENCE: 33

Arg Ile Tyr Pro Gly Asp Gly His Thr Asn Tyr Asn Gly Lys Phe Lys
1               5                   10                  15
Gly

<210> SEQ ID NO 34
<211> LENGTH: 9
<212> TYPE: PRT
<213> ORGANISM: Mus musculus

<400> SEQUENCE: 34

Ser Gly Tyr Gly Tyr Gly Phe Asp Cys
1               5

<210> SEQ ID NO 35
<211> LENGTH: 131
<212> TYPE: PRT
<213> ORGANISM: Mus musculus

<400> SEQUENCE: 35

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Ser Leu Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Lys
        115                 120                 125

Leu Gly Val
    130

<210> SEQ ID NO 36
<211> LENGTH: 135
<212> TYPE: PRT
<213> ORGANISM: Mus musculus

<400> SEQUENCE: 36

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly His Thr Asn Tyr Asn Gly Lys Phe
    50                  55                  60

```
Lys Gly Lys Ala Thr Leu Thr Ala Asp Lys Ser Ser Thr Ala Tyr
 65                  70                  75                  80

Met Gln Leu Thr Ser Leu Thr Ser Val Asp Ser Gly Val Tyr Phe Cys
                 85                  90                  95

Ala Arg Ser Gly Tyr Gly Tyr Gly Phe Asp Cys Trp Gly Gln Gly Thr
            100                 105                 110

Thr Leu Thr Val Ser Ser Ala Lys Thr Thr Pro Pro Ser Val Tyr Pro
        115                 120                 125

Leu Val Pro Gly Ser Leu Ala
        130             135

<210> SEQ ID NO 37
<211> LENGTH: 11
<212> TYPE: PRT
<213> ORGANISM: Mus musculus

<400> SEQUENCE: 37

Arg Ser Ser Glu Asn Ile Tyr Ser Tyr Leu Ala
1               5                   10

<210> SEQ ID NO 38
<211> LENGTH: 7
<212> TYPE: PRT
<213> ORGANISM: Mus musculus

<400> SEQUENCE: 38

Asn Ala Lys Thr Leu Ala Glu
1               5

<210> SEQ ID NO 39
<211> LENGTH: 9
<212> TYPE: PRT
<213> ORGANISM: Mus musculus

<400> SEQUENCE: 39

Gln His His Tyr Gly Pro Pro Tyr Thr
1               5

<210> SEQ ID NO 40
<211> LENGTH: 5
<212> TYPE: PRT
<213> ORGANISM: Mus musculus

<400> SEQUENCE: 40

Arg Tyr Trp Met Gln
1               5

<210> SEQ ID NO 41
<211> LENGTH: 17
<212> TYPE: PRT
<213> ORGANISM: Mus musculus

<400> SEQUENCE: 41

Ala Ile Tyr Pro Gly Asp Gly Asp Thr Arg Tyr Thr Gln Lys Phe Lys
1               5                   10                  15

Gly

<210> SEQ ID NO 42
<211> LENGTH: 10
<212> TYPE: PRT
<213> ORGANISM: Mus musculus
```

```
<400> SEQUENCE: 42

Ser Gly Leu Gly Arg Ala Trp Phe Thr Tyr
1               5                   10

<210> SEQ ID NO 43
<211> LENGTH: 107
<212> TYPE: PRT
<213> ORGANISM: Mus musculus

<400> SEQUENCE: 43

Asp Ile Gln Met Thr Gln Ser Pro Ala Ser Leu Ser Ala Ser Val Gly
1               5                   10                  15

Glu Thr Val Thr Ile Thr Cys Arg Ser Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Pro Pro Tyr
                85                  90                  95

Thr Phe Gly Gly Gly Thr Lys Leu Glu Ile Lys
            100                 105

<210> SEQ ID NO 44
<211> LENGTH: 119
<212> TYPE: PRT
<213> ORGANISM: Mus musculus

<400> SEQUENCE: 44

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Arg Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Gly Ser Gly Leu Gly Arg Ala Trp Phe Thr Tyr Trp Gly Gln Gly
            100                 105                 110

Thr Leu Val Thr Val Ser Ala
        115

<210> SEQ ID NO 45
<211> LENGTH: 11
<212> TYPE: PRT
<213> ORGANISM: Mus musculus

<400> SEQUENCE: 45

Leu Ala Ser Gln Thr Ile Gly Thr Leu Leu Ala
1               5                   10

<210> SEQ ID NO 46
```

```
<211> LENGTH: 7
<212> TYPE: PRT
<213> ORGANISM: Mus musculus

<400> SEQUENCE: 46

Ala Ala Thr Thr Leu Ala Asp
1               5

<210> SEQ ID NO 47
<211> LENGTH: 9
<212> TYPE: PRT
<213> ORGANISM: Mus musculus

<400> SEQUENCE: 47

Gln Gln Phe Tyr Ser Thr Pro Tyr Thr
1               5

<210> SEQ ID NO 48
<211> LENGTH: 5
<212> TYPE: PRT
<213> ORGANISM: Mus musculus

<400> SEQUENCE: 48

Arg Tyr Trp Met Ser
1               5

<210> SEQ ID NO 49
<211> LENGTH: 17
<212> TYPE: PRT
<213> ORGANISM: Mus musculus

<400> SEQUENCE: 49

Glu Ile Asn Pro Asp Gly Ser Thr Ile Asn Tyr Thr Pro Ser Leu Lys
1               5                   10                  15

Asp

<210> SEQ ID NO 50
<211> LENGTH: 13
<212> TYPE: PRT
<213> ORGANISM: Mus musculus

<400> SEQUENCE: 50

Gly Asn Tyr Tyr Gly Ser Ser Leu Ala Trp Phe Ala Tyr
1               5                   10

<210> SEQ ID NO 51
<211> LENGTH: 107
<212> TYPE: PRT
<213> ORGANISM: Mus musculus

<400> SEQUENCE: 51

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Leu
                20                  25                  30

Leu Ala Trp Tyr Gln Gln Lys Pro Gly Lys Ser Pro Gln Leu Leu Ile
            35                  40                  45

Tyr Ala Ala Thr Thr Leu Ala Asp Gly Val Pro Ser Arg Phe Arg Gly
        50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Phe Tyr Ser Thr Pro Tyr
```

```
                    85                  90                  95
Thr Phe Gly Gly Gly Thr Lys Leu Glu Ile Lys
            100                 105

<210> SEQ ID NO 52
<211> LENGTH: 122
<212> TYPE: PRT
<213> ORGANISM: Mus musculus

<400> SEQUENCE: 52

Glu Val Lys Leu Val Glu Ser Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Gly Ser Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Gly Ser Ser Leu Ala Trp Phe Ala Tyr Trp
            100                 105                 110

Gly Gln Gly Thr Leu Val Thr Val Ser Ala
        115                 120

<210> SEQ ID NO 53
<211> LENGTH: 11
<212> TYPE: PRT
<213> ORGANISM: Mus musculus

<400> SEQUENCE: 53

Arg Ala Ser Lys Ser Ile Ser Lys Tyr Leu Ala
1               5                   10

<210> SEQ ID NO 54
<211> LENGTH: 7
<212> TYPE: PRT
<213> ORGANISM: Mus musculus

<400> SEQUENCE: 54

Ser Gly Ser Thr Leu Gln Ser
1               5

<210> SEQ ID NO 55
<211> LENGTH: 9
<212> TYPE: PRT
<213> ORGANISM: Mus musculus

<400> SEQUENCE: 55

Gln Gln His Asn Glu Phe Pro Leu Thr
1               5

<210> SEQ ID NO 56
<211> LENGTH: 5
<212> TYPE: PRT
<213> ORGANISM: Mus musculus

<400> SEQUENCE: 56

Ser Phe Gly Met His
```

<210> SEQ ID NO 57
<211> LENGTH: 17
<212> TYPE: PRT
<213> ORGANISM: Mus musculus

<400> SEQUENCE: 57

Tyr Ile Thr Ser Gly Ser Asn Thr Ile Tyr Tyr Ala Asp Thr Val Lys
1               5                   10                  15

Gly

<210> SEQ ID NO 58
<211> LENGTH: 10
<212> TYPE: PRT
<213> ORGANISM: Mus musculus

<400> SEQUENCE: 58

Asp Gly Tyr Phe Leu Asp Ala Leu Asp Tyr
1               5                   10

<210> SEQ ID NO 59
<211> LENGTH: 107
<212> TYPE: PRT
<213> ORGANISM: Mus musculus

<400> SEQUENCE: 59

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Phe Pro Leu
                85                  90                  95

Thr Phe Gly Ala Gly Thr Lys Leu Glu Leu Lys
            100                 105

<210> SEQ ID NO 60
<211> LENGTH: 119
<212> TYPE: PRT
<213> ORGANISM: Mus musculus

<400> SEQUENCE: 60

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Thr Ser Gly Ser Asn Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Leu Tyr Tyr Cys

```
                    85                  90                  95
Ala Arg Asp Gly Tyr Phe Leu Asp Ala Leu Asp Tyr Trp Gly Gln Gly
            100                 105                 110
Thr Ser Val Thr Val Ser Ser
        115

<210> SEQ ID NO 61
<211> LENGTH: 10
<212> TYPE: PRT
<213> ORGANISM: Mus musculus

<400> SEQUENCE: 61

Ser Ala Ser Ser Ser Ile Asn Tyr Thr His
1               5                   10

<210> SEQ ID NO 62
<211> LENGTH: 7
<212> TYPE: PRT
<213> ORGANISM: Mus musculus

<400> SEQUENCE: 62

Asp Thr Ser Lys Leu Ala Ser
1               5

<210> SEQ ID NO 63
<211> LENGTH: 9
<212> TYPE: PRT
<213> ORGANISM: Mus musculus

<400> SEQUENCE: 63

His Gln Arg Ser Ser Tyr Pro Trp Thr
1               5

<210> SEQ ID NO 64
<211> LENGTH: 5
<212> TYPE: PRT
<213> ORGANISM: Mus musculus

<400> SEQUENCE: 64

Ser Tyr Trp Val Glu
1               5

<210> SEQ ID NO 65
<211> LENGTH: 17
<212> TYPE: PRT
<213> ORGANISM: Mus musculus

<400> SEQUENCE: 65

Glu Ile Leu Pro Gly Gly Gly Ser Thr Asn Tyr Asn Glu Lys Phe Lys
1               5                   10                  15

Gly

<210> SEQ ID NO 66
<211> LENGTH: 7
<212> TYPE: PRT
<213> ORGANISM: Mus musculus

<400> SEQUENCE: 66

Ser Asp Tyr Trp Phe Ala Tyr
1               5

<210> SEQ ID NO 67
<211> LENGTH: 106
```

```
<212> TYPE: PRT
<213> ORGANISM: Mus musculus

<400> SEQUENCE: 67

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Asn Tyr Thr
                20                  25                  30

His Trp Phe Gln Gln Lys Pro Gly Thr Ser Pro Lys Arg Trp Ile Tyr
            35                  40                  45

Asp Thr Ser Lys Leu Ala Ser Gly Val Pro Val Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Trp Thr
                85                  90                  95

Phe Gly Gly Gly Thr Lys Leu Glu Ile Lys
            100                 105

<210> SEQ ID NO 68
<211> LENGTH: 116
<212> TYPE: PRT
<213> ORGANISM: Mus musculus

<400> SEQUENCE: 68

Gln Val Gln Leu Gln Gln Ser Gly Thr Glu Leu Met Lys Pro Gly Ala
1               5                   10                  15

Ser Val Lys Ile Ser Cys Lys Ala Ala Gly Tyr Thr Ile Ser Ser Tyr
                20                  25                  30

Trp Val Glu Trp Val Lys Gln Arg Pro Gly His Gly Leu Glu Trp Ile
            35                  40                  45

Gly Glu Ile Leu Pro Gly Gly Ser Thr Asn Tyr Asn Glu Lys Phe
        50                  55                  60

Lys Gly Lys Ala Thr Phe Thr Ala Asp Ile Ser Ser Asn Thr Ala Tyr
65                  70                  75                  80

Met Gln Leu Ser Asn Leu Thr Ser Glu Asp Ser Ala Val Tyr Tyr Cys
                85                  90                  95

Ala Ser Ser Asp Tyr Trp Phe Ala Tyr Trp Gly Gln Gly Thr Leu Val
            100                 105                 110

Thr Val Ser Ala
        115

<210> SEQ ID NO 69
<211> LENGTH: 15
<212> TYPE: PRT
<213> ORGANISM: Mus musculus

<400> SEQUENCE: 69

Gly Ala Ser Gln Ser Val Ser Ala Ser Ser Tyr Ser Tyr Ile His
1               5                   10                  15

<210> SEQ ID NO 70
<211> LENGTH: 7
<212> TYPE: PRT
<213> ORGANISM: Mus musculus

<400> SEQUENCE: 70

Tyr Ala Ser Asn Leu Glu Ser
1               5
```

<210> SEQ ID NO 71
<211> LENGTH: 9
<212> TYPE: PRT
<213> ORGANISM: Mus musculus

<400> SEQUENCE: 71

Gln His Ser Trp Glu Ile Pro Leu Thr
1               5

<210> SEQ ID NO 72
<211> LENGTH: 6
<212> TYPE: PRT
<213> ORGANISM: Mus musculus

<400> SEQUENCE: 72

Thr Asn Tyr Val Val Asn
1               5

<210> SEQ ID NO 73
<211> LENGTH: 17
<212> TYPE: PRT
<213> ORGANISM: Mus musculus

<400> SEQUENCE: 73

Trp Ile Asn Thr Asn Thr Gly Glu Pro Thr Tyr Ala Glu Glu Phe Lys
1               5                   10                  15

Gly

<210> SEQ ID NO 74
<211> LENGTH: 8
<212> TYPE: PRT
<213> ORGANISM: Mus musculus

<400> SEQUENCE: 74

Gly Gly Ala His Tyr Phe Asp Tyr
1               5

<210> SEQ ID NO 75
<211> LENGTH: 111
<212> TYPE: PRT
<213> ORGANISM: Mus musculus

<400> SEQUENCE: 75

Asp Ile Val Leu Thr Gln Ser Pro Ala Ser Leu Ala Val Ser Leu Gly
1               5                   10                  15

Gln Arg Ala Thr Ile Ser Cys Gly Ala Ser Gln Ser Val Ser Ala Ser
            20                  25                  30

Ser Tyr Ser Tyr Ile His Trp Phe Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Val Asp Thr Ala Thr Tyr Tyr Cys Gln His Ser Trp
                85                  90                  95

Glu Ile Pro Leu Thr Phe Gly Ala Gly Thr Lys Leu Glu Leu Lys
            100                 105                 110

<210> SEQ ID NO 76
<211> LENGTH: 117

```
<212> TYPE: PRT
<213> ORGANISM: Mus musculus

<400> SEQUENCE: 76

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Val Val Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Val Asp Thr Ala Thr Tyr Phe Cys
                85                  90                  95

Ala Arg Gly Gly Ala His Tyr Phe Asp Tyr Trp Gly Gln Gly Thr Thr
            100                 105                 110

Leu Thr Val Ser Ser
            115
```

ANTI-TRKB AGONIST ANTIBODIES BINDING TO D5 DOMAIN OF TRKB AND METHODS OF PROMOTING NEURONAL SURVIVAL IN MOTOR NEURON INJURY, STROKE OR GLAUCOMA

RELATED APPLICATION

The present patent application is a National Stage Entry of International Patent Application No. PCT/CN2018/079109, filed on Mar. 15, 2018, which claims priority to and the benefit of International Patent Application No. PCT/CN2017/076728, filed on Mar. 15, 2017, entitled "NOVEL ANTI-TRKB ANTIBODIES", the entire contents of which are hereby incorporated by reference herein.

FIELD OF THE INVENTION

The present disclosure generally relates to novel anti-TrkB antibodies that specifically bind to human TrkB.

BACKGROUND

Neurodegenerative diseases are the most well-known neurological diseases yet with little advances in its medical intervention. As a devastating disease, Alzheimer's disease (AD) is a huge burden in a growing number of patients and families while the corresponding drug discovery is facing great challenges. Current strategies of AD treatment targeting pathogenic toxins (amyloid β) have failed. Therefore, we have switched our focus to pathophysiology and seek to exploit neurotrophic factors, such as BDNF, as candidates for neurorepair. These neurotrophic factors play significant roles in neuronal development, survival and synaptic plasticity and were thus regarded as the most potential molecules in treatment of neurological diseases. However, there are limitations of these natural products lying in their biochemical properties that hamper their use as therapeutics. The few clinical trials have all been disappointing.

BRIEF SUMMARY OF THE INVENTION

Antibodies specific for TrkB as provided in the present disclosure can facilitate dimerization of the receptor and activate the downstream signaling pathways with neurotrophic property. After screening, antibodies with good pharmacokinetics and low effective concentration can be selected as candidate antibody drug. These candidates exhibit biological functions but excel BDNF in the following ways: (1) Physicochemical property: BDNF is too sticky to diffuse while TrkB agonist antibody (TrkB-AgoAb) easily diffuses to targets; (2) Specificity: BDNF activates not only TrkB but also p75NTR that leads to neuronal death and synaptic inhibition whereas TrkB-AgoAb is specific for TrkB; (3) Pharmacokinetics: The half-life of BDNF is a few hours while it is weeks for TrkB-AgoAb; (4) TrkB-AgoAb is much lower in manufacture cost. The present disclosure provides antibody screening, selection and evaluation of the TrkB-AgoAbs' biological and pharmaceutical properties. Both in vitro and in vivo effects of TrkB-AgoAbs in multiple neurological disorders were also tested in the present disclosure. TrkB-AgoAb can be clinically used in the treatment of AD, stroke and other neurodegenerative diseases such as ALS, glaucoma, Huntington's disease, etc.

The present disclosure provides a novel monoclonal TrkB agonist antibodies, polynucleotides encoding the same, methods of using the same and binding epitopes thereof on the human TrkB protein.

The present disclosure provides an isolated TrkB agonist antibody that binds to an epitope contained in one of the extracellular domains of TrkB and is capable of activating TrkB, wherein the extracellular domains comprises extracellular D1 domain having the sequence of SEQ ID NO: 2, D2 domain having the sequence of SEQ ID NO: 3, D3 domain having the sequence of SEQ ID NO: 4, D4 domain having the sequence of SEQ ID NO: 5, D5 domain having the sequence of SEQ ID NO: 6 and juxtamembrane domain having the sequence of SEQ ID NO: 7 of TrkB.

In certain embodiments, the antibody binds to an epitope contained in juxtamembrane domain and is capable of activating truncated TrkB having the sequence of SEQ ID NO: 8.

The present disclosure provides an isolated TrkB agonist antibody provided herein binding to the same epitope as or having competitive binding to the antibody disclosed herein.

In certain embodiments, an isolated TrkB agonist antibody is provided herein, comprising 1, 2, 3, 4, 5 or 6 CDRs selected from SEQ ID NOs: 9-26, 29-34, 37-42, 45-50, 53-58, 61-66, and 69-74, or a homologue of at least 80% (e.g. at least 85%, 88%, 90%, 91%, 92%, 93%, 94%, 95%, 96%, 97%, 98%, 99%) sequence identity thereof. In certain embodiments, the TrkB antibody provided herein comprises 3 heavy chain CDR sequences selected from the group consisting of 1) SEQ ID NOs: 12-14, or a homologue of at least 80% (e.g. at least 85%, 88%, 90%, 91%, 92%, 93%, 94%, 95%, 96%, 97%, 98%, 99%) sequence identity thereof; 2) SEQ ID NOs: 18-20, or a homologue of at least 80% (e.g. at least 85%, 88%, 90%, 91%, 92%, 93%, 94%, 95%, 96%, 97%, 98%, 99%) sequence identity thereof; 3) SEQ ID NOs: 24-26, or a homologue of at least 80% (e.g. at least 85%, 88%, 90%, 91%, 92%, 93%, 94%, 95%, 96%, 97%, 98%, 99%) sequence identity thereof; 4) SEQ ID NOs: 32-34, or a homologue of at least 80% (e.g. at least 85%, 88%, 90%, 91%, 92%, 93%, 94%, 95%, 96%, 97%, 98%, 99%) sequence identity thereof; 5) SEQ ID NOs: 40-42, or a homologue of at least 80% (e.g. at least 85%, 88%, 90%, 91%, 92%, 93%, 94%, 95%, 96%, 97%, 98%, 99%) sequence identity thereof; 6) SEQ ID NOs: 48-50, or a homologue of at least 80% (e.g. at least 85%, 88%, 90%, 91%, 92%, 93%, 94%, 95%, 96%, 97%, 98%, 99%) sequence identity thereof; 7) SEQ ID NOs: 56-58, or a homologue of at least 80% (e.g. at least 85%, 88%, 90%, 91%, 92%, 93%, 94%, 95%, 96%, 97%, 98%, 99%) sequence identity thereof; 8) SEQ ID NOs: 64-66, or a homologue of at least 80% (e.g. at least 85%, 88%, 90%, 91%, 92%, 93%, 94%, 95%, 96%, 97%, 98%, 99%) sequence identity thereof; or 9) SEQ ID NOs: 72-74, or a homologue of at least 80% (e.g. at least 85%, 88%, 90%, 91%, 92%, 93%, 94%, 95%, 96%, 97%, 98%, 99%) sequence identity thereof.

In certain embodiments, the TrkB antibody provided herein comprises 3 light chain CDR sequences selected from the group consisting of 1) SEQ ID NOs: 9-11, or a homologue of at least 80% (e.g. at least 85%, 88%, 90%, 91%, 92%, 93%, 94%, 95%, 96%, 97%, 98%, 99%) sequence identity thereof; 2) SEQ ID NOs: 15-17, or a homologue of at least 80% (e.g. at least 85%, 88%, 90%, 91%, 92%, 93%, 94%, 95%, 96%, 97%, 98%, 99%) sequence identity thereof; 3) SEQ ID NOs: 21-23, or a homologue of at least 80% (e.g. at least 85%, 88%, 90%, 91%, 92%, 93%, 94%, 95%, 96%, 97%, 98%, 99%) sequence identity thereof; 4) SEQ ID NOs: 29-31, or a homologue of at least 80% (e.g. at least 85%, 88%, 90%, 91%, 92%, 93%, 94%, 95%, 96%, 97%, 98%, 99%) sequence identity thereof; 5) SEQ ID NOs: 37-39, or a homologue of at least 80% (e.g. at least 85%, 88%, 90%, 91%, 92%, 93%, 94%, 95%, 96%, 97%, 98%, 99%) sequence identity thereof; 6) SEQ ID NOs: 45-47, or a homologue of at least 80% (e.g. at least 85%, 88%, 90%, 91%, 92%, 93%, 94%, 95%, 96%, 97%, 98%, 99%) sequence identity thereof; 7) SEQ ID NOs: 53-55, or a homologue of at least 80% (e.g. at least 85%, 88%, 90%, 91%, 92%, 93%, 94%, 95%, 96%, 97%, 98%, 99%) sequence identity thereof; 8) SEQ ID NOs: 61-63, or a homologue of at least 80% (e.g. at least 85%, 88%, 90%, 91%, 92%, 93%, 94%, 95%, 96%, 97%, 98%, 99%) sequence identity thereof; or 9) SEQ ID NOs: 69-71, or a homologue of at least 80% (e.g. at least 85%, 88%, 90%, 91%, 92%, 93%, 94%, 95%, 96%, 97%, 98%, 99%) sequence identity thereof.

In certain embodiments, an isolated TrkB agonist antibody is provided herein, comprising 1, 2, 3, 4, 5 or 6 CDRs selected from the group consisting of 1) SEQ ID NOs: 12-14, or a variant thereof having 1, 2 or 3 amino acid modifications; 2) SEQ ID NOs: 18-20, or a variant thereof having 1, 2 or 3 amino acid modifications; 3) SEQ ID NOs: 24-26, or a variant thereof having 1, 2 or 3 amino acid modifications; 4) SEQ ID NOs: 32-34, or a variant thereof having 1, 2 or 3 amino acid modifications; 5) SEQ ID NOs: 40-42, or a variant thereof having 1, 2 or 3 amino acid modifications; 6) SEQ ID NOs: 48-50, or a variant thereof having 1, 2 or 3 amino acid modifications; 7) SEQ ID NOs: 56-58, or a variant thereof having 1, 2 or 3 amino acid modifications; 8) SEQ ID NOs: 64-66, or a variant thereof having 1, 2 or 3 amino acid modifications; or 9) SEQ ID NOs: 72-74, or a variant thereof having 1, 2 or 3 amino acid modifications.

In certain embodiments, the TrkB antibody provided herein comprises 3 light chain CDR sequences selected from the group consisting of 1) SEQ ID NOs: 9-11, or a variant thereof having 1, 2 or 3 amino acid modifications; 2) SEQ ID NOs: 15-17, or a variant thereof having 1, 2 or 3 amino acid modifications; 3) SEQ ID NOs: 21-23, or a variant thereof having 1, 2 or 3 amino acid modifications; 4) SEQ ID NOs: 29-31, or a variant thereof having 1, 2 or 3 amino acid modifications; or 5) SEQ ID NOs: 37-39, or a variant thereof having 1, 2 or 3 amino acid modifications; 6) SEQ ID NOs: 45-47, or a variant thereof having 1, 2 or 3 amino acid modifications; 7) SEQ ID NOs: 53-55, or a variant thereof having 1, 2 or 3 amino acid modifications; 8) SEQ ID NOs: 61-63, or a variant thereof having 1, 2 or 3 amino acid modifications; or 9) SEQ ID NOs: 69-71, or a variant thereof having 1, 2 or 3 amino acid modifications.

In certain embodiments, the isolated TrkB agonist antibody provided herein comprises a heavy chain variable region selected from the group consisting of SEQ ID NO: 28, 36, 44, 52, 60, 68, 76 or a humanized version thereof. In certain embodiments, the isolated TrkB agonist antibody provided herein comprises a light chain variable region selected from the group consisting of SEQ ID NO: 27, 35, 43, 51, 59, 67, 75 or a humanized version thereof.

In certain embodiments, the isolated TrkB agonist antibody is capable of activating TrkB with additive effect via binding to a different epitope, or different domain (such as the D1, D2, D3, D4 or Juxta-membrane domain of TrkB) from that of BDNF and/or NT-4, wherein the additive effect is additional increase of TrkB activation by the antibody when TrkB is at peak activation by BDNF and/or NT-4. The epitopes on TrkB for BDNF binding includes Asp349, Asn350, Tyr329, Asp298, Cys302, Cys345 and His299. In certain embodiments, the epitope different from BDNF is within the D1, D2, D3, D4, D5 or Juxta-membrane domain of TrkB.

In certain embodiments, when the antibody binds to TrkB, TrkB is autophosphorylated at amino acid residues of at least one of Tyr515 (i.e. Y515), Tyr701 (i.e. Y701), Tyr705 (i.e. Y705), Tyr706 (i.e. Y706), Tyr816 (i.e. Y816), Tyr490 (i.e. Y490), Tyr670 (i.e. Y670), Tyr674 (i.e. Y674), Tyr675 (i.e. Y675), Tyr771 (i.e. Y771), Tyr783 (i.e. Y783), Tyr785 (i.e. Y785), Tyr1254 (i.e. Y1254) of TrkB.

In certain embodiments, the activation of TrkB by the antibody is less than the activation of TrkB by BDNF and/or NT-4. In certain embodiments, the activation of TrkB by the antibody is 5%-100% (e.g. 80%-100%, 70%-100%, 60%-100%, 50%-100%, 40%-100%, 30%-100%, 20%-100%, 10%-100%, 100%, 90%, 80%, 70&, 60%, 50%, 40%, 30%, 20%, 10%, or 5%) of the activation of TrkB by BDNF and/or NT-4, as determined by the level of TrkB autophosphorylation, the level of phosphorylation in the signaling pathways of MAPK, PI3K or PLCγ, or the combination thereof.

In certain embodiments, the isolated TrkB agonist antibody provided herein is capable of binding to TrkB or an extracellular domain thereof (e.g., D1-D5 domain) with a half-life ($T_{1/2}$) of at least 12 (e.g. 13, 14, 15, 16, 17, 18, 19, 20, 21, 22, 23, 24, 25, 26, 27, 28, 29, 30, 36, 42, 48 or more) hours.

In certain embodiments, the isolated TrkB agonist antibody provided herein has an $EC_{50}$ in terms of binding to TrkB or an extracellular domain thereof (e.g., D1-D5 domain) of less than 4 nM (e.g. less than 3.5 nM, less than 3 nM, less than 2.5 nM, less than 2 nM, less than 1.5 nM, less than 1 nM, less than 0.5 nM, less than 0.4 nM, less than 0.3 nM, less than 0.2 nM, or less than 0.1 nM). In certain embodiments, the isolated TrkB agonist antibody provided herein has an affinity to TrkB or an extracellular domain thereof (e.g., D1-D5 domain) with a $K_D$ value of less than 4.5 nM (e.g. less than 4 nM, less than 3.5 nM, less than 3 nM, less than 2.5 nM, less than 2 nM, less than 1.5 nM, less than 1 nM, less than 0.5 nM, less than 0.4 nM, less than 0.3 nM, less than 0.2 nM, less than 0.1 nM, less than 0.09 nM, less than 0.08 nM, less than 0.07 nM, less than 0.06 nM, or less than 0.05 nM) as measured by Biacore.

In certain embodiments, the isolated TrkB agonist antibody provided herein does not bind to P75 neurotrophin receptor (P75NTR), Tyrosine Receptor A (TrkA) or Tyrosine Receptor C (TrkC).

In certain embodiments, the isolated TrkB agonist antibody provided herein is capable of enhancing neural cell survival, regulating synaptic development and/or plasticity, enhancing neurite outgrowth, or the combination thereof. In certain embodiments, the neural cell comprises PC12 cells, hippocampal neurons, retinal ganglion cells, motor neurons, and dopaminergic neurons. In certain embodiments, the regulated synaptic plasticity comprises increased synapses, enhanced synaptic transmission, enhanced long term potentiation (LTP), and enhanced γ oscillation.

The present disclosure also provides a pharmaceutical composition comprising a therapeutically effective amount of the isolated TrkB agonist antibody provided herein and a pharmaceutical carrier. In certain embodiments, the pharmaceutical composition further comprises a second therapeutic agent. In certain embodiments, the second therapeutic agent is BDNF and/or NT-4.

In one aspect, the present disclosure provides a kit comprising the TrkB agonist antibody or the pharmaceutical composition in diagnosing, preventing, delaying or treating the TrkB associated conditions.

In one aspect, the present disclosure provides a polynucleotide encoding the isolated TrkB agonist antibody. In one aspect, the present disclosure provides a vector comprising the polynucleotide. In one aspect, the present disclosure provides an isolated host cell comprising the vector. In certain embodiments, the host cell produces the antibody encoded by the polynucleotide.

In one aspect, the present disclosure provides a method of producing an antibody which specifically binds to TrkB, comprising introducing a polynucleotide encoding the TrkB protein into the host cell and culturing the host cell under the condition at which the polynucleotide is expressed.

In one aspect, the present disclosure provides a method for treating or reducing the risk of a TrkB associated conditions in a subject, comprising administering to the subject the TrkB agonist antibody provided herein or the pharmaceutical composition, thereby treating the condition. In certain embodiments, the condition comprises neurodegenerative diseases, psychiatric disorders, metabolic disorders and brain injury. In certain embodiments, the neurodegenerative diseases comprise Alzheimer's disease (AD), Amyotrophic lateral sclerosis (ALS), glaucoma, Huntington's disease (HD), and Parkinson's disease (PD). In certain embodiments, the psychiatric disorders comprise depression, autism, schizophrenia, and post-traumatic stress disorder (PTSD). In certain embodiments, the psychiatric disorders comprise depression, autism, schizophrenia, and post-traumatic stress disorder (PTSD).

In certain embodiments, the TrkB agonist antibody herein is a bispecific antibody, humanized antibody, chimeric antibody, monoclonal antibody, recombinant antibody, labeled antibody, bivalent antibody, or anti-idiotypic antibody. In certain embodiments, the antibody is an antigen-binding fragment selected from the group consisting of a single domain antibody, a camelid single domain antibody, a VNAR, a nanobody, an engineered human VH/VL single domain antibody, a diabody, an scFv, an scFv dimer, a BsFv, a dsFv, a (dsFv)$_2$, a dsFv-dsFv', an Fv fragment, a Fab, a Fab', a F(ab')$_2$, a ds-diabody, a domain antibody, an isolated CDR and a bivalent domain antibody.

In one aspect, the present disclosure provides a method of enhancing cell differentiation and/or synaptic development, comprising contacting the antibody or the pharmaceutical composition provided herein with a biological sample expressing TrkB.

In one aspect, the present disclosure provides a method of enhancing neural injury repairing and/or neurite branching, comprising contacting the antibody or the pharmaceutical composition provided herein with a biological sample expressing TrkB.

In one aspect, the present disclosure provides a method of preventing cell apoptosis and/or necroptosis, comprising contacting the antibody or the pharmaceutical composition provided herein with a biological sample expressing TrkB.

In one aspect, the present disclosure provides a method of enhancing cell survival, comprising contacting the antibody or the pharmaceutical composition provided herein with a biological sample expressing TrkB.

In certain embodiments, the cell is neural cells, including neural stem cells at various differentiation stages or terminally differentiated neural cells, such as neurons, astrocytes and oligodendrocytes. In certain embodiments, neurons are neurons in the central nervous system (CNS). In some embodiments, a biological sample is derived from a cell or tissue (e.g. biopsied tissue from an organ), tumor cells, or bodily fluid (e.g. blood or serum).

In another aspect, the present disclosure provides a method for treating or reducing the risk of a TrkB associated conditions in a subject. In one embodiment, the method comprises administering to the subject a cell, wherein the cell expresses on its cell surface the antibody or the pharmaceutical composition provided herein.

BRIEF DESCRIPTION OF FIGURES

FIG. 2A represents the truncated vector of the five extracellular domains (ECDs) of TrkB; FIG. 2B exemplifies the binding domains for TrkB-agoAb202 and TrkB-agoAb418 measured by immunoprecipitation.

FIGS. 6A-6E show phosphorylation of the kinase signaling pathways MAPK, PI3K and PLCγ via TrkB-agoAbs and BDNF at different concentrations and time periods. FIG. 6A (0.56 nM of TrkB-agoAb101), FIG. 6B (2.3 nM of TrkB-agoAb104), FIG. 6C (0.83 nM of TrkB-agoAb303), FIG. 6D (1.3 nM of TrkB-agoAb203), and FIG. 6E (TrkB-agoAb202 at 0.3 nM, 1 nM, 3 nM and 10 nM).

FIG. 7 illustrates ratio of cell survival in rat hippocampal neurons when treated with Aβ (25-35). FIG. 7A shows the ratio of cell survival in hippocampal neurons being treated with Aβ (25-35) at different concentrations. FIG. 7B shows the rescue percentage of the Aβ (25-35)-treated hippocampal neurons added with either BDNF or the TrkB-AgoAbs.

FIG. 8A shows images of the motor neurons at different culture conditions. FIG. 8B shows reduced apoptosis of TrkB-agoAb101 and TrkB-agoAb202, and FIG. 8C shows reduced apoptosis of TrkB-agoAb202 at different concentrations 1 nM and 3 nM and during different time period of 16 hours and 24 hours, respectively.

FIG. 11A illustrates the fluorescent images of RGCs injected with retrograde labeling marker (4% Fluorogold); FIG. 11B shows alive RGCs counted according to the results of the images.

FIGS. 12A and 12B shows reduced infarct volume of rat brain treated with TrkB-agoAb202 in middle cerebral artery occlusion (MCAO) model. FIG. 12A illustrates exemplary TTC stained rat brain slices treated with either IgG or TrkB-agoAb202. FIG. 12B is a bar chart quantifying the infarct volume based on the TTC stained slices.

FIGS. 13A and 13B show the sensory and motor function recovery in rat stroke model and treated with TrkBagoAb202 in adhesive-removal test. FIG. 13A represents sensory function recovery for the impaired forelimb after 1 mg/kg TrkB-agoAb202 treatment at different time points. FIG. 13B represents motor function recovery for the impaired forelimb after 1 mg/kg TrkB-agoAb202 treatment at different time points.

FIG. 15A shows the relative phosphorylation of MLKL in the lesioned cortical tissue of animals 24 h post MCAO reperfusion. FIG. 15B shows the relative phosphorylation of MLKL in the lesioned cortical tissue of animals 72 h post permanent MCAO.

FIG. 16 shows sequences provided in the present disclosure.

FIG. 17A shows the total length of neurites, and FIG. 17B shows the number of branch points of neurites.

DETAILED DESCRIPTION OF THE INVENTION

Figure 1:
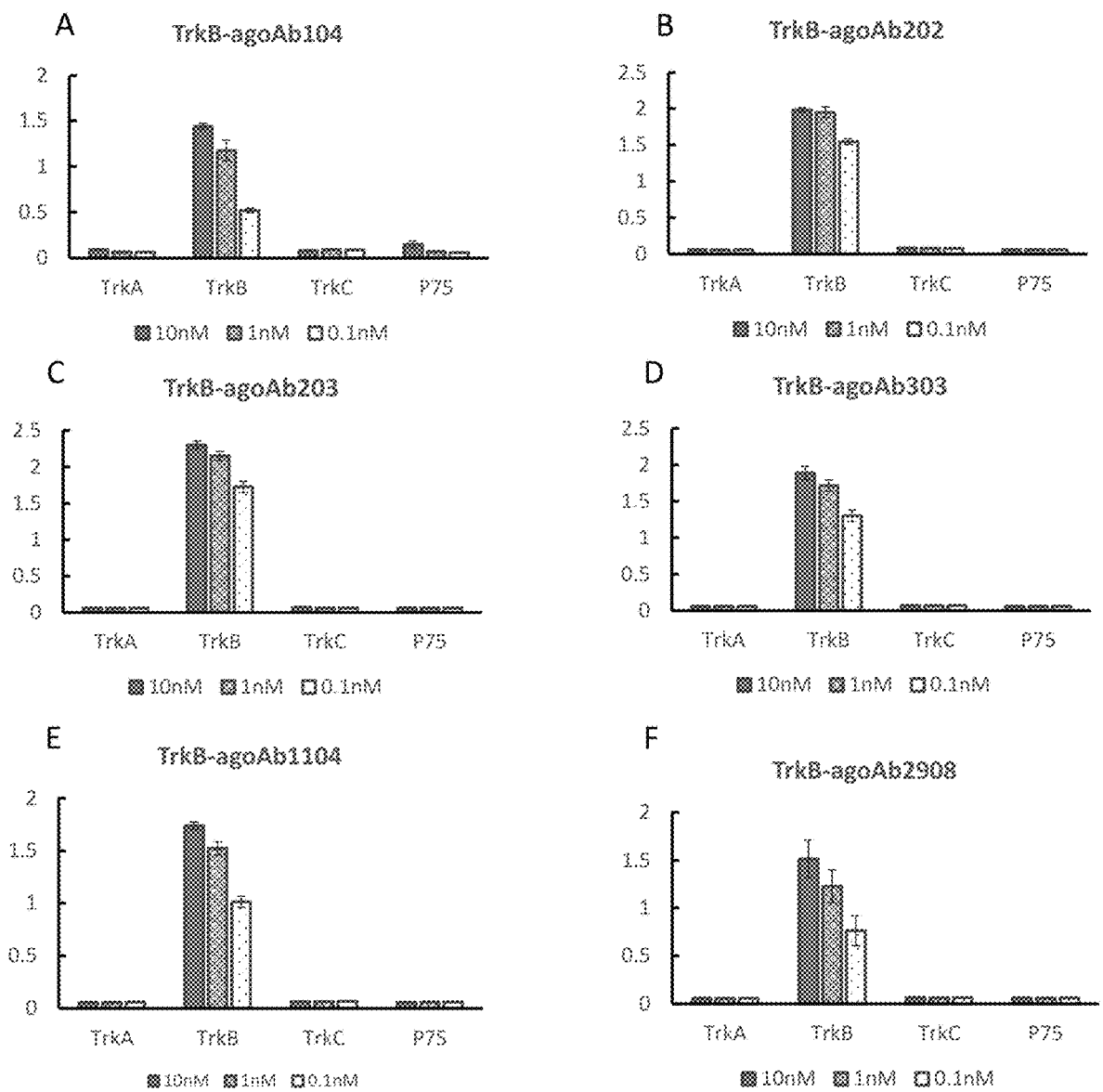
FIGS. 1A-1F are bar charts presenting the antibody specificity to human TrkB as measured by ELISA analysis for TrkB-agoAb104 (FIG. 1A), TrkB-agoAb202 (FIG. 1B), TrkB-agoAb203 (FIG. 1C), TrkB-agoAb303 (FIG. 1D), TrkB-agoAb1104 (FIG. 1E) and TrkB-agoAb2908 (FIG. 1F).

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, multispecific antibody, or bispecific (bivalent) antibody or a functional portion thereof that binds to a specific antigen. A native intact antibody comprises two heavy chains (H) and two light (L) chains inter-connected by disulfide bonds. Each heavy chain consists of a variable region (VH) and a first, second, and third constant region (CH1, CH2 and CH3, respectively), while each light chain consists of a variable region (VL) and a constant region (CL). Mammalian heavy chains are classified as α, δ, ε, γ, and μ, and mammalian light chains are classified as λ or κ. The variable regions of the light and heavy chains are responsible for antigen binding. The variables region in both chains are generally subdivided into three regions of hypervariability called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. Therefore, each VH and VL comprises of three CDRs and four FRs in the following order (amino acid residues N terminus to C terminus): FR1, CDR1, FR2, CDR2, FR3, CDR3, FR4. The constant regions of the heavy and light chains are not involved in antigen binding, but exhibit various effector functions. Antibodies are assigned to the five major classes based on the amino acid sequence of the constant region of their heavy chain: IgA, IgD, IgE, IgG, and IgM, which are characterized by the presence of α, δ, ε, γ, and μ heavy chains, respectively. Subclasses of several of the major antibody classes are such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

As used herein, the term "antigen-binding fragment" refers to an antibody fragment formed from a fragment of an antibody comprising one or more CDRs, or any other antibody portion that binds to an antigen but does not comprise an intact native antibody structure. In certain embodiments, the antibody provided herein is an antigen-binding fragment. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody, a camelid single domain antibody, a VNAR, a nanobody, a domain antibody, an isolated CDR and a bivalent domain antibody. An antigen-binding fragment is capable of binding to the same antigen to which the parent antibody binds. In certain embodiments, an antigen-binding fragment may comprise one or more CDRs from a particular human antibody.

"Fab" with regard to an antibody refers to a monovalent antigen-binding fragment of the antibody consisting of a single light chain (both variable and constant regions) bound to the variable region and first constant region of a single heavy chain by a disulfide bond. Fab can be obtained by papain digestion of an antibody at the residues proximal to the N-terminus of the disulfide bond between the heavy chains of the hinge region.

"Fab'" refers to a Fab fragment that includes a portion of the hinge region, which can be obtained by pepsin digestion of an antibody at the residues proximal to the C-terminus of the disulfide bond between the heavy chains of the hinge region and thus is different from Fab in a small number of residues (including one or more cysteines) in the hinge region.

"F(ab')$_2$" refers to a dimer of Fab' that comprises two light chains and part of two heavy chains.

"Fc" with regard to an antibody refers to that portion of the antibody consisting of the second and third constant regions of a first heavy chain bound to the second and third constant regions of a second heavy chain via disulfide bond. IgG and IgM Fc regions contain three heavy chain constant regions (second, third and fourth heavy chain constant regions in each chain). It can be obtained by papain digestion of an antibody. The Fc portion of the antibody is responsible for various effector functions such as ADCC, and CDC, but does not function in antigen binding.

"Fv" with regard to an antibody refers to the smallest fragment of the antibody to bear the complete antigen binding site. A Fv fragment consists of the variable region of a single light chain bound to the variable region of a single heavy chain. A "dsFv" refers to a disulfide-stabilized Fv fragment that the linkage between the variable region of a single light chain and the variable region of a single heavy chain is a disulfide bond.

"Single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA*, 85:5879(1988)). A "scFv dimer" refers to a single chain comprising two heavy chain variable regions and two light chain variable regions with a linker. In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, a "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

"Single-chain Fv-Fc antibody" or "scFv-Fc" refers to an engineered antibody consisting of a scFv connected to the Fc region of an antibody.

"Single domain antibodies (sdAbs)", such as "camelid single domain antibody," "heavy chain antibody," "nanobody", "HCAb" or "VNAR" refers to an antibody that contains two $V_H$ domains and no light chains with a low molecular weight of 12-15 kDa (Riechmann L. and Muyldermans S., *J Immunol Methods*. December 10; 231(1-2): 25-38 (1999); Muyldermans S., *J Biotechnol. June;* 74(4): 277-302 (2001); WO94/04678; WO94/25591; U.S. Pat. No. 6,005,079). Heavy chain antibodies were originally obtained from Camelidae (camels, dromedaries, and llamas, VHH), from shark species (variable domain of the new antigen receptors (VNAR)), or from human antibodies with specific following mutations: F37, E44, R45, and F47. Human VH/VL single domain antibodies can be isolated from engineered antibody domain libraries by phage display constructed via synthetic randomization of rearranged VH/VL domains (Henry K A et al., Stability-Diversity Tradeoffs Impose Fundamental Constraints on Selection of Synthetic Human VH/VL Single-Domain Antibodies from In Vitro Display Libraries. Front Immunol. 2017 Dec. 12; 8:1759). Single domain antibody thus contains at least 4 framework regions interspaced by 3 hypervariable CDR regions, resulting in the following typical antibody variable domain structure: FR1-CDR1-FR2-CDR2-FR3-CDR3-FR4. The single domain does not interact with light chain antibody variable region to form conventional heterodimer of heavy and light chains antigen-binding VII structure.

"Diabodies" include small antibody fragments with two antigen-binding sites, wherein the fragments comprise a $V_H$ domain connected to a $V_L$ domain in a single polypeptide chain ($V_H$-$V_L$ or $V_L$-$V_H$) (see, e.g., Holliger P. et al., *Proc Natl Acad Sci USA. July* 15; 90(14):6444-8 (1993); EP404097; WO93/11161). The two domains on the same chain cannot be paired, because the linker is too short, thus, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain embodiments, two or more $V_H$ domains are covalently joined with a peptide linker to form a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or "dsFv-dsFv'" comprises three peptide chains: a $V_{H1}$-$V_{H2}$ moiety wherein the heavy chains are bound by a peptide linker (e.g., a long flexible linker) and paired via disulfide bridges to $V_{L1}$ and $V_{L2}$ moieties, respectively. Each disulfide paired heavy and light chain has a different antigen specificity.

The term "humanized" or "humanized version" as used herein, with reference to antibody or antigen-binding fragment, refers to the antibody or the antigen-binding fragment comprises CDRs derived from non-human animals (e.g. a rodent, rabbit, dog, goat, horse, or chicken), FR regions derived from human, and when applicable, the constant regions derived from human. In certain embodiments, the constant regions from a human antibody are fused to the non-human variable regions. A humanized antibody or antigen-binding fragment is useful as human therapeutics. In certain embodiments because it has reduced immunogenicity or is less likely to induce an immune response in human, as compared to the non-human species antibody. In some embodiments, the non-human animal is a mammal, for example, a mouse, a rat, a rabbit, a goat, a sheep, a cattle, a horse, a guinea pig, a hamster, or a non-human primate (for example, a monkey (e.g., cynomolgus or rhesus monkey) or ape (e.g., chimpanzee, gorilla, simian or affen)). In some embodiments, the humanized antibody or antigen-binding fragment is composed of substantially all human sequences except for the CDR sequences which are non-human. In some embodiments, the humanized antibody or antigen-binding fragment is modified to improve the antibody performance, such as binding or binding affinity. For example, one or more amino acid residues in one or more non-human CDRs are altered to reduce potential immunogenicity in human, wherein the altered amino acid residues either are not critical for immunospecific binding or the alterations are conservative changes, such that the binding of the humanized antibody to the antigen is not significantly affected. In some embodiments, the FR regions derived from human may comprise the same amino acid sequence as the human antibody from which it is derived, or it may comprise some amino acid changes, for example, no more than 10, 9, 8, 7, 6, 5, 4, 3, 2, or 1 changes of amino acid. In some embodiments, such change in amino acid could be present in heavy chain FR regions only, in light chain FR regions only, or in both chains. In some preferable embodiments, the humanized antibodies comprise human FR1-3 and human JH and Jκ.

The term "chimeric" as used herein refers to an antibody or antigen-binding fragment that has a portion of heavy and/or light chain derived from one species, and the rest of the heavy and/or light chain derived from a different species. In an illustrative example, a chimeric antibody may comprise a constant region derived from human and a variable region derived from a non-human species, such as from mouse.

"TrkB agonist antibody" or "TrkB-AgoAb" as used herein refers to an antibody that is capable of specific binding to one of the extracellular domains or the juxtamembrane domain of TrkB (e.g. human or non-human TrkB) with an affinity which is sufficient to provide for diagnostic and/or therapeutic use and thereby activating the intracellular activity of TrkB, activates the BDNF intracellular signal transduction pathway, upregulates expression or availability of TrkB, or upregulates expression or availability of genes regulated by TrkB-mediated BDNF signaling in a cell or organism.

"Substantially", "substantially the same" as used herein refer to a high degree of similarity between two numeric values, and those skilled in the art would not recognize or consider a significant difference between the two values or of little difference with regard to statistics and/or biological activity as indicated by the values. In contrast, "substantially lower" means that a numeric value is less than about 50%, less than about 40%, less than about 30%, less than about 20%, less than about 10% as a function of the reference value.

The term "specific binding" or "specifically binds" as used herein refers to a non-random binding reaction between two molecules, such as for example between an antibody and an antigen. In certain embodiments, the antibodies or antigen-binding fragments provided herein specifically bind human and/or non-human TrkB with a binding affinity ($K_D$) of about 0.01 nM to about 100 nM, about 0.1 nM to about 100 nM, 0.01 nM to about 10 nM, about 0.1 nM to about 10 nM, 0.01 nM to about 5 nM, about 0.1 nM to about 5 nM, 0.01 nM to about 1 nM, about 0.1 nM to about 1 nM or about 0.01 nM to about 0.1 nM). $K_D$ as used herein refers to the ratio of the dissociation rate to the association rate ($k_{off}/k_{on}$), may be determined using surface plasmon resonance methods for example using instrument such as Biacore.

The ability to "block binding" or "compete for the same epitope" as used herein refers to the ability of an antibody or antigen-binding fragment to inhibit the binding interaction between two molecules (e.g. human TrkB and a TrkB agonist antibody) to any detectable degree. In certain embodiments, an antibody or antigen-binding fragment that blocks binding between two molecules inhibits the binding interaction between the two molecules by at least 50%. In certain embodiments, this inhibition may be greater than 60%, greater than 70%, greater than 80%, or greater than 90%.

The term "epitope" as used herein refers to the specific group of atoms (e.g. sugar side chains, phosphoryl groups, sulfonyl groups) or amino acids on an antigen bound by an antigen binding protein, such as an antibody. An epitope can be conformational or linear. In certain embodiments, the epitope contained in one of the extracellular domain of TrkB can be conformational or linear. A conformational epitope can comprise non-contiguous but spatially juxtaposed amino acid residues due to the three dimensional tertiary folding of a protein, wherein those residues directly contribute to the affinity of the interaction and will lose the ability of interaction when exposed to denaturing solvents. In contrast, all the points of interaction of a linear epitope are arranged linearly along the primary amino acid residues on the protein and the small segments of the contiguous amino acids can be digested from an antigen binding with major histocompatibility complex (MHC) molecules or retained on exposure to denaturing solvents (Salmerón A et al., *J Immunol.* 1991 Nov. 1; 147(9):3047-52; Goldsby et al., *Immunology*(Fifth ed.). New York: W. H. Freeman and Company. pp. 57-75. ISBN 0-7167-4947-5). In one embodiments of the present disclosure, the epitopes bound by the TrkB antibodies provided herein is conformational. In another embodiments of the present disclosure, the epitopes bound by the TrkB antibodies provided herein is linear. Two antibodies may bind the same epitope within an antigen if they exhibit competitive binding for the antigen. For example, if an antibody or antigen-binding fragment blocks binding of the exemplary antibodies of the present disclosure, such as TrkB-agoAb202, TrkB-agoAb303, TrkB-agoAb203, TrkB-agoAb104, TrkB-agoAb1104, TrkB-agoAb2908, TrkB-agoAb5702, TrkB-agoAb1016, TrkB-agoAb2037, TrkB-agoAbB901, TrkB-agoAbB503, TrkB-agoAbB418, TrkB-agoAb6916, TrkB-agoAb4014, and TrkB-agoAb7431, chimeric antibodies thereof, humanized antibodies thereof, to human or non-human TrkB, then the antibody or antigen-binding fragment may be considered to bind the same epitope as those exemplary antibodies.

A particular amino acid residue within the epitope can be mutated, e.g. by alanine scanning mutagenesis, and mutations that reduce or prevent protein binding are identified. An "alanine scanning mutagenesis" is a method that can be performed for identifying certain residues or regions of a protein that affect the interaction of the epitope with another compound or protein that binds to it. A residue or group of target residues within the protein is replaced by a neutral or negatively charged amino acid (most preferably alanine or polyalanine, or a conservative amino acid substitution). Any mutation of the amino acid residues or codons encoding the same that reduces binding of the protein more than a threshold or reduces binding of the protein to the maximal degree than other mutations is likely to be within the epitope bound by the protein.

The sequences described below can be found in FIG. 16.

"TrkB-agoAb202" as used herein refers to a rabbit monoclonal antibody having three heavy chain variable region CDRs of SEQ ID NO: 12 (CDR1), SEQ ID NO: 13 (CDR2), SEQ ID NO: 14 (CDR3), three light chain variable region CDRs of SEQ ID NO: 9 (CDR1), SEQ ID NO: 10 (CDR2), SEQ ID NO: 11 (CDR3). TrkB-agoAb202 binds to D1 domain of the TrkB protein.

"TrkB-agoAb303" as used herein refers to a mouse monoclonal antibody having three heavy chain variable region CDRs of SEQ ID NO: 18 (CDR1), SEQ ID NO: 19 (CDR2), SEQ ID NO: 20 (CDR3), three light chain variable region CDRs of SEQ ID NO: 15 (CDR1), SEQ ID NO: 16 (CDR2), SEQ ID NO: 17 (CDR3), with a heavy chain variable region of SEQ ID NO: 28 and a light chain variable region of SEQ ID NO: 27. TrkB-agoAb303 binds to D3 domain of the TrkB protein.

"TrkB-agoAb203" as used herein refers to a rabbit monoclonal antibody having three heavy chain variable region CDRs of SEQ ID NO: 24 (CDR1), SEQ ID NO: 25 (CDR2), SEQ ID NO: 26 (CDR3), three light chain variable region CDRs of SEQ ID NO: 21 (CDR1), SEQ ID NO: 22 (CDR2), SEQ ID NO: 23 (CDR3). TrkB-agoAb203 binds to D5 domain of the TrkB protein.

"TrkB-agoAb2908" as used herein refers to a mouse monoclonal antibody having three heavy chain variable region CDRs of SEQ ID NO: 32 (CDR1), SEQ ID NO: 33 (CDR2), SEQ ID NO: 34 (CDR3), three light chain variable region CDRs of SEQ ID NO: 29 (CDR1), SEQ ID NO: 30 (CDR2), SEQ ID NO: 31 (CDR3), with a heavy chain variable region of SEQ ID NO: 36 and a light chain variable region of SEQ ID NO: 35. TrkB-agoAb2908 binds to D5 domain of the TrkB protein.

"TrkB-agoAb1104" as used herein refers to a mouse monoclonal antibody having three heavy chain variable region CDRs of SEQ ID NO: 40 (CDR1), SEQ ID NO: 41 (CDR2), SEQ ID NO: 42 (CDR3), three light chain variable region CDRs of SEQ ID NO: 37 (CDR1), SEQ ID NO: 38 (CDR2), SEQ ID NO: 39 (CDR3), with a heavy chain variable region of SEQ ID NO: 44 and a light chain variable region of SEQ ID NO: 43. TrkB-agoAb1104 binds to D1 domain of the TrkB protein.

"TrkB-agoAbB901" as used herein refers to a mouse monoclonal antibody having three heavy chain variable region CDRs of SEQ ID NO: 48 (CDR1), SEQ ID NO: 49 (CDR2), SEQ ID NO: 50 (CDR3), three light chain variable region CDRs of SEQ ID NO: 45 (CDR1), SEQ ID NO: 46 (CDR2), SEQ ID NO: 47 (CDR3), with a heavy chain variable region of SEQ ID NO: 52 and a light chain variable region of SEQ ID NO: 51. TrkB-agoAbB901 binds to D5 domain of the TrkB protein.

"TrkB-agoAb5702" as used herein refers to a mouse monoclonal antibody having three heavy chain variable region CDRs of SEQ ID NO: 56 (CDR1), SEQ ID NO: 57 (CDR2), SEQ ID NO: 58 (CDR3), three light chain variable region CDRs of SEQ ID NO: 53 (CDR1), SEQ ID NO: 54 (CDR2), SEQ ID NO: 55 (CDR3), with a heavy chain variable region of SEQ ID NO: 60 and a light chain variable region of SEQ ID NO: 59. TrkB-agoAb5702 binds to D5 domain of the TrkB protein.

"TrkB-agoAb6916" as used herein refers to a mouse monoclonal antibody having three heavy chain variable region CDRs of SEQ ID NO: 64 (CDR1), SEQ ID NO: 65 (CDR2), SEQ ID NO: 66 (CDR3), three light chain variable region CDRs of SEQ ID NO: 61 (CDR1), SEQ ID NO: 62 (CDR2), SEQ ID NO: 63 (CDR3), with a heavy chain variable region of SEQ ID NO: 68 and a light chain variable region of SEQ ID NO: 67. TrkB-agoAb6916 binds to D5 domain of the TrkB protein.

"TrkB-agoAb7431" as used herein refers to a mouse monoclonal antibody having three heavy chain variable region CDRs of SEQ ID NO: 72 (CDR1), SEQ ID NO: 73 (CDR2), SEQ ID NO: 74 (CDR3), three light chain variable region CDRs of SEQ ID NO: 69 (CDR1), SEQ ID NO: 70 (CDR2), SEQ ID NO: 71 (CDR3), with a heavy chain variable region of SEQ ID NO: 76 and a light chain variable region of SEQ ID NO: 75. TrkB-agoAb7431 binds to juxtamembrane region of the TrkB protein.

A "conservative substitution" with reference to amino acid sequence refers to replacing an amino acid residue with a different amino acid residue having a side chain with similar physiochemical properties or substitution of those amino acids that are not critical to the activity of the polypeptide. For example, conservative substitutions can be made among amino acid residues with nonpolar side chains (e.g. Met, Ala, Val, Leu, and Ile, Pro, Phe, Trp), among residues with uncharged polar side chains (e.g. Cys, Ser, Thr, Asn, Gly and Gln), among residues with acidic side chains (e.g. Asp, Glu), among amino acids with basic side chains (e.g. His, Lys, and Arg), among amino acids with beta-branched side chains (e.g., Thr, Val and Ile), among amino acids with sulfur-containing side chains (e.g.,Cys and Met), or among residues with aromatic side chains (e.g. Trp, Tyr, His and Phe). In certain embodiments, substitutions, deletions or additions can also be considered as "conservative substitution". The number of amino acids that are inserted or deleted can be in the range of about 1 to 5. As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum correspondence. Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

As used herein, a "homologue sequence" and "homologous sequence" are used interchangeable and refer to polynucleotide sequences (or its complementary strand) or amino acid sequences that have sequences identity of at least 80% (e.g. at least 85%, 88%, 90%, 91%, 92%, 93%, 94%, 95%, 96%, 97%, 98%, 99%) to another sequences when optionally aligned.

"Effector functions" or "antibody effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis. "Reduce or deplete effector functions" refers to the antibody effector function is reduced by at least 50% (e.g. 60%, 70%, 80%, 90%, 95%, 96%, 97%, 98%, 99%) from the parent antibody. In certain embodiments, the effector function is eliminated through a mutation in the Fc region to eliminate glycosylation, e.g. N297A or D265A (see Shields et al., *J. Biol. Chem.* 276 (9): 6591-6604 (2001)), K322A, L234A/L235A. "Fc region" as used herein refers to a C-terminal region of an immunoglobulin heavy chain.

"Treating", "treatment" or "therapy" of a condition as used herein can be used interchangeably, and includes therapeutic treatment, prophylactic or preventative measures, such as preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "TrkB" as used herein refers to the tropomyosin receptor kinase B (TrkB), also known as tyrosine receptor kinase B, or BDNF/NT-3 growth factors receptor or neurotrophic tyrosine kinase receptor type 2, which is a protein that in humans is encoded by the NTRK2 gene. TrkB is located at the cellular membrane and is activated by binding of a ligand to the receptor's extracellular domain. TrkB has three isoforms in mammalian central nervous system (CNS): the full-length isoform is a typical tyrosine kinase receptor, while the two C-terminal TrkB isoforms having the same extracellular domain, transmembrane domain and first 12 intracellular amino acid sequences as the full-length isoform but differing at the C-terminal sequences with 11 (T1 isoform) and 9 (T2 isoform) amino acids, respectively. In the present disclosure, the TrkB protein refers to either of the above mentioned three isoforms. TrkB is a receptor for brain-derived neurotrophic factor (BDNF) and binds BDNF in a ligand-specific manner. BDNF binding to TrkB triggers its dimerization through conformational changes and autophosphorylation of tyrosine residues in its intracellular domain, resulting in activation of the three major signaling pathways involving mitogen-activated protein kinase (MAPK), phosphatidylinositol 3-kinase (PI3K) and phospholipase C-gamma 1 (PLC-gamma 1). Several neurotrophins that are reported to activate TrkB, such as BDNF, neurotrophin-4 (NT-4) and neurotrophin-3 (NT-3), thereby activating the multiple effects includes neuronal differentiation, neuronal repair, neuronal plasticity, proliferation and survival. Both BDNF and NT-4 can bind to TrkB and can activate many common signalling pathways. In certain embodiments, the TrkB as used herein is a human TrkB with the gene sequence with accession No. S76473.1, or a non-human animal TrkB, such as a mouse TrkB, a rat TrkB, a rabbit TrkB.

The term "truncated TrkB" as used herein refers to a TrkB protein that lacks partial fragments (such as the extracellular domains) but remains the main function of a TrkB receptor in intracellular signaling. In certain embodiments, the truncated TrkB lacks D1-D5 domains and has the sequence as set forth in SEQ ID NO: 8.

"BDNF" is encoded by the BDNF gene in humans and is a member of the neurotrophin family of growth factors, which are related to the canonical Nerve Growth Factor. BDNF are found in the brain such as the hippocampus, cortex, and basal forebrain, mediating survival and differentiative activities on neurons and modulating the synaptic function of neurons by binding and activating TrkB, as well as in the periphery nervous system, such as the retina, motor neurons, the kidneys, saliva, and the prostate. BDNF binds at least two receptors on the surface of cells, such as TrkB and p75 (also known as LNGFR). All neurotrophins can interact with the p75 receptor. When the p75 is activated, it triggers apoptosis rather than survival pathways in cells expressing p75 receptor but lacking Trk receptors. BDNF also binds TrkA and TrkC, which together with TrkB belong to a sub-family of protein kinases. "Pro-BDNF" refers to uncleaved precursor of BDNF that consists of a prodomain of 129 amino acids and a mature domain of 118 amino acids. When the prodomain is cleaved from intact pro-BDNF, through the actions of proconvertase at a conserved RVRR sequence, the dimeric mature domains are released, and are called mature BDNF, or simply BDNF. It is reported that the p75 receptor binds to the mature domain region of pro-BDNF and induces opposite effects of those elicited by mature BDNF, such as cell death, retraction of growth cones, facilitation of long-term depression at mature hippocampal synapses and synaptic elimination of the neuromuscular junction (Hempstead B L, Trans Am Clin Climatol Assoc. 2015; 126:9-19). In certain embodiments, the BDNF as used in the present disclosure refers to the mature BDNF. In certain embodiments, the TrkB agonist antibody provided herein binds to mature BDNF and does not bind to pro-BDNF.

Neurotrophin-4 (NT-4), also known as neurotrophin-5 (NT-5), is a neurotrophic factor that signals predominantly through the TrkB receptor. In humans, NT-4 is encoded by NTF4 gene. NT-4 is involved in the control of survival and differentiation of neurons. While knock-outs of other neurotrophins including NGF, BDNF, and NT-3 are lethal during early postnatal development, NTF5-deficient mice only show minor cellular deficits and develop normally to adulthood, suggesting that it's function can be compensated by other neurotrophins.

A "TrkB associated condition" as used herein refers to any condition that is caused by, exacerbated by, or otherwise linked to increased or decreased expression or activities of TrkB (e.g. a human TrkB), or a disorder that is caused or exacerbated by a decrease in BDNF signaling, or any other intracellular signaling cascade that is activated through TrkB. Examples of neurological and psychiatric disorders include neurodegenerative diseases (includes but are not limited to Alzheimer's Disease and related dementias, Parkinson's Disease, Huntington's Disease, Lewy Body Disease and related movement disorders, Amyotrophic lateral sclerosis, glaucoma and Friedrich's Ataxia and related Spinocerebellar Ataxia's), depression, anxiety, autism, schizophrenia, and post-traumatic stress disorder, CNS injuries, stroke and traumatic brain injury, and the like. Examples of metabolic disorders include obesity and hyperphagia. "Cancer" or "cancerous condition" as used herein refers to any medical condition characterized by malignant cell growth or neoplasm, abnormal proliferation, infiltration or metastasis, and includes both solid tumor cancers and non-solid cancers (hematologic malignancies) such as leukemia. Solid tumors include sarcomas and carcinomas. Sarcomas are non-epithelial tumors in a blood vessel, bone, fat tissue, ligament, lymph vessels, muscle or tendon, whereas carcinomas are epithelial tumors in the skin, glands and the linings of organs. "Tumor" as used herein refers to a solid mass of neoplastic and/or malignant cells.

An "isolated" substance has been altered by the hand of man from the natural state. If an "isolated" composition or substance occurs in nature, it has been changed or removed from its original environment, or both. For example, an "isolated" polynucleotide or polypeptide is a polynucleotide or a polypeptide that is free of other polynucleotides or polypeptides, respectively, and is not associated with naturally components that accompany the polynucleotide or a polypeptide in the native state. In certain embodiments, an "isolated" antibody is purified by at least one step to a purity of at least 90%, 91%, 92%, 93%, 94%, 95%, 96%, 97%, 98%, 99% as determined by electrophoretic methods (such as SDS-PAGE using Coomassie blue or silver stain, isoelectric focusing, capillary electrophoresis), chromatographic methods (such as ion exchange chromatography or reverse phase HPLC) or Lowry method.

The term "vector" as used herein refers to a vehicle into which a polynucleotide encoding a protein may be operably inserted and transported so as to express that protein in a host cell. A vector may be used to transform, transduce, or transfect a host cell so as to bring about the expression of the genetic element it carries within the host cell. Exemplary types of vectors include, but not limited to, plasmids (e.g. phagemids, cosmids, yeast artificial chromosome (YAC), bacterial artificial chromosome (BAC) or P1-derived artificial chromosome (PAC)), viral vector (bacteriophages such as lambda phage or M13 phage, or animal viruses), bacterial vector, or non-episomal mammalian vectors. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector (e.g. a bacterial vector or episomal mammalian vector) may contain an origin of replication. A vector may also include materials to aid in its entry into the cell, including but not limited to a viral particle, a liposome, or a protein coating.

The "host cell" as used herein refers to a cell into which an exogenous polynucleotide and/or a vector has been introduced to express one or more exogenous proteins. It intends to refer to both the particular subject cell and the progeny thereof. A host cell can be a prokaryote, a eukaryote, a plant cell, an animal cell or a hybridoma. It can be a cell that does not express a protein at a desired level but comprises the nucleic acid, unless a regulatory agent is introduced into the cell or a regulatory sequence is introduced into the host cell so that it is operably linked with the nucleic acid.

A "pharmaceutical composition" refers to a mixture of one or more of the compounds described herein, or pharmaceutically acceptable salts thereof, with other chemical components, such as physiologically acceptable carriers and excipients in the form of pills, tablets, capsules, or liquid formulations for injection by needle or similar apparatus. One purpose of a pharmaceutical composition is to facilitate administration of a compound to an organism. It is not intended to be limited to those compositions approved by a regulatory agency and intended to encompass nutritional supplements and other formulations.

The term "therapeutically effective amount" or "effective dosage" as used herein refers to the dosage or concentration of a drug effective to treat a disease or condition associated with human TrkB. For example, with regard to the use of the antibodies or antigen-binding fragments disclosed herein to treat cancer, a therapeutically effective amount is the dosage or concentration of the antibody or antigen-binding fragment capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

The term "pharmaceutically acceptable" indicates that the designated carrier, vehicle, diluent, excipient(s), and/or salt are generally chemically and/or physically compatible with the other ingredients comprising the formulation, and physiologically compatible with the recipient thereof. An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Cell differentiation" as used herein is the development, from a cell type, into a different cell type. For instant, a bipotent, pluripotent or totipotent cell may differentiate into a neural cell. Differentiation may be accompanied by proliferation, or may be independent thereof "Differentiation" generally refers to the acquisition of a phenotype of a mature cell type from a less developmentally defined cell type, e.g. a neuron, or a lymphocyte, but does not preclude transdifferentiation, whereby one mature cell type may convert to another mature cell type, e.g. a neuron to a lymphocyte.

BDNF/NT-4-TrkB Signaling Pathway

Members of neurotrophin family are highly homologous dimeric growth factors and include nerve growth factor (NGF), brain-derived neurotrophic factor (BDNF), neurotrophin-3 (NT-3), neurotrophin-4/5 (NT-4/5), etc (McAllister et al., 1999). Neurotrophins have diverse functions. During the synthetic process of neurotrophins in cells, initially synthesized as precursors (proneurotrophins), they are cleaved to produce mature neurotrophins, which promote neuronal survival and enhance synaptic plasticity by activating Trk receptor tyrosine kinases (Nagappan and Lu, 2005). Proneurotrophins tend to bind with p75NTR (p75 neurotrophic factor receptor, p75NTR), which causes cell apoptosis (Woo et al., 2005). Like all other tyrosine kinase receptors, through dimerization, the Trk receptors are activated, leading to the autophosphorylation of intracellular tyrosine residues and triggering of the signal transduction cascade. The signal transduction pathways activated by Trks include Ras/extracellular regulated kinase (Erk) pathway, Phosphatidylinositol-3 kinase (PI3 kinase)/Akt pathway and PLCγ/PKC pathway (Huang and Reichardt, 2001; Kaplan and Miller, 2000).

Among the neurotrophin receptors, TrkB and its endogenous ligand BDNF/NT-4 receive much concern for their regulating synaptic plasticity. Neurotrophins exist as stable dimers linked by noncovalent bond. The dimerized Ligand draws receptor monomers together, inducing receptor dimerization and phosphorylation of tyrosine residues of the receptor. Then the auto-phosphorylation of receptors activates signaling cascades (Ibanez et al., 1993; McDonald et al., 1991; Radziejewski et al., 1992). TrkB is composed by the extracellular domain including five domains, a transmembrane region and the intracellular kinase domain. The first three extracellular domains D1-D3 consist of a leucine-rich region flanked by two cysteine-rich regions. Both domain 4 and 5 (D4, D5) are immunoglobulin-like domains. Crystallography research data indicates that D5 is the region where BDNF bind to TrkB (Banfield et al., 2001). Ligand binding induces receptor dimerization and phosphorylation of 5 tyrosine residues Tyr515, Tyr701, Tyr705, Tyr706 and Tyr816 in the intracellular kinase domain of the receptor (McCarty and Feinstein, 1998). Phosphorylation of the tyrosine at position 515 in the intracellular juxta-membrane region recruits Shc adaptor molecules through their phosphotyrosine-binding (PTB) domains (Easton et al., 1999). TrkB cannot interact with Shc if Tyr515 of TrkB is replaced by F (Easton et al., 1999). The position 816 is also phosphorylated in C terminal of TrkB, which causes phospholipase C-γ (PLC-γ) to bind to positon 816 through a Src-homology 2 (SH2) domain and to be phosphorylated (McCarty and Feinstein, 1998).

The downstream are three main intracellular signaling cascades: the Ras-mitogen-activated protein kinase (MAPK) pathway, the phosphatidylinositol 3-kinase (PI3K)-Akt pathway and the PLCγ-$Ca^{2+}$ pathway. TrkB regulates neuron differentiation and synaptic development through MAPK pathway (Cowley et al., 1994). Recruitment and phosphorylation of Shc adaptors at Tyr515 leads to the binding of growth factor receptor-bound protein 2 (GRB2) and son of sevenless (SOS), activating the Ras-MAPK downstream pathways including c-Raf/B-Raf/Erk1/Erk2/p38MAPK, etc (Ballif and Blenis, 2001). TrkB regulates cell development and survival through PI3K-Akt pathway, and promotes dendritic spines growing with Akt as the center. The association and activation between PI3K and TrkB are indirectly, which are through the recruited GRB-associated binder-1 (GAB1), insulin-receptor substrate 1 (IRS1) and IRS2 to activate PI3K. In response to this association, 3-phosphoinositieds are generated by PI3K and activate 3-phosphoinosite-dependent protein kinase 1 (PDPK1). With these 3-phosphoinositides, PDPK1 activates the protein kinase Akt, which phosphorylated several proteins including caspase-9, glycogen synthase kinase-3 (GSK-3) and FKHR family members, etc (van Weeren et al., 1998).

Lowering the activating level of TrkB signaling pathway can significantly impair axons and branches of dendritic spines. The scaffold proteins ARMS and RhoA are involved in this process (Lin et al., 2011). PLCγ pathway begins with the phosphorylation of Tyr816 in TrkB. PLCγ pathway mainly recruits diacylglycerol (DAG) and inositol triphosphate (IP3) (Gupta et al., 2013). DAG can activate protein kinase C (PKC), and IP3 causes calcium influx. They coordinate to regulate neurite branching. However, gene knockout at Tyr816 cannot thoroughly block neurite branch, which indicates that other signaling pathways may also participate in this process.

TrkB Agonist Antibody

Although the activation of TrkB signaling pathway by BDNF has neurotrophic function, BDNF has some affinity for p75NTR at the same time. Activation of that receptor will lead to activation of downstream factors including JNK, and will cause cytotoxicity, which can induce cell death. In addition, the biochemical nature of BDNF itself is very unstable. Its half-life in plasma is only about 10 minutes. In terms of industrial production, the preparation of BDNF is quite expensive. Therefore, according to the mechanism that the BDNF dimer mediate dimerization and autophosphorylation of its receptors, antibody molecules (mainly IgG) can achieve similar activation because they are also bivalent (having 2 same Fab domains). In 1996, Lucidi-Phillipi et al. first reported that anti-TrkA polyclonal antibody could activate TrkA and inhibit the death of cholinergic neurons in animals (Lucidi-Phillipi et al., 1996). In the same year, LeSauteur reported a monoclonal antibody of TrkA. This anti-human TrkA antibody recognizes the NGF-docking site, binding and activating TrkA and its downstream molecule PI3-K (LeSauteur et al., 1996). Qian et al. first reported the development of TrkB antibody agonists. Among the five monoclonal antibodies screened by investigators, the sites where TrkB binds to each antibody were different, but all of them could promote cell survival and neurite outgrowth in different degrees. More importantly, these antibodies do not activate p75NTR (Qian et al., 2006). As one of these antibodies, 29D7 has been found to have therapeutic effects in a variety of neurological diseases. Katsuki found that putting 29D7 in vitreous could reduce retinal ganglion cell death in the surgery of optic nerve damage (Hu et al., 2010). After the hypoxia ischemic surgery for neonatal rats, 29D7 can reduce cell death and promote the long-term recovery of sensorimotor function, which is significant to clinical treatment for children with cerebral palsy (the Kim et al., 2014). In addition, Todd proved that 29D7 could reduce the impairment of striatal cell caused by mutant huntingtin protein (Todd et al., 2014), for which reason it becomes a potential drug in treatment of Huntington's disease.

The present disclosure in one aspect provides TrkB agonist antibodies and the antigen-binding fragments thereof. In certain embodiments, the present disclosure provides exemplary monoclonal antibodies TrkB-agoAb202, TrkB-agoAb303, TrkB-agoAb203, TrkB-agoAb104, TrkB-agoAb1104, TrkB-agoAb2908, TrkB-agoAb5702, TrkB-agoAb1016, TrkB-agoAb2037, TrkB-agoAbB901, TrkB-agoAbB503, TrkB-agoAbB418, TrkB-agoAb6916, TrkB-agoAb4014, TrkB-agoAb7431, chimeric antibodies thereof, and humanized antibodies thereof.

A skilled artisan will understand that the CDR sequences provided herein can be modified (or using the term "modification") to contain one or more substitutions (or insertion or deletion) of amino acid residues, such that the resulting antibody is improved in one or more properties (such as improved binding or binding affinity, increased pharmacokinetic half-life, pH sensitivity, compatibility to conjugation reduced risk of glycosylation and/or deamination on a CDR residue, and reduced immunogenicity), and is otherwise comparable to the parent antibody (i.e. antibody having otherwise the same set of CDR sequences except for the above-mentioned modification or change), or at least substantially retains the antigen-binding property of the parent antibody. For example, a library (or a repertoire) of antibody variants (such as Fab or scFv variants) can be generated and expressed with phage display technology, and then screened for the binding or binding affinity to human TrkB. For another example, computer software can be used to virtually simulate the binding of the antibodies to human TrkB, and identify the amino acid residues on the antibodies which form the binding interface. Such residues may be either avoided in the substitution so as to prevent reduction in binding or binding affinity, or targeted for substitution to provide for a stronger binding. In certain embodiments, at least one (or all) of the substitution(s) in the CDR sequences is conservative substitution.

In certain embodiments, the antibodies and the antigen-binding fragments thereof comprise one or more CDR sequences having at least 80% (e.g. at least 85%, 88%, 90%, 91%, 92%, 93%, 94%, 95%, 96%, 97%, 98%, 99%) sequence identity to that (or those) provided herein, and in the meantime retain the binding activity or binding affinity to human TrkB at a level similar to or even higher than its parental antibody having substantially the same sequence except that the corresponding CDR sequence is in 100% sequence identity to that (or those) provided herein.

In certain embodiments, the TrkB agonist antibodies and the antigen-binding fragments thereof are chimeric. The chimeric antibody contains one or more regions from an antibody and one or more regions from other antibodies or species. In certain embodiments, at least one CDR of the chimeric TrkB agonist antibody is derived from one species. In certain embodiments, all of the CDRs are derived from another species. In certain embodiments, a variable region of the chimeric TrkB agonist antibody is derived from one species and is linked to a constant region of an antibody of another species. The chimeric antibody retains the binding activity or binding affinity of the parent antibody.

In certain embodiments, the TrkB agonist antibodies and the antigen-binding fragments thereof are humanized. In certain embodiments, the humanized antibody originated from non-human species, and several amino acid residues in the framework and constant regions of the heavy and light chains have been mutated to reduce or avoid an immunogenicity in humans. In certain embodiments, the variable regions of a non-human species is fused to the constant regions of a human antibody. In certain embodiments, the humanized antibody is created by CDR grafting, i.e. replacing the CDR of a human antibody with the corresponding CDR of a non-human antibody. Thus, the immunogenicity of the humanized antibody in human is low. In certain embodiments, the human framework regions are substituted with one or more amino acid residues from the non-human antibody (e.g. mouse framework region) from which the CDR sequences are derived, for example, to improve or retain the binding activity or binding affinity. In certain embodiments, the humanized antibody retains or increases the binding activity or binding affinity of the parent antibody.

In some embodiments, the binding affinity can be represented by $K_D$ value, which is calculated as the ratio of dissociation rate to association rate ($k_{off}/k_{on}$) when the binding between the antigen and the antigen-binding molecule reaches equilibrium. The antigen-binding affinity (e.g. $K_D$) can be appropriately determined using suitable methods known in the art, including, for example, plasmon resonance binding assay using instruments such as Biacore (see, for example, Murphy, M. et al, Current protocols in protein science, Chapter 19, unit 19.14, 2006).

In certain embodiments, the TrkB agonist antibody and the antigen-binding fragments thereof are capable of binding to human TrkB extracellular domain with EC50 (i.e. 50% binding concentration) of less than 4 nM (e.g. less than 3.5 nM, less than 3 nM, less than 2.5 nM, less than 2 nM, less than 1.5 nM, less than 1 nM, less than 0.5 nM, less than 0.4 nM, less than 0.3 nM, less than 0.2 nM, or less than 0.1 nM). Binding of the antibodies to human TrkB can be measured by methods known in the art, for example, ELISA, FACS, surface plasmon resonance, GST pull down, epitope-tag, immunoprecipitation, Far-Western, fluorescence resonance energy transfer, time resolved fluorescence immunoassays (TR-FIA), radioimmunoassays (MA), enzyme immunoassays, latex agglutination, Western blot, and immunohistochemistry or other binding assay. In an illustrative example, the test antibody (i.e. first antibody) is allowed to bind to immobilized human TrkB or cells expressing human TrkB, after washing away the unbound antibody, and a labeled secondary antibody is introduced which can bind to and thus allow the detection of the bound first antibody. The detection can be conducted with a microplate reader when immobilized TrkB is used, or by using FACS analysis when the cells expressing human TrkB are used.

In certain embodiments, the activation of TrkB by the antibody is less than the activation of TrkB by BDNF or NT-4. As described above, dimers of BDNF or NT-4 triggers dimerization of TrkB through conformational changes and autophosphorylation of tyrosine residues in its intracellular domain, thereby mediating three major signaling pathways involving mitogen-activated protein kinase (MAPK), phosphatidylinositol 3-kinase (PI3K) and phospholipase C-gamma 1 (PLC-gamma 1). Thus, the activation of TrkB can be determined by measuring the activation of the above three signaling pathways, or the phosphorylation of TrkB (pTrkB). A saturated BDNF or NT-4 (such as 10 nM or 100 nM) can be used to benchmark 100% activation of TrkB in the absence of the TrkB agonist antibody or the antigen-binding fragments thereof. Additive effects (or potentiation) in the presence of TrkB agonist antibody or the antigen-binding fragments thereof, and the saturated BDNF or NT-4 solution can be defined as BDNF or NT-4-induced TrkB activation of more than 100%. In certain embodiments, the additive effects may be at least 110%, at least 115%, at least 120%, at least 125%, at least 130%, at least 135%, at least 140%, at least 145%, or at least 150% of the benchmark activation of TrkB. In certain embodiments, the TrkB agonist antibody provided herein has an additive effect of at least 120%. In certain embodiments, the TrkB agonist antibody is TrkB-agoAb303.

In certain embodiments, the TrkB agonist antibody competes with BDNF and/or NT-4 for binding to TrkB. In certain embodiments, the TrkB agonist antibody does not compete with BDNF and/or NT-4 for binding to TrkB. The competition between the TrkB agonist antibody and BDNF and/or NT-4 can be determined by measuring the activation of TrkB, as described above. Alternatively, the competition between the TrkB agonist antibody and BDNF and/or NT-4 can be determined by competition ELISA, FMAT or BIAcore assays designed to test whether the TrkB binding agonist and BDNF bind to the same or overlapping epitopes, whether there is steric inhibition of binding, or whether binding of the first molecule induces a conformational change in TrkB that prevents or reduces binding of the second molecule.

For example, a TrkB binding agonist that does not compete with BDNF will cause no change in TrkB phosphorylation upon increasing concentrations of the agonist in the presence of saturating BDNF concentration (e.g. 10 nM, EC100). A TrkB binding agonist that does compete with BDNF will cause reduced TrkB phosphorylation upon increasing concentrations of the agonist in the presence of saturating BDNF concentration (e.g. 10 nM, EC100). In one embodiment, the TrkB binding agonist is non-competitive with BDNF where the total levels of phosphorylated TrkB in presence of agonist and a saturating concentration (EC100) BDNF is similar to the levels of phosphorylated TrkB in presence of the saturating concentration of BDNF alone, i.e. Total pTrkB (EC100 BDNF+agonist) Total pTrkB (EC100 BDNF). Similarly, in one embodiment, the TrkB binding agonist is non-competitive with NT-4 where the total levels of phosphorylated TrkB in presence of agonist and a saturating concentration (EC100) NT-4 is similar to the levels of phosphorylated TrkB in the presence of the saturating concentration of NT-4 alone, i.e. Total pTrkB (EC100 NT-4+agonist) Total pTrkB (EG100 NT-4). Levels of phosphorylated TrkB are considered to be similar where the mean total pTrkB measured in the presence of agonist and saturating levels of either BDNF or NT-4 is within the range (mean total pTrkB measured in the presence of saturating levels of either BDNF or NT-4±3 standard deviations). In one embodiment, mean total pTrkB measured in the presence of agonist and saturating levels of either BDNF or NT-4 is within the range (mean total pTrkB measured in the presence of saturating levels of either BDNF or NT-4±2 standard deviations). In another embodiment, mean total pTrkB measured in the presence of agonist and saturating levels of either BDNF or NT-4 is within the range (mean total pTrkB measured in the presence of saturating levels of either BDNF or NT-4±1 standard deviation). In the foregoing embodiment, the mean total levels of phosphorylated pTrkB are calculated based on at least three readings, and the larger of the two standard deviations (i.e. the standard deviation calculated in the presence of agonist and the standard deviation calculated in the absence of agonist) is used. In another embodiment, levels of phosphorylated TrkB are considered to be similar where the mean total pTrkB measured in the presence of agonist and saturating levels of either BDNF or NT-4 and the mean total pTrkB measured in the presence of saturating levels of BDNF or NT-4 differ by less than 10%. In another embodiment, levels of phosphorylated TrkB are considered to be similar where the mean total pTrkB measured in the presence of agonist and saturating levels of either BDNF or NT-4 and the mean total pTrkB measured in the presence of saturating levels of BDNF or NT-4 differ by less than 5%. A TrkB binding agonist that does not compete with BDNF or NT-4 for binding to TrkB is beneficial in a clinical setting, since the TrkB agonist could activate TrkB and not compete with the reduced levels of BDNF (or NT-4). Thus, BDNF and NT-4 can continue to play a physiological role, in addition to the TrkB binding agonist.

The reported key residues of the BDNF or NT-4/5 binding epitope on TrkB are Asp349, Asn350, Tyr329, Asp298, Cys302, Cys345 and His299 (Banfield et al., 2001). The detection of phosphorylation of ERK, Akt and PLC gamma, as well as TrkB can be performed by known methods in the art, such as western blot, at various time points, such as 0 min, 5 min, 15 min, 30 min, 1 hour, 2 hours, 6 hours, 12 hours, 24 hours or 36 hours. In certain embodiments, the phosphorylation of Akt triggered by the TrkB agonist antibody is similar or less than 90% (e.g. 80%, 70%, 60%, 50%, 40%, 30%, 20%, 10% or even less) than that of BDNF or NT-4 as measured by western blot. In certain embodiments, the phosphorylation of Erk triggered by the TrkB agonist antibody is similar or less than 90% (e.g. 80%, 70%, 60%, 50%, 40%, 30%, 20%, 10% or even less) than that of BDNF or NT-4 as measured by western blot. In certain embodiments, the phosphorylation of PLC gamma triggered by the TrkB agonist antibody is similar or less than 90% (e.g. 80%, 70%, 60%, 50%, 40%, 30%, 20%, 10% or even less) than that of BDNF or NT-4 as measured by western blot. In certain embodiments, the phosphorylation of Erk is measured at Thr202 and/or Tyr204 of Erk1 (Thr185 and/or Tyr187 of Erk2). In certain embodiments, the phosphorylation of Akt is measured at Thr308 and/or Ser473. In certain embodiments, the phosphorylation of PLC-gamma is measured at Tyr771, Tyr775, Tyr783, Ser1248, or the combination thereof. In certain embodiments, the autophosphorylation of TrkB is measured at Tyr515, Tyr701, Tyr705, Tyr706, Tyr816, Tyr490, Tyr670, Tyr674, Tyr675, Tyr771, Tyr783, Tyr785, Tyr1254, or the combination thereof.

In certain embodiments, the TrkB agonist antibodies and antigen-binding fragments thereof can be included in combination therapies, including standard chemo- and radiotherapies (e.g. radiotherapy, X-ray therapy), target based small molecule therapies (e.g. monoclonal antibodies, photodynamic therapy), immune therapy (e.g. antibodies against tumor markers, such as carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155, DLL4, Notch1, Notch2/3, Fzd7, or Wnt, r-spondin (RSPO) 1, RSPO2, RSPO3 or RSPO4), emerging other immune checkpoint modulator therapies (e.g. vaccine), hormonal therapy, angiogenesis inhibition (angiogenesis inhibitor), gene therapy (inducers of cellular proliferation, inhibitors of cellular proliferation, or regulators of programmed cell death), palliative care (i.e. treatment directed to improving the quality of care to reduce pain (e.g. morphine and oxycodone), nausea, vomiting (e.g. ondansetron and aprepitant), diarrhea and hemorrhage) and surgery. In certain embodiments, the antibodies and antigen-binding fragments thereof can be used as the base of antibody-drug conjugates, bispecific or multivalent antibodies.

The TrkB agonist antibodies and antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals. A bispecific or bivalent antibody is an artificial antibody having fragments of two different monoclonal antibodies and can bind to two different antigens. An antibody or antigen-binding fragment thereof that is "bivalent" comprises two antigen-binding sites. The two antigen binding sites may bind to the same antigen, or they may each bind to a different antigen, in which case the antibody or antigen-binding fragment is characterized as "bispecific."

In some embodiments, the TrkB agonist antibodies and antigen-binding fragments thereof provided herein are humanized or chimeric antibodies. In certain embodiments, the humanized or chimeric antibodies are prepared using recombinant methods. For example, a non-human animal can be immunized with proper antigen such as human TrkB protein. Gene fragments encoding the antibody variable regions that bind to the antigen are cut out from the gene of a monoclonal antibody of the mouse, and this portion is operably linked to a gene of the constant region of an antibody derived from human/non-human animal IgG1. The recombinant gene fragment is incorporated into an expression vector, which is then introduced into a host cell for the production of a chimeric antibody (see U.S. Pat. No. 4,816, 397; 4,816,567; 5,807,715).

A "humanized antibody" is an antibody obtained by grafting a non-human derived antibody CDR gene onto a human antibody gene, so that the variable region framework and constant regions are, if present, entirely or substantially from human antibody sequences. The methods for preparing a humanized antibody are known in the art (see, for example, U.S. Pat. Nos. 5,225,539, 5,530,101, 6,407,213; 5,859,205; 6,881,557 EP239400, EP125023, WO90/07861, and WO96/02576). In certain embodiments, a humanized antibody comprises a humanized heavy chain and a humanized light chain. In certain embodiments, the sequence of a grafted CDR in the humanized TrkB agonist antibody is at least 60%, 70%, 80%, 82%, 85%, 88%, 90%, 95% or 100% identical to the corresponding CDR. In certain embodiments, no more than 3 conservative amino acid substitutions occur in a CDR of the humanized TrkB agonist antibody. In certain embodiments, the amino acid residues of the variable region framework of the humanized TrkB antibody are substituted for sequence optimization. In certain embodiments, the variable region framework sequences of the humanized TrkB agonist antibody chain are at least 65%, 70%, 75%, 80%, 85%, 90%, 95% or 100% identical to the corresponding human variable region framework sequences.

In some embodiments, the TrkB agonist antibody and the antigen-binding fragment thereof is a single domain antibody, a camelid single domain antibody, a VNAR, a nanobody, an engineered human VH/VL single domain antibody, a diabody, a scFv, an scFv dimer, a BsFv, a dsFv, a (dsFv)$_2$, a dsFv-dsFv', an Fv fragment, a Fab, a Fab', a F(ab')$_2$, a ds diabody, a domain antibody, an isolated CDR or a bivalent domain antibody.

In some embodiments, the TrkB agonist antibodies and the antigen-binding fragments thereof further comprise an immunoglobulin constant region. In some embodiments, an immunoglobulin constant region comprises a heavy chain and/or a light chain constant region. The heavy chain constant region comprises CH1, CH1-CH2, or CH1-CH3 regions. In some embodiments, the constant region may further comprise one or more modifications to confer desirable properties. For example, the constant region may be modified to reduce or deplete one or more effector functions, to improve FcRn receptor binding, or to introduce one or more cysteine residues.

In some embodiments, the TrkB agonist antibodies and the antigen-binding fragments thereof further form an antibody-drug-conjugates (ADC's). It is contemplated that a variety of payload may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). The term of "payload (s)" are used interchangeable with "drug (s)", and these payloads may be linked to the antibodies or antigen-binding fragments by covalent binding, affinity binding, intercalation, coordinate binding, complexation, association, blending, or addition, among other methods. In certain embodiments, the antibodies and antigen-binding fragments disclosed herein may be engineered to contain specific sites outside the epitope binding portion that may be utilized for binding to one or more payloads, such as peptides, nucleic acid molecules, drugs, cytotoxins, polypeptides, proteins, fusion proteins, antibodies, haptens, small molecules, mimetic agents, synthetic drugs, inorganic molecules, organic molecules, radioisotopes and reporter groups. For example, such a site may include one or more reactive amino acid residues, such as for example cysteine or histidine residues, to facilitate covalent linkage to a payload. In certain embodiments, the antibodies may be linked to a payload indirectly via a linker, or through another payload. For example, the antibody or antigen-binding fragments may be conjugated to biotin, then indirectly conjugated to a second payload that is conjugated to avidin. The payload can be a reporter group or a detectable label, a pharmacokinetic modifying moiety, a purification moiety, or a cytotoxic moiety. Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luciferases, glucoamylase, lysozyme, saccharide oxidases or β-D-galactosidase), radioisotopes (e.g. 123I, 124I, 125I, 131I, 35S, 3H, 111In, 112In, 14C, 64Cu, 67Cu, 86Y, 88Y, 90Y, 177Lu, 211At, 186Re, 188Re, 153Sm, 212Bi, and 32P, other lanthanides, luminescent labels), chromophoric moiety, digoxigenin, biotin/avidin, a DNA molecule or gold for detection. In certain embodiments, the payload can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like. In certain embodiments, the payload can be a purification moiety such as a magnetic bead. A payload of "cytotoxic" moiety can be any agent that is detrimental to cells or that can damage or kill cells. Examples of cytotoxic moiety include, without limitation, a chemotherapeutic agent, an anti-tumor agent, a growth inhibitor, a drug, a toxin, such as, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, platiniums (e.g., cisplatin and oxaliplatin), plant alkaloids (e.g., topoisomerase inhibitors, vinca alkaloids, taxanes, and epipodophyllotoxins) and anthramycin (AMC)), and anti-mitotic agents (e.g., vincristine and vinblastine). The term "loading" or "drug loading" or "payload loading" as used herein refers to the average number of drugs/payloads per antibody. The drug loading can be within the range from 1 to 20 (e.g. from 1 to 15, 1 to 10, 2 to 10, 1 to 8, 2 to 8, 2 to 6, 2 to 5 or 2 to 4) drugs per antibody (also as drug to antibody ratio), as determined by suitable methods in the art, such as mass spectrometry, UV/visible spectroscopy, ELISA assay, and HPLC. In certain embodiments, the drug loading is 1, 2, 3, 4, 5, 6, 7, 8, 9 or 10.

Polynucleotides and Recombinant Methods

The present disclosure provides isolated polynucleotides that encode the TrkB agonist antibodies and the antigen-binding fragments thereof. In certain embodiments, the isolated polynucleotides comprise one or more nucleotide sequences encoding the CDR sequences provided in the present disclosure.

Antibodies may be prepared by any of a variety of techniques known to those of ordinary skill in the art. See, e.g., Harlow and Lane, Antibodies: A Laboratory Manual, Cold Spring Harbor Laboratory, 1988. In certain embodiments, the process of producing the monoclonal TrkB agonist antibody or the antigen-binding fragments thereof includes: Immunizing a suitable animal with human TrkB protein or hTrkB agonist producing cells. The animal can be a rodent, e.g., a mouse or rat, e.g., a Velocimouse®, Kymouse®, Xenomouse®, Aliva Mouse®, HuMab Mouse®, Omnimouse®, Omnirat® or MeMo Mouse®, sheeps, goats, cattle, horses, rabbits, guinea pigs, and the like. Generate hybridoma using the spleen or the lymph node or gathering B cells of the immunized animal and measuring the TrkB agonist antibodies titer. Clone the polynucleotides encoding the TrkB agonist antibodies or the antigen-binding fragments thereof with suitable titer from the hybridoma or B cell clones from the immunized animal. The cloned or modified (e.g. chimeric, humanized) polynucleotides are incorporated into a suitable vector, which is then introduced into host cells to produce of the antibody of the disclosure. The antibody and the antigen-binding fragments thereof provided herein can be obtained in a substantially pure and homogeneous form by culturing the host cells, followed by separation and purification of the host cells or the culture liquid (e.g. supernatant). For the separation and purification of the antibody or the antigen-binding fragments thereof, an ordinary method used for polypeptide purification can be employed. Monoclonal antibodies can be prepared, for example, using the technique of Kohler and Milstein, Eur. I Immunol. 6:511-519, 1976, or the modifications thereto. Also included are methods that utilize transgenic animals such as mice to express antibodies of a different species other than the host animal, such as human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Such examples include the VELOCIMMUNE® platform developed by REGENEREX®. In certain embodiments, the antibody provided herein is obtained through at least one of the processes selected from: (1) fusing lymphocyte from the above immunized animal with amyeloma cell to generate a hybridoma, which expresses the antibody; (2) isolating antigen specific B cell from lymphocyte of the above immunized animal, and cloning the antibody via PCR and expressing the antibody; or (3) isolating mRNA from lymphocyte of the above immunized animal to obtain the antibody through phage display, ribosome display, yeast display, bacteria display, baculovirus display, mammal cell display, or mRNA display libraries (see, e.g., U.S. Pat. No. 7,244,592; Chao et al., Nature Protocols. 1:755-768, 2006). These display methods are all conventional techniques in the art, the specific operations thereof can be found in corresponding textbooks or operation manuals, see, e.g. Mondon P et al., Front. Biosci. 13:1117-1129, 2008. In certain embodiments, the binding site(s) of the antibody or the antigen-binding fragment thereof are selected from a plurality (e.g., library) of binding sites that comprises or consists of a plurality of 4-chain antibodies or the antigen-binding fragments thereof, e.g., dAbs, Fabs or scFvs.

The isolated polynucleotide that encodes the TrkB agonist antibodies and the antigen-binding fragments thereof can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence (e.g. translation signals or leader sequence), an origin of replication, one or more selectable marker genes, an enhancer element, a promoter (e.g. SV40, CMV, EF-1α), and a transcription termination sequence.

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO,pVIVO, pMAL, pMONO, pSE-LECT, pUNO, pDUO, Psg5L, pBABE, pWPXL, pBI, p15TV-L, pPro18, pTD, pRS420, pLexA, pACT2.2, pCDM8, pCDNA1.1/amp, pcDNA3.1, pRc/RSV, pEF-1, pCMV-SCRIPT.RTM., pFB, pSG5, pXT1, pCDEF3, pSVS-PORT, pEF-Bos, etc, and other laboratory and commercially available expression vectors. Suitable vectors may include, plasmid, or viral vectors (e.g., replication defective retroviruses, adenoviruses and adeno-associated viruses). The vectors can be maintained in single copy or multiple copies, or integrated into the host cell genome. Vectors comprising the polynucleotide sequence encoding the antibody or antigen-binding fragment can be introduced to a host cell for replication or gene expression. Suitable host cells for cloning or expressing the DNA in the vectors herein are the prokaryote, yeast, insect cells or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces, Bacillus, Streptococcus, Streptomyces, Staphylococcus, Enterococcus, Lactobacillus, Lactococcus, Clostridium, Geobacillus, Oceanobacillus, Pseudomonas, Salmonella, Campylobacter, Helicobacter, Flavobacterium, Fusobacterium, Ilyobacter, Neisseria*, and *Ureaplasma*. Suitable insect cells include *Drosophila* Schnieder S2 cells and Sf9). Suitable yeast includes *P. methanolica, P. pastoris, S. cerevisiae* or common baker's yeast. Preferable mammalian cells include CHO cells, HEK293 cells, lymphocytes and myelomas. In certain embodiments, when glycosylation and Fc effector function for an antibody are not needed, the antibody may be produced in bacteria.

In addition to the above examples, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, vertebrate cells have drawn the greatest interest, and the propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatocellular carcinoma cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; PC12; mouse embryo fibroblast cell line (3T3); NSO myeloma cells (a murine myeloma cell line that does not endogenously produce any functional immunoglobulin chains). Different host cells have various characteristic and mechanisms for the post-translational processing and modification of proteins and gene products. Therefore, suitable cell lines can be chosen as host cells to ensure the correct modification and processing (such as primary transcript, glycosylation, and phosphorylation) of the antibody expressed. In some preferable embodiments, the host cell is HEK293T cell. In some preferable embodiments, the host cell is CHO cell.

Host cells are transformed with the above-described expression or cloning vectors for TrkB agonist antibody production and cultured in conventional nutrient media modified as appropriate for inducing promoters, selecting transformants, or amplifying the genes encoding the desired sequences. In certain embodiments, the vectors can be transferred into the host cell by methods known in the art such as transformation, electroporation, calcium phosphate treatment, lipofection. In certain embodiments, transfection of a vector into a eukaryote includes calcium phosphate co-precipitates, microinjection, electroporation, lipofection and viral infection. The eukaryotic host cell may be co-transformed with a second polynucleotide encoding the antibody. In certain embodiments, the host cell containing the transferred vector can transiently express the TrkB agonist antibody.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma), Luria broth (LB), and Terrific broth (TB) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody and the antigen-binding fragments thereof can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody and the antigen-binding fragments thereof are secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, hydrophobic chromatography, reverse-phase chromatography, absorption chromatography, filtration, ultrafiltration, solvent precipitation, solvent extraction, distillation, SDS-polyacrylamide gel electrophoresis, dialysis, DEAE-cellulose ion exchange chromatography, ammonium sulfate precipitation, salting out, immunoprecipitation, isoelectric focusing, recrystallization and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human gamma.1, gamma.2, or gamma.4 heavy chains (Lindmark et al., J. Immunol. Meth. 62:1-13 (1983)). Examples of protein A columns include Hyper D, POROS, and Sepharose FF (GE Healthcare Biosciences). Protein G is recommended for all mouse isotypes and for human gamma.3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX.™. resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Kits

The present disclosure in yet another aspect provides kits comprising the TrkB agonist antibodies or the antigen-binding fragments thereof, or the pharmaceutical composition comprising the TrkB agonist antibodies or the antigen-binding fragments thereof provided herein. In some embodiments, the kits are useful for detecting the presence or the level of TrkB in a biological sample. The biological sample can comprise a cell or a tissue.

In some embodiments, the TrkB agonist antibody or the antigen-binding fragment thereof which is comprised in the kit is conjugated with a detectable label (for example, fluorescent, radioactive or enzymatic label). In certain other embodiments, the kit comprises an unlabeled TrkB agonist antibody or antigen-binding fragments thereof or a pharmaceutical composition containing the unlabeled TrkB agonist antibody or antigen-binding fragments thereof, and further comprises a secondary labeled antibody which is capable of binding to the unlabeled TrkB agonist antibody. The kit may further include means of detecting a label (for example, filter sets to detect fluorescent labels, enzyme substrates for enzymatic labels, etc). The kit may comprise additional reagents and buffers used for the performance of a particular method. The kit may further comprise an instruction of use, and a package that separates each of the components in the kit. In certain embodiments, the kit comprises an immunoassay for detecting the TrkB agonist antibody.

In certain embodiments, the TrkB agonist antibody or the antigen-binding fragment thereof that are comprised in the kit is associated with a substrate or a device useful in a sandwich assay such as ELISA, or in an immunographic assay. Useful substrate or device can be, for example, microtiter plate and test strip.

In certain embodiments, the kit is provided for detecting TrkB protein level. In some embodiments, the kit is used for predicting, diagnosing, preventing or treating TrkB associated conditions.

Pharmaceutical Composition and Method of Treatment

The present disclosure further provides pharmaceutical compositions comprising the TrkB agonist antibodies or the antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, humectants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding activity or binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine. Suitable humectants include, ethylene glycol, glycerin, or sorbitol. Suitable lubricants include, for example, cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate or white wax, or a mixture of two or more thereof. Suitable emulsifiers include carbomer, polyoxyethylene-20-stearyl ether, cetostearyl alcohol, cetyl alcohol, cholesterol, diglycol stearate, glyceryl stearate, hydroxypropyl cellulose, hydroxypropylmethyl cellulose, lanolin, polyoxyethylene lauryl ether, methyl cellulose, polyoxyethylene stearate, polysorbate, propylene glycol monostearate, sorbitan esters or stearic acid.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, lotion, foam, pill, capsule, tablet, sustained release formulation, ointment, cream, paste, gel, spray, aerosol, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the TrkB agonist antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Therapeutic methods for treating a TrkB associated condition are also provided, comprising: administering to a subject a therapeutically effective amount of the TrkB agonist antibody or the antigen-binding fragments thereof as provided herein, thereby treating or preventing a condition or a disorder associated with TrkB. In another embodiment, methods are provided to treat a condition in a subject that would benefit from activation of TrkB, comprising administering a therapeutically effective amount of the TrkB agonist antibody as provided herein to a subject in need thereof.

The therapeutically effective amount (when used alone or in combination with other agents such as chemotherapeutic agents) of an antibody or antigen-binding fragment as provided herein will depend on various factors known in the art, such as for example type of disease to be treated, the type of antibody, body weight, age, past medical history, present medications, state of health of the subject, immune condition and potential for cross-reaction, allergies, sensitivities and adverse side-effects, as well as the administration route and the type, the severity and development of the disease and the discretion of the attending physician or veterinarian. In certain embodiments, an antibody or antigen-binding fragment as provided herein may be administered at a therapeutically effective dosage of about 0.01 mg/kg to about 100 mg/kg one or more times per day (e.g., about 0.01 mg/kg, about 0.2 mg/kg, about 0.3 mg/kg, about 0.5 mg/kg, about 1 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg one or more times per day). In certain embodiments, the antibody or antigen-binding fragment is administered at a dosage of about 50 mg/kg or less, and in certain the dosage is 20 mg/kg or less, 10 mg/kg or less, 3 mg/kg or less, 1 mg/kg or less, 0.3 mg/kg or less, 0.2 mg/kg or less, or 0.1 mg/kg or less. In certain embodiments, the administration dosage may change over the course of treatment. For example, in certain embodiments the initial administration dosage may be higher than the subsequent administration dosages. In certain embodiments, the administration dosage may vary over the course of treatment depending on the reaction of the subject.

Dosage regimens may be adjusted to provide the optimum desired response (e.g., a therapeutic response). In certain embodiments, antibody or antigen-binding fragment as provided herein is administered to the subject at one time or over a series of treatments. In certain embodiments, antibody or antigen-binding fragment as provided herein is administered to the subject by one or more separate administrations, or by continuous infusion depending on the type and severity of the disease. Guidance can be found in for example, U.S. Pat. Nos. 4,657,760; 5,206,344; 5,225,212.

The antibodies and antigen-binding fragments disclosed herein may be administered by any route known in the art, such as for example parenteral (e.g., subcutaneous, transdermally (e.g., by a patch), extracorporeally, intraperitoneal, intravenous, including intravenous infusion, intramuscular, or intradermal injection) or non-parenteral (e.g., oral, intranasal, intraocular, sublingual, rectal, or topical) routes. The antibodies and antigen-binding fragments disclosed herein may be administered into the central nervous system (e.g., into the brain (intracerebrally or intra ventricularly), spinal cord, or into the cerebrospinal fluid), or any combination thereof.

In certain embodiments, the antibodies and antigen-binding fragments disclosed herein may be administered in a controlled-release manner. A controlled-release parenteral preparations can be made as implants, oily injections or particulate systems (e.g. microspheres, microparticles, microcapsules, nanocapsules, nanospheres, and nanoparticles) (see Banga, A. J., Therapeutic Peptides and Proteins: Formulation, Processing, and Delivery Systems, Technomic Publishing Company, Inc., Lancaster, Pa., (1995); Kreuter, J., Colloidal Drug Delivery Systems, J. Kreuter, ed., Marcel Dekker, Inc., New York, N.Y., pp. 219-342 (1994); Tice & Tabibi, Treatise on Controlled Drug Delivery, A. Kydonieus, ed., Marcel Dekker, Inc. New York, N.Y., pp. 315-339, (1992)). In certain embodiments, the TrkB agonist antibodies and antigen-binding fragments disclosed herein may be administered in degradable or nondegradable polymeric matrices (see Langer, Accounts Chem. Res. 26:537-542, 1993).

Conditions associated with TrkB can be cancer or tumor. In certain embodiments, the condition is solid tumors, hematological disorders, infectious diseases, autoimmune diseases or fibrotic diseases. In certain embodiments, the solid tumors include, for example, non-small cell lung cancer (squamous/nonsquamous), small cell lung cancer, renal cell cancer, colorectal cancer, colon cancer, ovarian cancer, breast cancer (including basal breast carcinoma, ductal carcinoma and lobular breast carcinoma), pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, myelomas, mycoses fungoids, merkel cell cancer, hepatocellular carcinoma (HCC), fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma. The hematologic disorders include such as classical Hodgkin lymphoma (CHL), primary mediastinal large B-cell lymphoma, T-cell/histiocyte-rich B-cell lymphoma, acute lymphocytic leukemia, acute myelocytic leukemia, acute myelogenous leukemia and myeloblastic, promyelocytic, myelomonocytic, monocytic and erythroleukemia, chronic myelocytic (granulocytic) leukemia, chronic myelogenous leukemia, chronic lymphocytic leukemia, polycythemia vera, mast cell derived tumors, EBV-positive and -negative PTLD, and diffuse large B-cell lymphoma (DLBCL), plasmablastic lymphoma, extranodal NK/T-cell lymphoma, nasopharyngeal carcinoma, and HHV8-associated primary effusion lymphoma, non-Hodgkin's lymphoma, multiple myeloma, Waldenstrom's macroglobulinemia, heavy chain disease, myelodysplastic syndrome, hairy cell leukemia and myelodysplasia, neoplasm of the central nervous system (CNS), such as primary CNS lymphoma, spinal axis tumor, brain stem glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma.

In certain embodiments, the TrkB agonist antibody can be used to treat neuronal diseases, such as neurodegenerative diseases, psychiatric disorders, metabolic disorders, brain injury, optic neuropathies and retinal degenerative conditions, hearing loss disorders, neurodevelopmental disorders, disorders of body weight regulation, muscular disorders and other CNS disorders.

Neurodegenerative diseases include Amyotrophic Lateral Sclerosis (ALS), Huntington's Disease (HD), Alzheimer's Disease (AD), Motor Neuron Disease (including progressive muscular atrophy), Parkinson's disease, prion diseases including Creutzfeldt-Jakob disease (OD), Lewy body disease, Spinal muscular atrophy, Multiple system atrophy, Dementia (including fronto-temporal dementia) and tauopathies. More particular neurodegenerative disorders include ALS, Huntington's Disease and Motor Neuron Disease.

Psychiatric disorders include: anxiety, mood disorder, depression (including major depressive disorder), panic disorder, post-traumatic stress disorder (PTSD), attention deficit hyperactive disorder (ADHD), bipolar disorder and Schizophrenia.

Neurodevelopmental disorders include: Angelman syndrome, Prader-Willi syndrome Autistic disorder and Rett syndrome.

Particular optic neuropathies include: glaucoma (for example open angle glaucoma, wide angle glaucoma, angle closure glaucoma (acute and chronic), normal tension glaucoma), anterior ischaemic optic neuropathy (AION) (for example, non-arteritic ischeamic optic neuropathy (NAION)), posterior ischemic optic neuropathy, radiation optic neuropathy, compressive optic neuropathy (for example, papilledema), infiltrative optic neuropathy, traumatic optic neuropathy, mitochondrial optic neuropathy, toxic optic neuropathies, hereditary optic neuropathies (for example, autosomal dominant optic atrophy (ADOA; optic atrophy type Kjer), Leber hereditary optic neuropathy, Rosenberg Chutorian syndrome, Wolfram syndrome, optic nerve hypoplasia), optic neuritis (for example, neuromyelitis optica, papillitis). Retinal degenerative disorders would include hereditary dystrophies (e.g. retinitis pigmentosa) or acquired conditions including age-related macular degeneration (wet and dry). In one embodiment, optic neuropathies include for example conditions impacting retinal ganglion cells (RGC) and/or the optic nerve. Particular optic neuropathies include: glaucoma (for example open angle glaucoma, wide angle glaucoma, primary angle closure glaucoma, normal tension glaucoma), anterior ischaemic optic neuropathy (AION), non-anterior ischeamic optic neuropathy (NAION), traumatic optic neuropathies and Leber hereditary optic neuropathy. Retinal degenerative disorders would include hereditary or acquired conditions including age-related macular degeneration (wet and dry).

Hearing loss disorders include sensorineural hearing loss (SNHL) (bilateral, unilateral and unspecified) and composite hearing loss (in which there are sensorineural and conductive loss elements; bilateral, unilateral and unspecified). Sensorineural hearing loss includes sensory (cochlear related) or a neural (8th nerve related) hearing loss. Sensorineural hearing loss may result from end organ lesions. End organ lesions associated with sensorineural hearing loss include: acoustic trauma (due to a noise greater than, for example 85 decibels (db)), viral endolymphatic labyrinthitis, Meniere's disease, cerebellopontine angle tumors of the 8th nerve, bacterial or viral infection of the 8th nerve ganglia, (e.g. with herpes zoster oticus), purulent labyrinthitis arising from acute otitis media, purulent meningitis, chronic otitis media, sudden deafness including that of viral origin, e.g., viral endolymphatic labyrinthitis caused by viruses including mumps, measles, influenza, chickenpox, mononucleosis and adenoviruses) and transient ischaemic deafness, fractures of the temporal bone extending into the middle ear and rupturing the tympanic membrane and possibly the ossicular chain, fractures affecting the cochlea, and acoustic neurinoma, which are tumors generally of Schwann cell origin that arise from either the auditory or vestibular divisions of the 8th nerve. The end organ lesion hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. Sensorineural hearing loss may alternatively be age-related, for example, presbycusis (including presbyacusia), which is a sensorineural hearing loss occurring as a normal part of aging. Sensorineural hearing loss may ototoxic hearing loss (hearing loss resulting from an ototoxic drug (e.g. certain antiobiotics, certain chemotherapeutics, certain salicylate compounds—particularly aspirin—certain diuretics—common loop diuretics—and certain quinines) that affects the auditory portion of the inner ear, particularly the organ of Corti).

Muscular disorders include sarcopenia.

Other CNS disorders include: diabetic neuropathy, epilepsy, multiple sclerosis, migraine, nerve injury (including traumatic brain injury (TBI), spinal cord injury and peripheral nerve injury), peripheral neuropathies, neuromuscular diseases (including myasthenia gravis and myasthenic syndromes), sleep disorders and Stroke. In one example, peripheral neuropathy includes Chemotherapy induced peripheral neuropathy (CIPN). CIPN is a major dose-limiting side effect of many anticancer drugs.

In certain embodiments, the TrkB agonist antibody can be used in the treatment of diseases, disorders or conditions, or in the manufacture of medicament for treating the diseases, disorders or conditions including, but not limited to, Amyotrophic Lateral Sclerosis (ALS), Huntington's Disease (HD), Stroke, Spinal Cord Injury, Alzheimer's Disease (AD), motor neuron disorders, traumatic brain injury (TBI), dementias, tauopathies, peripheral neuropathy, nerve injury, peripheral nerve injury, Parkinson's disease, prion diseases including Creutzfeldt-Jakob disease (CJD), psychiatric disorders, Schizophrenia, multiple sclerosis, Rett syndrome, Lewy body disease, Multiple system atrophy, myasthenia gravis, diabetic neuropathy, retinal degeneration, glaucoma, hearing loss, bodyweight regulation, anorexia nervosa, cachexia, neuromuscular disease, mood and depressive disorders, post-traumatic stress disorder, attention deficit hyperactive disorder (ADHD), bipolar disorder, anxiety, Autistic disorder, pain, disorders involving bodyweight regulation, anorexia nervosa, cachexia, unwanted weight loss, and opioid-induced emesis.

Alzheimer's Disease

At present, the pathogenesis of neurodegenerative diseases can be roughly divided into 2 kinds at gene level: one is the pathogenic gene mutation leading to accumulation of toxins, the other is the mutation or regulation disorder of the gene of self-repairing ability. The present study of neurodegenerative disease tends to focus on the pathogenesis of the disease, namely how to reduce the neurotoxins that cause neuronal death. However, the drug development for treatment of senile dementia based on this idea, including 5 large phase III clinical trials in recent years, all failed (Karran and Hardy, 2014; Mullard, 2012). The main reason is that it is the pathogenic toxin that is aimed by the drug. However, when disease symptoms appear the toxin has poisoned the neurons for several years or even decades and neurons have been seriously damaged or even died. It is too late to reduce toxin at that time. A new approach is to study the pathophysiology which is directly related to the disease symptoms (Lu et al., 2013a). So far, synaptic loss is the main common pathophysiological features in neurodegenerative diseases and results in brain cognitive function damage, while neurons gradually die and lead to the more serious loss of cognitive ability as well as other conditions. The former in the physiological process of the disease is reversible, so it is easy to be treated. Thus, synaptic repair is one of the most viable entry point to study the treatment of Alzheimer's disease (Sheng et al., 2012).

The organism itself protects synapsis and repairs synaptic damage mainly by brain-derived neurotrophic factor BDNF. The abnormalities or abnormal expression of the gene may increase the chance of early-onset Alzheimer's disease and accelerate the development of the disease (Lu et al., 2013a). As the most important member of the neurotrophin family, in neural development, BDNF plays a very important role in neuronal survival, neural plasticity and other important functions. Its main function is mediated by the high-affinity receptor TrkB (Chao and Lee Huang and, 2004; Reichardt, 2001; Poo, 2001). A common variant of the BDNF gene (single nucleotide polymorphism, SNP), where amino acid changes from Val to Met at position 66 (Egan et al., 2003), makes the hippocampus and amygdala nuclei of the carriers of the mutation become smaller, and lowers the level of various kinds of memory including scenario memory and visual space memory, etc. These symptoms and a lower BDNF level can be detected in model mice and patients with Alzheimer's disease at the same time, which shows that research related to BDNF in Alzheimer's disease work is particularly necessary (Dennis et al. Sanchez et, 2011; al., 2011; Voineskos et al. Yang et, 2011; al., 2012). In rodents and primates model with Alzheimer's disease, overexpress of BDNF in use of virus can inhibit neuronal death (Nagahara et al., 2009). More importantly, in the research of the last several years we found that in ApoE4-positive healthy people and patients (Europeans) who carry the BDNF Met66 genotype, higher levels of beta plaques in the cerebral temporal lobe and prefrontal cortex would be produced and aggregated (see above). At the same time hippocampal volume and episodic memory ability drop faster. Those show that BDNF is very important for the repair and treatment of Alzheimer's disease. Thus it is a very promising therapeutic target (Lu et al., 2013a; Nagahara and Tuszynski, 2011). The present disclosure provides herein TrkB agonist antibodies or the antigen-binding fragments thereof functions similarly or more effectively than BDNF in preventing, treating, relieving, delaying the onset of or reducing the risk of developing into Alzheimer's disease and other dementias, including slowing the progression of cognitive function decline. The TrkB agonist antibody may enhance cell survival, promote neurite outgrowth, and/or regulating synapse plasticity.

Amyotrophic Lateral Sclerosis (ALS)

Amyotrophic lateral sclerosis (ALS) is the most common type of motoneuron disease (MND), in which both the upper and lower motoneurons are affected (Wijesekera and Leigh, 2009). Pathologically, ALS patients show decreased number of motoneurons in the anterior horn of spinal cord, brain stem and motor cortex. Loss of motoneurons leads to muscle denervation and atrophy. Patients are characterized by progressive loss of motor function, including muscle weakness and swallowing difficulties, and finally die of respiratory failure (Boillee et al., 2006; Mitchell and Borasio, 2007). Majority of the ALS cases are sporadic, and 5~10% are familial cases. SOD1 is the first identified ALS-related gene, and its mutations account for up to 20% familial cases (Rosen, 1993). Up to now, more than 20 genes are found to cause familial ALS when mutated, gene mutations are also identified in sporadic cases (Couthouis et al., 2011; Wijesekera and Leigh, 2009). Despite the genetic heterogeneity, protein deposits in the affected regions are common hallmarks of ALS.

There is currently no cure for ALS, whereas riluzole, a glutamate release inhibitor, shows mild effects in improving survival for a few months (Carlesi et al., 2011; Miller et al., 2007). After decades of research, a consensus on the pathogenic mechanism of ALS is still absent, which hinders the development of effective therapies. An alternative strategy attempts to promote the survival of motoneurons through activating intrinsic neurotrophin pathway, rather than specifically block the pathogenic process that leads to motoneuron death (Lu et al., 2013). Brain derived neurotrophic factor (BDNF) binds tropomyosin-related kinase B (TrkB) with high affinity, and their downstream pathway promotes cell survival and neurite growth (Huang and Reichardt, 2003; Reichardt, 2006). There is evidence indicate abnormal BDNF-TrkB signaling in pathological conditions. Earlier reports show that in spinal cords of ALS patients, TrkB mRNA and protein levels were higher than that of controls, however TrkB protein was less phosphorylated (Mutoh et al., 2000). BDNF mRNA and protein levels also showed elevation in muscle of ALS patients (Kust et al., 2002). Mutations within fused in sarcoma (FUS) gene also leads to ALS (Kwiatkowski et al., 2009; Vance et al., 2009). Recently, the DNA/RNA binding protein FUS has been implicated in regulating expressing and alternative splicing of BDNF (Lagier-Tourenne et al., 2012; Qiu et al., 2014), suggesting the relationship of disease-causing mutation and compromised neurotrophin signaling. In mice expressing mutant FUS, splicing of BDNF pre-mRNA is impaired, and the levels of BDNF protein and TrkB phosphorylation decreased (Qiu et al., 2014).

Many efforts have been made to develop BDNF and relevant molecules to treat neurological and psychotic diseases. The effect of BDNF has been examined in several neurodegenerative diseases (Bai et al, 2010; Gharami et al, 2008; Nagahara and Tuszynski, 2011; Lu et al., 2013). Transgenic or viral expression of BDNF seem to have positive effects on neurodegenerative disease models, but simple BDNF dosing does not because its poor pharmacokinetic and physical characters (Gharami et al, 2008; Xie et al, 2010; Thoenen et al, 2002). The present disclosure establishes a system to manufacture and screen several TrkB agonist monoclonal antibodies not only for drug discovery of neurodegenerative disease but also for potential scientific research on TrkB signaling and structure.

The activation of BDNF-TrkB signaling has been proven effective in treating spinal cord injury on animal models (Gransee et al., 2013; Kishino et al., 1997; Mantilla et al., 2013). However, in rodent models of ALS, administration of BDNF could not slow down the disease progression, and BDNF fail to benefit ALS patient in clinical trials (1999;

Ochs et al., 2000). This may due to pool parmacokinetics and diffusibility of BDNF, which leads to high local concentration of BDNF eventually causes decreased TrkB expression (Dittrich et al., 1996; Knusel et al., 1997). Several small compounds were reported to stimulate TrkB and could be potentially used in some neurodegenerative diseases (Longo and Massa, 2013). However, there is also one work reports some confused results (Todd et al, 2014). And it seems that it is impossible to invent a small compound to mimic the dimerization effect of BDNF according to the structure of BDNF/TrkB complex. Previous reports showed that the specific antibodies could activate receptor tyrosine kinase by cross-linking two monomer receptors, mimicking the natural ligands (Clary et al., 1994; LeSauteur et al., 1996). Comparing with BDNF, TrkB agonist antibody has the advantages of higher specificity, longer half-time and so on. TrkB agonist monoclonal antibody specially activate TrkB but not TrkA and TrkC. More importantly, TrkB agonist Mab does not bind p75NTR and so does not induce any negative effects as those might be induced by BDNF-p75NTR (Lu et al, 2005). The present disclosure provides herein TrkB agonist antibodies or the antigen-binding fragments thereof functions similarly or more effectively than BDNF in preventing, treating, relieving, delaying the onset of or reducing the risk of developing into ALS, including promoting motor neuron survival and function.

Glaucoma

Figure 2:
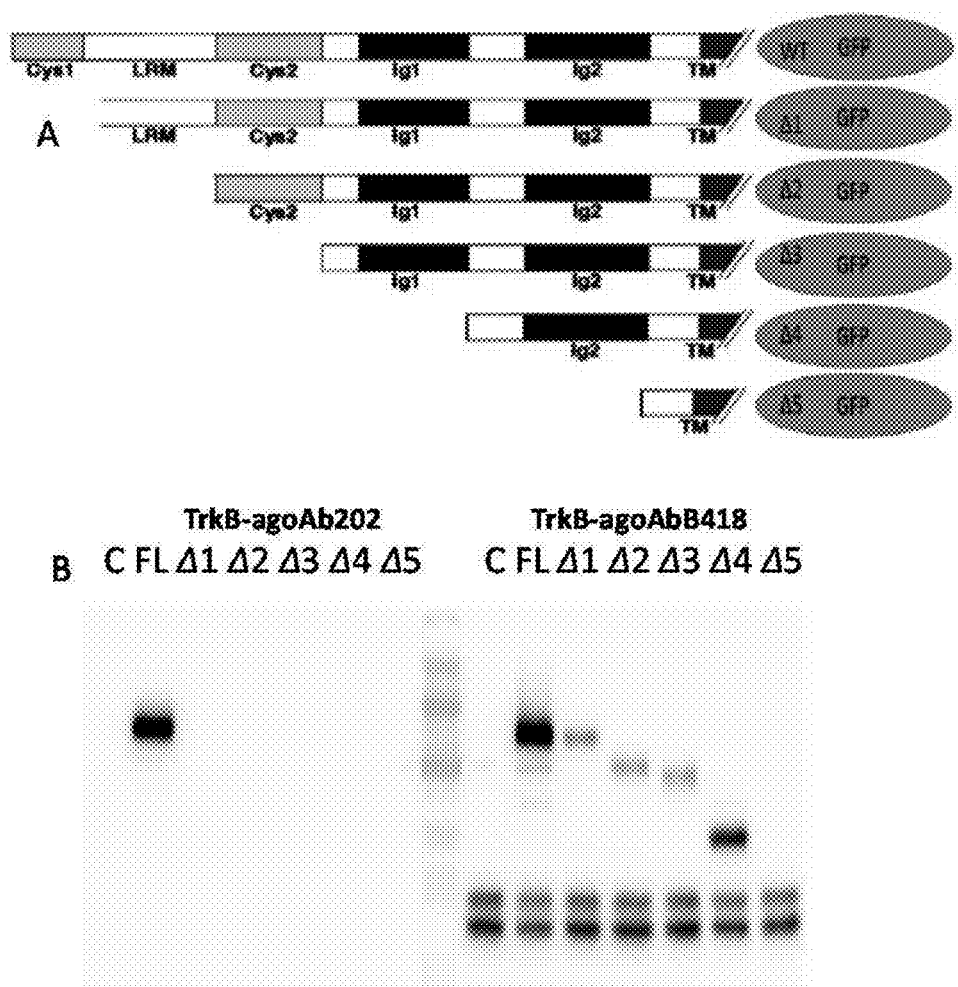
FIGS. 2A-2B illustrate the truncated TrkB and the target domains of the TrkB agonist antibodies.

Glaucoma is a neurodegenerative eye disease with pathological changes in optic nerve head (optic disk) and optic nerve, and is typically accompanied with visual field loss and raised TOP (NICE, 2009). Glaucoma has been the leading cause of blindness worldwide in the past 30 years (Dandona and Dandona, 2006; Quigley, 1996; Quigley and Broman, 2006). Approximately 10% of UK blindness registrations are attributed to glaucoma (Casson et al., 2012; NICE, 2009). In the realm of epidemiology, the population of glaucoma patients is growing rapidly (FIG. 2 and Tab. 1) with the rapidly aging of society and increasing prevalence of eye fatigue in the age of information. The total estimated number of glaucoma patients in China will reach ~21.8 million in 2020 s, taking 3.05% of total Chinese population above 40 years old, which will exceed the world average 2.86%. Because glaucomatous damage of RGCs and optic nerve is irreversible, all kinds of glaucoma have strong potential possibility leading to final blindness. However, according to the medical condition in China today, most people do not go to hospital to check their eyes in the early-stage glaucoma because of lacking health insurance. Thus, based on the medical care situation and the progressive blindness of glaucoma, the increasing of glaucoma patients in china exerts huge burden on family and society. Our ultimate aim is to search for the effective medicals or antibodies targeting neurotropic pathway to slow down and reverse the progressive blindness of glaucoma and to regenerate damaged RGCs and axons in late-stage glaucoma, which was believed that glaucomatous progression is irreversible by traditional clinical therapy.

Barkan firstly divided glaucoma into closed-angle and open-angle in 1930s (Barkan, 1938). Today, the classification of glaucoma seems complicated, but based on two comparatively simple criteria. One is the IOP value and the other is anatomical iridotrabecular contact or not (Casson et al., 2012). All kinds of glaucoma have the same characteristic, GON, which can be detected and diagnosed by several eye clinical methods, such as measuring neuroretinal rim thickness, scanning the abnormality in retinal and optic nerve head, and testing the horizontal wideness (NICE, 2009). Although not all glaucoma patients suffer from elevated IOP (but some of patients' IOP is not observed at the early stage), lowering all glaucoma patients' IOP has the positive effects on their vision ability, retarding the final blindness and lowering RGCs loss (Heijl et al., 2002; Leske et al., 1999). Thus, elevated IOP is always recognized as an important marker for early-stage or suspect glaucoma in many countries.

The reason why glaucomatous progression is accompanied with elevated IOP is not very clear now. A forceful hypothesis is pressure-induced axonal transport obstruction (Johnson et al., 2000), which states retina and RGCs survival are protected by retrograde transportation of neurotrophins from downstream brain regions, such as superior colliculus (SC), and lateral geniculate nucleus (LGN). Several studies provide a lot immunostaining or isotopic experiments, which confirm elevated IOP is accompanied with diminished distribution of BDNF and NT4/5 in optic head and with increased proliferation of glia (Johnson et al., 2000; Quigley et al., 2000). Besides, the axonal transport of TrkB is obstructed in a model of glaucoma (Pease et al., 2000b). Thus, rescue of obstructed retrograde transportation of neurotrophins is considered as a promising method to cue glaucoma, albeit a few studies state that obstructed neurotrophin transportation hypothesis is not valid enough based on some immunostaining or in-situ hybridization experiments (Guo et al., 2009).

Based on previous research, several neurotrophic pathways have been studied related with experimental glaucoma progression, including TrkA-NGF signaling (Shi et al., 2007; Sposato et al., 2008), TrkB-BDNF signaling (Guo et al., 2009; Iwabe et al., 2007; Pease et al., 2000a), TrkC and p75 signaling (Bai et al., 2010a). Besides, microglia functional change during glaucoma progression have been focused on recently (Srinivasan et al., 2004). Anyway, the neurotropic pathway will be the key breakthrough in the therapy of glaucoma, which assists the axon regeneration and the function recovery of RGCs of which abnormality is recognized as the key reason related with glaucomatous damage of retina, brain nucleus, and regions, and even functional shift of whole brain (Frezzotti et al., 2014; Georgiou et al., 2010; Williams et al., 2013). The present disclosure focuses on TrkB-BDNF signaling, which is the major signaling pathway for survival and neurite outgrowth of RGCs (Guo et al., 2009; Iwabe et al., 2007; Pease et al., 2000a), albeit other factors are also very important. This signaling pathway is comparatively clear and not mixed up with other non-neuronal cell types, like microglia. Based on previous neurotrophin transportation obstruction hypothesis for glaucoma progression (Guo et al., 2009; Iwabe et al., 2007; Pease et al., 2000a), the endocytosis of TrkB in the terminal of RGCs plays a role in neuron survival. The present disclosure provides herein TrkB agonist antibodies or the antigen-binding fragments thereof functions similarly or more effectively than BDNF in preventing, treating, relieving, delaying the onset of or reducing the risk of developing into glaucoma.

Stroke

Stroke is a neurovascular disease caused by burst or clot of blood vessels of the brain. It is a global health issue and in China the No. 1 killer. Each year, about 2.5 million people get stroke and more than 1.6 million die of this disease. Due to the high density of brain capillaries, stroke can occur in any region of the brain that leads to various sequelae, the most common among all is hemiplegia. Thus, research into treatment of this disease is in urgent need.

Major mechanisms of ischemic stroke include failure of ATP-dependent ion channels, calcium overload, excitotoxicity, free radical genesis, apoptosis and immune response. Due to the complexity of these interacting pathways, a target that regulates cell survival and promote neurogenesis in a rather long treatment window, such as TrkB, might be a promising target.

It is reported that BDNF effectively reduces infarct volume and cell death and improves behavioral outcomes in stroke models. On the contrary, blockade of the BDNF-TrkB pathway deteriorates the disease. Besides the regulation of cell survival, BDNF also promotes axonal growth, improve synaptic function and accelerates neurogenesis, differentiation and migration. This indicates BDNF could prolong the treatment window to several days post stroke. The present disclosure provides herein TrkB agonist antibodies or the antigen-binding fragments thereof functions similarly or more effectively than BDNF in preventing, treating, relieving, delaying the onset of or reducing the risk of developing into stroke.

Methods of Use

The present disclosure further provides methods of using the TrkB agonist antibodies or the antigen-binding fragments thereof.

In some embodiments, the present disclosure provides methods of treating a TrkB associated condition in a subject, comprising administering to the subject a therapeutically effective amount of the antibody or the antigen-binding fragments thereof. In certain embodiments, the subject has been identified as having a disorder or condition likely to respond to a TrkB agonist. In certain embodiments, the present disclosure provides methods of preventing, detecting, or diagnosing TrkB associated condition, comprising contacting the TrkB agonist antibody or the antigen-binding fragments thereof provided herein with a biological sample obtained from a subject suspect of or having or at risk of having the TrkB associated condition and determining the level of TrkB agonist antibody or the antigen-binding fragments thereof that binds to TrkB in the biological sample.

For the treatment of the TrkB associated condition, the subject is tested as positive for TrkB expression, or tested as having elevated level of TrkB expression. Various methods can be used to determine the presence or level of TrkB in a test biological sample from the individual. For example, the test biological sample can be exposed to TrkB agonist antibody or antigen-binding fragment thereof, which binds to and detects the expressed TrkB protein. Alternatively, TrkB can also be detected at nucleic acid expression level, using methods such as qPCR, reverse transcriptase PCR, microarray, SAGE, FISH, and the like. In some embodiments, a biological sample is derived from a cell or tissue (e.g. biopsied tissue from an organ), tumor cells, or bodily fluid (e.g. blood or serum). In certain embodiments, the presence or upregulated level of the TrkB in the test biological sample indicates the likelihood of responsiveness. The term "upregulated" as used herein, refers to an overall increase of no less than 10%, 15%, 20%, 25%, 30%, 35%, 40%, 45%, 50%, 55%, 60%, 65%, 70%, 75%, 80% or greater, in the protein level of TrkB in the test sample as detected using the antibodies or antigen-binding fragments provided herein, as compared to the TrkB protein level in a reference sample as detected using the same antibody. The reference sample can be a control sample obtained from a healthy or non-diseased individual, or a healthy or non-diseased sample obtained from the same individual from whom the test sample is obtained, or a sample obtained from the same individual at an earlier time point during the treatment of the condition. For example, the reference sample can be a non-diseased sample adjacent to or in the neighborhood of the test sample.

The antibodies or antigen-binding fragments disclosed herein may be administered alone or in combination with one or more additional therapeutic means or agents. For example, the antibodies or antigen-binding fragments disclosed herein may be administered in combination with a second therapy, such as radiation therapy, chemotherapy, targeted therapies, gene therapy, immunotherapy, hormonal therapy, angiogenesis inhibition, palliative care, surgery for the treatment of cancer (e.g., tumorectomy), one or more anti-emetics or other treatments for complications arising from chemotherapy, or a second therapeutic agent for use in the treatment of any medical disorder mediated by TrkB, for example, another neurotrophin such as BDNF, neurotrophin-3 (NT-3), NT-4/5, nerve growth factor (NGF), ciliary neurotrophic factor (CNTF), glial cell line-derived neurotrophic factor (GDNF), another antibody, therapeutic polynucleotide, chemotherapeutic agent(s), anti-angiogenic agent, cytokines, other cytotoxic agent(s), growth inhibitory agent(s). In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

In some embodiments, the method of using the antibody and the antigen-binding fragment thereof includes a method of preventing cell apoptosis and/or necroptosis or enhancing cell survival. In one embodiment, the method comprises contacting the antibody or the pharmaceutical composition provided herein with a biological sample expressing TrkB.

In some embodiments, the method of using the antibody and the antigen-binding fragment thereof includes a cell-based therapy for treating or reducing the risk of a TrkB associated conditions in a subject. In one embodiment, the method comprises administering to the subject a cell, wherein the cell expresses on its cell surface the antibody or the pharmaceutical composition provided herein.

The method for engineering cells to express the antibody provided herein has been described in earlier sections. Suitable cells that can be engineered to express the antibody and used in the cell-based method can be any cells compatible with transplantation and cell therapy. In some preferred embodiment, the cells are derived from the subject that receives the therapy. In some embodiment, the cells are derived from the pluripotent cells from the subject. In some embodiment, the pluripotent cells are induced pluripotent cells (iPS).

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Materials and Methods

1. Production of Mouse Monoclonal Antibody by Hybridoma Technology (1) Antigen Preparation The coding sequence of TrkB extracellular domain was cloned into the Pfastbac vector containing a signal peptide, and protein was purified using the insect sf9 cell line. Two kinds of protein with different tags were prepared: TrkB-ECD-hFc for immunizing animals, and TrkB-ECD-His used as screening antigen.

(2) Animal Immunization

The antigen (recombinant TrkB-ECD-hFc) was dissolved in DPBS and used to immunize BALB/C mice of about 6~8 weeks old via subcutaneous route for all injections. During the fast immunization procedure, those mice were immunized for about 8 times.

(3) Lymphocyte Cell Isolation

After immunization, animals were selected for harvest by titer ELISA testing. Briefly, the serum from immunized mice or naïve mice were added into the ELISA plate coating with TrkB-ECD-his protein. The titer of each mice was determined from the optical density at 450 nm. Immunized mice were sacrificed and lymph nodes were harvested. Those lymphoid cells were suspended in DMEM before fusion with a myeloma cell line Sp2/0-Ag14.

(4) Cell Fusion

Lymphoid cells were fused with Sp2/0-Ag14 mediated by PEG (P7306, sigma). Then the fused cells were suspended in HAT selecting medium (21060-017, Gibco). Hybridoma could tolerate the selected medium with the ability of infinite proliferation. On day 7 or 10, one-half medium was changed.

(5) Hybridoma High Throughput Screening and Subcloning

After about 14 days of selected culture, hybridoma supernatant were screened for TrkB-specific monoclonal antibodies. ELISA was used for analyzing the affinity of the antibodies, and NFAT assay was used for selecting active TrkB agonists. After selection of positive cell pools, subcloning was done by classical limiting dilution.

(6) Monoclonal Antibody Isotype Identification and Hybridoma Sequencing

ELISA Kit (BAT0296, Sino) was used to identify the isotype of the monoclonal antibodies. Hybridoma sequencing was performed with 5'RACE kit (cat.634858 & 634859, Clontech).

2. Production of Rabbit Monoclonal Antibody by Yeast Display

The antigen (recombinant human TrkB-ECD) was dissolved in DPBS and used to immunize rabbit of about 6~8 weeks old via subcutaneous route for all injections. After immunization, animals were selected for B cell preparation by titer ELISA testing. Immunized rabbits were sacrificed and lymph nodes were harvested. The B cell immunoglobulin repertoire of the immunized rabbit was immortalized by the combinatorial cloning of the rearranged variable domains of tight (V-L) and heavy (V-H) chains, which was introduced into the yeasts and displayed on the yeast surface as the single chain FV (scFV). Affinity selection of the scFV antibodies with FACS was followed by reconstructing them into the complete template of the IgG antibody. The further screening for agonist antibody was carried out with NFAT assay. Exemplary rabbit monoclonal antibodies are TrkB-agoAb202 and TrkB-agoAb203.

3. Protein Expression and Purification

The gene fragments of TrkB-ECD430 (corresponding to amino acid sequence from 30-430, namely the full-length extracellular domain) and TrkB-ECD365 (corresponding to amino acid sequence from 30-365, D1-D5 of the extracellular domain without the extracellular juxtamembrane (EJM) region) of the human TrkB gene (accession number S76473.1) were cloned into pFastBac Dual with 6×His tags on the C terminal. Baculovirus containing the above TrkB-ECD genes was produced using the Bac-to-Bac system from Invitrogen. After infecting the SF9 cells, the culture was incubated at 27° C. in the MSF1 media.

After 72 hours of incubation, supernatant of the culture was collected and centrifuged under 4° C. at 4,000 rpm for 20 min. The supernatant was sonicated to break the cell membranes. It was further centrifuged at high speed and the supernatant was used for protein purification. Nickel column (70501-5, Beaver) and molecular sieve were used for protein purification. The nickel column was balanced with 1×TBS buffer before loading the supernatant containing target proteins. While the target protein binds the column specifically, non-specific proteins were washed away by buffer. The target proteins were eluted with concentrated imidazole buffer. The eluent was then loaded onto the molecular sieve where high-molecular-weight proteins were eluted earlier than the low-molecular-weight proteins. We applied Superdex200 (17517501, GE) in target protein purification.

4. NFAT

Experiments were carried out following the protocol provided by CHO-hTrkB NFAT kit (K1095, Life Technologies). The day before experiment, CHO-hTrkB cells (K1435, Life Technologies) were seeded in 384-well plates with 32 μl media. After 5 hours of BDNF or TrkB-AgoAb treatment at 37° C., the culture was incubated for 2 hours at room temperature with 8 μl substrate. Signals were obtained with the microplate reader (Envision, PerkinElmer).

5. AlphaLISA

Lyse the cells as previously described. In white opaque plates, 10 μl donor bead (6760617M, PerkinElmer) and 10 μl biotinylated anti-TrkB monoclonal antibody (BAF397, R&D) were added in each well and incubate for 30 min at 37° C. under subdued light. 10 μl lysate, 10 μl anti-TrkB antibody (ab51187, Abcam) and 10 μl acceptor beads (6760617M, PerkinElmer) were added into the according wells and incubated for 1 hour at 37° C. under subdued light. Signals were measured with Envision (PerkinElmer) and analyzed afterwards.

6. Delfia

Coat anti-pTrkB antibody (4621S, CST) in carbonate buffer (pH 9.2) to Microplate-96 well (163320, NUNC). Incubate the plates at 4° C. overnight. Wash the plates twice. Block the plates with blocking buffer at 37° C. for 2 hours. Then wash the plates twice with PB ST.

Detection: Add 50 µl lysates to 1st Antibody coated plate. Incubate the plate at room temperature (RT) for 2 hours with slow shaking. Add 50 µl/well 4 µg/ml Biotin Goat-anti TrkB antibody (BAF397, R&D) in Lysis buffer (CST) to the plate. Incubate the plate at RT for 1 hour with slow shaking. Then wash the plate 3 times. Remove wash buffer thoroughly, and add 100 l/well 200 ng/ml Eu-labeled Streptavidin (1244-360, Perkinelmer) in the assay buffer. Incubate the solution at RT for 30 mins with slow shaking. Then wash the plate 5 times. Add 50 µl/well Enhancement solution followed by 10-minute incubation with slow shaking. Detect at Envision with defaulted DELFIA protocol.

7. Biacore (SPR) (Biacore T200, GE)

Wash CM5 chip in PBS with sonication. Replace the buffer of candidate antibodies and the target protein with the same PBS. The target protein was diluted to 1 µg/µL as the solid phase and the candidate antibodies were serial diluted to 7 dilutions as the fluid phase. After obtaining the signal, Biacore Evaluation Software was used to create fitting curves. ch2<Rmax/10 indicates good confidence level.

8. Primary Hippocampal Neuron Culture and Treatment

Cortex were separated from embryonic day(E)18 SD rat in HBSS, then peeled off arachnoid, and dissected hippocampus in digesting medium (0.125% typsin, Invitrogen, 15050065). After 20 min digestion at 37° C., the reaction was stopped by complete medium (DMEM medium supplemented with 10% FBS and GlutaMax, Gibco). The tissue were triturated gently until cloudy, and settled for a few minutes. The cloudy supernatant was transferred to another tube. This step was repeated until tissue disappeared. The suspensions were mixed and the cells in suspension were counted using hemocytometer. Neurons were plated on 100 ng/ml poly-D-lysine-coated (Sigma, 030M5021V) diameter 3.5 cm plates at 1000,000 cells/well. After 4-6 h incubation, complete medium was aspirated completely and replaced with maintenance medium (neurobasal medium supplemented with B27 and GlutaMax, Gibco). Maintenance medium were half-changed with maintenance medium every 3 days. Neurons were cultured for 10-14 days and then processed for BDNF or TrkB-AgoAb stimulation.

9. Cell Line Culture

All the cells were incubated in 37° C., 5% $CO_2$ cell incubator. CHO cell were cultured in FK-12K medium (21127-022, Gibco) supplemented with 10% FBS (16000044, Life technology). PC12 cell were cultured in DMEM medium supplemented with 5% FBS, 10% horse serum (HS). SH-SY5Y cell were cultured in RPMI1640 medium supplemented with 15% FBS. The complete medium of primary neurons were DMEM medium supplemented with 10% FBS and 1% GlutaMAX-I (35050061, Gibco). Maintenance medium of primary neurons were NeuroBasal (10888022, ThermoFisher Scientific) medium supplemented with 2% B-27 and 1% GlutaMAX-I. All these mediums were supplemented with 0.2% penicillin and streptomycin. CHO-hTrkB were cultured in the medium added 5 µg/mL Blasticidin (R210-01, Invitrogen). When cell passaged, HBSS were used to wash off the medium, and 0.05% EDTA trypsin were used to digest cells. Then plated cells on plate for experiment or maintenance.

10. Cell Transfection

We transfected cell using Lipofectamine2000 kit (11668-019, Invitrogen) and all the operation followed the instruction. The cell concentration were about 90%. Opti-MEM (31985-070, Invitrogen) was used to dilute plasmid and Lipofectamine 2000 (11668-019, Invitrogen), respectively, then we added diluted plasmid to diluted Lipofectamine2000 gently and incubated for 30 min at room temperature. Finally we added the mixture to cell medium and mixed gently. The transfected cell were incubated in incubator for 24 h.

11. SDS-PAGE and Western Blotting

Cell were washed by cold PBS for 3 times and were lysed in buffer containing 50 mM Tris-HCl (pH 8.0), 250 mM NaCl, 1% NP-40, 0.5% deoxycholate, 0.1% SDS, and protease inhibitors (Roche Diagnostics) for 30 min on ice. After centrifugation to remove insoluble material, the proteins inlysate were separated using 10% SDS-PAGE, and transferred to a PVDF membrane (Immobilon-P, Millipore). Membrane was blocked with 5% BSA in Tris buffered saline with 0.1% Tween (TBST) and incubated overnight at 4° C. with antibody diluted in 5% BSA in TBST, with gentle shaking. Membranes were washed with TBST, incubated with secondary antibodies, washed first with TBST and then with TBS, and developed with SuperSignal West Pico Chemiluminescent substrate (34080, Pierce).

12. Co-Immunoprecipitation

Cell were washed by cold PBS for 3 times and were lysed in buffer containing 50 mM Tris-HCl (pH 8.0), 250 mM NaCl, 1% NP-40, 0.5% deoxycholate, 0.1% SDS, and protease inhibitors (4693132001, Roche) (Roche Diagnostics) for 20 min on ice. After centrifugation to remove insoluble material, the proteins in lysate incubated with target protein over night at 4° C. 20 µl Protein A beads (sc-2003, Santacruz) were added to the protein mixture. After these mixture incubated for 4-5 h at 4° C., we washed beads for 3 times with lysis buffer. Then the supernatant was removed and 20 µl loading buffer was added to the deposit beads. The beads coupled proteins were denatured and uncoupled by 95° C. heat for 10 min.

13. Motor Neuron Culture and Cell Death Assay

E13 pregnant mouse was euthanatized by cervical dislocation. The embryos were carefully removed from the uterus and kept in ice-cold HBSS. Decapitate the head and remove the tail with a pair of tweezers. Place the embryo dorsal side up. Remove the outer thin sheath of skin and open the central channel of the spinal cord with a pair of tweezers. Transfer the isolated spinal cord to a new neurobasal medium-containing dish and place the spinal cord with the dorsal upwards. Remove the dorsal root ganglia (DRG) and the ensheathing meninges. Then chop the isolated spinal cords into small pieces, and incubate for 20 min at 37° C. in digestion solution (papain and DNase in neurobasal medium). Spin down and discard digestion solution, gently triturate cell aggregates with a 5 mL pipette in fresh neurobasal medium. The resulting suspension was first centrifuged for 5 min at 600 rpm at RT to remove cell debris. Then motoneurons were enriched using Optiprep (D1556, Sigma, USA)-based density gradient centrifugation modified from published protocol by Graham (Graham, 2002). The supernatant was discarded, the pellet was resuspended in HBSS, and the suspension was layered over a cushion of 3 mL 10.4% (w/v) Optiprep and centrifuged for 400×g 25 min, at RT. The top layer enriched in motoneurons was collected, then add 10 mL neurobasal medium and then centrifuged for 10 min at 1200 rpm at RT to collect cells. The cell pellet was finally suspended in motoneuron complete medium (10% horse serum, 1× B27, and 1× glutaMAX in neurobasal). Plate an appropriate number of cells on PDL and laminin-coated dishes or coverslips. After cells have attached to the surface of the culture dish, carefully replace the medium with complete medium (containing neurotrophic factors or antibodies).

Cell death was assayed using in situ cell death detection kit (11684795910, Roche) following instruction. Briefly, cells were fixed with 4% PFA in PBS for 20 min and permeabilized, then incubated in TUNEL reaction solution. ChAT and fluorescein double labeled cells were scored using high content scan and analysis system.

14. Immunocytochemistry

Cholinergic motoneurons can be identified by high expression level of choline acyltransferase (ChAT) (Camu & Henderson, 1992), distinct from other spinal cells. Cells were fixed with a 4% solution of PFA in PBS for 20 min, and immunostaining was carried out following standard protocol with a goat anti-ChAT antibody (AB143, Merk Millipore, USA). The purity of a culture was assessed by determining the percentage of immunolabelled cells. Usually. Neurite number and length were determined after immunolabelling cells with an antibody against neuronal class III b-tubulin (AT-809, Beyotime Biotechnology, China). Neurite length was measured using high content scan and analysis system (ArrayScan VTI 700, Thermo, USA), following neuronal profile V4 protocol.

15. Purification and Culture of Mouse RGCs by Immunopanning

Postnatal 7 days Mice retinas were dissected in 4° C. DPBS (Gibco, 14040-216). Digesting retinas in papain (Worthington Biochemical LS003126) solution (papain 50 μL in 10 mL DPBS, DNase 0.4%, L-cysteine (Sigma-Aldrich C7477) adjusting pH to 7.4 by 10 μL 1M NaOH) in 37° C. Remove papain solution and resuspend cells in low-ovo solution and high-ovo solution separately before centrifugation with 1000 r/min 12 min 25° C. Low and high-ovo 10× stocks are prepared with 3 g BSA (Sigma-Aldrich A8806)+3 g trypsin inhibitor (Worthington LS003086) or 6 g BSA+6 g trypsin inhibitor dissolved in 200 ml DPBS, and adjusting pH to 7.4.

Resuspend the cells in panning buffer (18 mL of D-PBS, 2 mL of 0.2% BSA, and 57 μL of insulin (Beyotime P3376)) and conduct panning in the negative panning plated coated with BSL-1 solution (BSL-1 (Vector Labs L-1100) 20 μL of BSL-1 and 20 mL of D-PBS) overnight in 4° C. The non-binding cells are collected after 30 min with shaking gently every 15 min. In the same way, the secondary negative panning is lasting 10 min or until RGCs are seen linked to the plate. The collected cell suspension will go through positive panning plate coated with secondary antibody goat anti-mouse IgG+IgM (H+L) (Jackson ImmunoResearch 115-005-044) (1:250) in 4° C. and coated with primary antibody Mouse anti-mouse Thy1.2 (CD90) IgM (Serotec MCA02R)(1:1000) after and before rinsed the plate three times with DPBS.

Add 100 μL of trypsin stock to 4 mL of warmed EBSS after panning for 4 min in 37° C. cell incubator. Transfer cells into 20 mL universal tube and add 4 ml FBS solution (30% FBS in DPBS) to stop trypsinization. Centrifuge cells in 1000 r/min 12 min 25° C. and resuspend cells in RGC growth media. Plating in 96 wells plates with 100 μL cell suspension each. The 96 wells plate is coated with the 100 μL each/well mouse laminin solution (laminin (1 mg/mL) to a final concentration of 50 μg/mL by adding 10 μL of laminin stock to 5 mL of Neurobasal medium) and PDL solution (1 mg/mL; 100×) in a 37° C. incubator overnight.

16. Neuron Survival Assay by RGCs Culture

RGCs survival rate are conducted in DIV7 primary culture by ArrayScan® VTI HCS Reader (Thermo, ArrayScan VTI 700). DIV7 primary culture is fixed by PFA (4%) and immunostained by DAPI, Brn3a, and Tuj-1. Survival RGCs can be recognized by morphology of neurons. Each well of 96 well plates is plated with about 30,000 RGCs after panning, and feed the cells every other day with renew half volume of medium and treat with different medicine, including BDNF 1 nM, CNTF 1 nM, Forskolin 5 μM or these substrates mix in parallel 5 wells.

17. Spinal Root Avulsion Injury

Adult female Sprague Dawley (SD) rats (250 to 300 g body weight, 70 to 90 days old) were used in this study. Animals were anaesthetized with a mixture of ketamine (80 mg per kg of body weight) and xylazine (8 mg per kg), by intraperitoneal injection. The right spine segments from the 5th to the 7th cervical (C5-C7) were exposed. A dorsal laminectomy was performed on lamina C6 to expose the C7 dorsal root. After opening the dura matter, the right side C7 roots (both dorsal and ventral) were avulsed using a fine glass hook. Another cut was made on the distal C7 spinal nerve and the disconnected C7 dorsal and ventral roots, together with a small fragment of spinal nerve, were removed. Immediately, a gelfoam soaked with 5 μg BDNF, 5 μg TrkB agonist or same volume of PBS were gently placed onto the injured spinal cord surface. After that, an osmotic minipump, filled with the same solution as in the gelfoam, was embedded subcutaneously near the injury site. The pump was connected with a tube, which leads the released drugs to the injured spinal cord surface. Grouping and sample sizes were shown below:

1) Sham (N=7):
no avulsion+gelfoam (with 5 μl PBS)+pump (releasing 12 μl PBS per day)
2) PBS treated negative control (N=7):
C7 avulsion+gelfoam (with 5 μl PBS)+pump (releasing 12 μl PBS per day)
3) BDNF treated positive control (N=8):
C7 avulsion+gelfoam (with 5 μg BDNF)+pump (releasing 1 μg, 12 μl BDNF per day)
4) TrkB Agonist (low concentration) (N=8)
C7 avulsion+gelfoam (with 5 μg TrkB Agonist)+pump (releasing TrkB Agonist 1 μg, 12 μl per day)
5) TrkB Agonist (high concentration) (N=8)
C7 avulsion+gelfoam (with 5 μg TrkB Agonist)+pump (releasing TrkB Agonist 6 μg, 12 μl per day)

Perfusion and sectioning of ventral spinal cord C6-C8 were performed at a thickness of 20 μm. Every four sections of the ventral spinal cord was applied for Nissl staining. Only those with a clear nucleus and the cellular diameter over 30 μm were counted as motoneurons.

18. Paramagnetic Beads Glaucoma Mouse Model

Before intraocular injection of paramagnetic beads (20160000-1, bioWORLD), RGCs should be labeled by fluorescent markers. We choose 4% Fluorogold (AB153, Merck Millipore) solution for retrograde labeling by bilateral brain stereotactic injection in superior colliculus. The site location is 6.0 mm behind Bregma, 1.0 mm lateral, and depth 4.5 mm, with each side 1 μL by 33G steel needle. After the surgery, mice should rest in homecage for two weeks before intraocular injection. We use a 30-gauge needle to conduct intraocular injection of paramagnetic beads (Samsel et al., 2011). In less than 2 min, we used the needle to punch through cornea behind the corneoscleral limbus in 45° angle 2 mm in depth of vitreous body in order not to damage lens. 20 µL paramagnetic beads are injected into the anterior chamber of the one side eye, delivering approximately 0.3-0.6 mg of beads. The paramagnetic beads should be guided to the anterior angle by magnet. The other side eye will be injected with 20 µL saline to make negative control.

Example 2

Generating and Screening Monoclonal TrkB Agonist Antibodies

The monoclonal TrkB antibodies were generated by hybridoma technology. The first step of monoclonal antibody (MAb) production is to stimulate the animal immune system with antigen. It was done using a fast immunization protocol (referred in methods), with the antigen of TrkB-ECD (extracellular domain) in mice (see SEQ ID NO: 1). The hybridoma clones were made by fusing lymphocytes from the immunized mice with mouse myeloma cells. Hybridoma supernatant were screened for TrkB-specific monoclonal antibodies with the enzyme-linked immunosorbent assay (ELISA), and then screened for the agonist antibody with NFAT assay. After determining the culture supernatants with TrkB activating effect, the clones were subcloned into monoclonal cell lines. Finally, all the subclones were screened again for positive ones with ELISA and NFAT assay. These desirable and stable clones were grown in large quantity for production of sufficient amounts of antibodies. After purification of the antibodies, the isotype of these purified antibody were identified below in Table 1.

TABLE 1

Monoclonal TrkB agonist antibodies

| TrkB antibody | Isotype | Species |
|---|---|---|
| TrkB-agoAb1104 | IgG1 | Mouse |
| TrkB-agoAb202 | | Rabbit |
| TrkB-agoAb101 | | Mouse |
| TrkB-agoAb303 | | Mouse |
| TrkB-agoAb203 | | Rabbit |
| TrkB-agoAb2908 | IgG1 | Mouse |
| TrkB-agoAb5702 | IgG1 | Mouse |
| TrkB-agoAb1016 | IgG1 | Mouse |
| TrkB-agoAb2037 | | Mouse |
| TrkB-agoAbB901 | IgG2 | Mouse |
| TrkB-agoAbB503 | IgG3 | Mouse |
| TrkB-agoAbB418 | IgG3 | Mouse |
| TrkB-agoAb6916 | | Mouse |
| TrkB-agoAb4014 | | Mouse |
| TrkB-agoAb104 | | Mouse |
| TrkB-agoAb7431 | IgG1 | Mouse |
| BDNF | | |

Example 3

Antibody Characterization-Biochemistry 3.1 Specificity

TrkB agonist antibodies can bind to TrkB specifically but not bind to TrkA, TrkB, TrkC or P75 in ELISA assay. Data of exemplary antibodies TrkB-agoAb104, TrkB-agoAb202, TrkB-agoAb203, TrkB-agoAb303, TrkB-agoAb1104 and TrkB-agoAb2908 are shown in FIG. 1A-1F. 500 µl of 1 g/ml protein was coated on each well of the plate, and 5 µL of 10 nM, 1 nM or 0.1 nM antibody was added to perform ELISA assay.

3.2 Affinity

Biacore was used to analyze the affinity of antigen-antibody interaction. The data is shown as below in Table 2.

TABLE 2

| Antibody | Rmax (RU) | Chi2 | KD (M) |
|---|---|---|---|
| TrkB-agoAb104 | 29.44 | 0.725 | 6.684E−11 |
| TrkB-agoAb203 | 42.59 | 2.58 | 5.287E−11 |
| TrkB-agoAb303 | 14.78 | 0.938 | 4.019E−9 |

3.3 Antigen Epitope Identification

Five extracellular domain truncated TrkB constructs were designed as shown in FIG. 2A and transfected to 293T cell for expression respectively. The lysate were collected. Immunoprecipitation was used to test the antibodies that cannot bind to truncated TrkB conjugated with GFP (see FIG. 2B). The results suggested that D1 and D2 domains may be necessary for TrkB-agoAb202 antibody binding to TrkB. The others such as TrkB-agoAb418 antibody may bind to D5 domain. Δ1 lacks D1 domain (represented by Cys 1), Δ2 lacks D1 and D2 (represented by LAM) domains, Δ3 lacks D1-D3 (represented by Cys 2) domains, Δ4 lacks D1-D4 (represented by Ig1) domains, and Δ5 lacks D1-D5 (represented by Ig2) domains. "TM" represents transmembrane domain, "C" represents control (blank, empty vector). FL represents full length gene (WT). The target binding domains of TrkB for TrkB agonist antibodies provided herein are shown in Table 3.

TABLE 3

| TrkB antibody | Binding domain |
|---|---|
| TrkB-agoAb1104 | D1 |
| TrkB-agoAb202 | D1 |
| TrkB-agoAb101 | Not known |
| TrkB-agoAb303 | D3 |
| TrkB-agoAb203 | D5 |
| TrkB-agoAb2908 | D5 |
| TrkB-agoAb5702 | D5 |
| TrkB-agoAb1016 | D5 |
| TrkB-agoAb2037 | D5 |
| TrkB-agoAbB901 | D5 |
| TrkB-agoAbB503 | D5 |
| TrkB-agoAbB418 | D5 |
| TrkB-agoAb6916 | D5 |
| TrkB-agoAb4014 | D5 |
| TrkB-agoAb104 | JM |
| TrkB-agoAb7431 | JM |
| BDNF | D5 |

Figure 3:
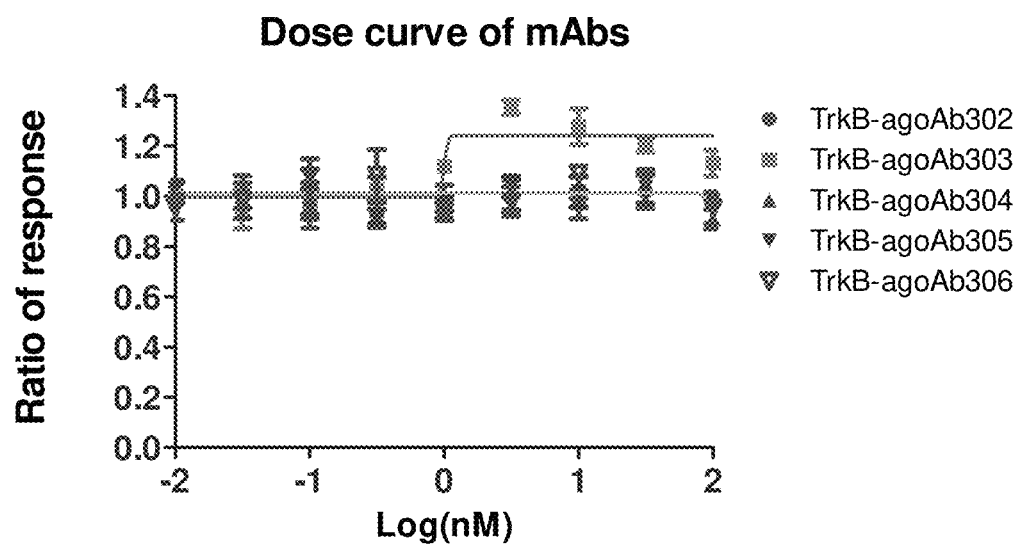
FIG. 3 shows the activation of TrkB by the TrkB-agoAbs as measured by Alphalisa.

In the experiment of Alphalisa to evaluate degree of competition of the antibody with BDNF, saturated BDNF solution (10 nM) was used together with a series of antibody solutions diluted from 0.01 to 100 nM to treat CHO cells stably transfected with TrkB (TrkB-CHO cells). When the antibody competitively binds to TrkB, the activation induced by 10 nM BDNF together with high concentrations (such as 10-100 nM) of the antibody might not be as strong as the effect induced by 10 nM BDNF alone (competitive effect), since BDNF is usually more effective in activating TrkB than antibodies. However, if BDNF plus antibody could induce stronger TrkB activation than BDNF alone, the antibody shows an additive effect or potentiation. We have now found that TrkB-agoAb303 exhibits this feature (see FIG. 3).

3.4 TrkB Activation-Try515 Phosphorylation

Figure 4:
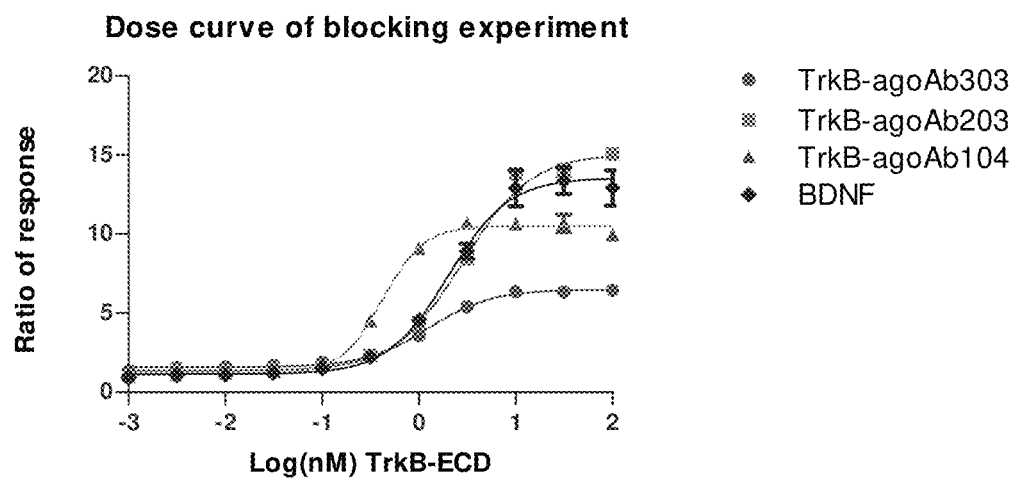
FIG. 4 shows the Try515 phosphorylation of TrkB by TrkB-agoAbs (TrkB-agoAb303, TrkB-agoAb203, TrkB-agoAb104) and BDNF, respectively, as measured by AlphaLISA method.

TrkB agonist antibodies can activate the tyrosine kinase of TrkB that phosphorylate the tyrosine residue of TrkB intracellular domain. On account of the most important site which can induce signaling pathway is the Try515 site, we test the Try515 phosphorylation level to indicate the TrkB activation by Alphalisa method which can quantify the strength of phosphorylation. We treated CHO cells transfected with human TrkB (hTrkB-CHO cell) with different concentrations of BDNF or TrkB agonist antibodies for 30 min, and collected the protein samples to test the TrkB phosphorylation level. According to these results the dose curve of BDNF or TrkB agonist antibodies were calculated. The antibodies that were tested are shown in FIG. 4 and Table 4.

TABLE 4

| EC50 tested by Alphalisa method | |
|---|---|
| Antibody | EC50 (nM) |
| TrkB-agoAb104 | 0.42 |
| TrkB-agoAb203 | 2.84 |
| TrkB-agoAb303 | 1.33 |
| BDNF | 1.39 |

Figure 5:
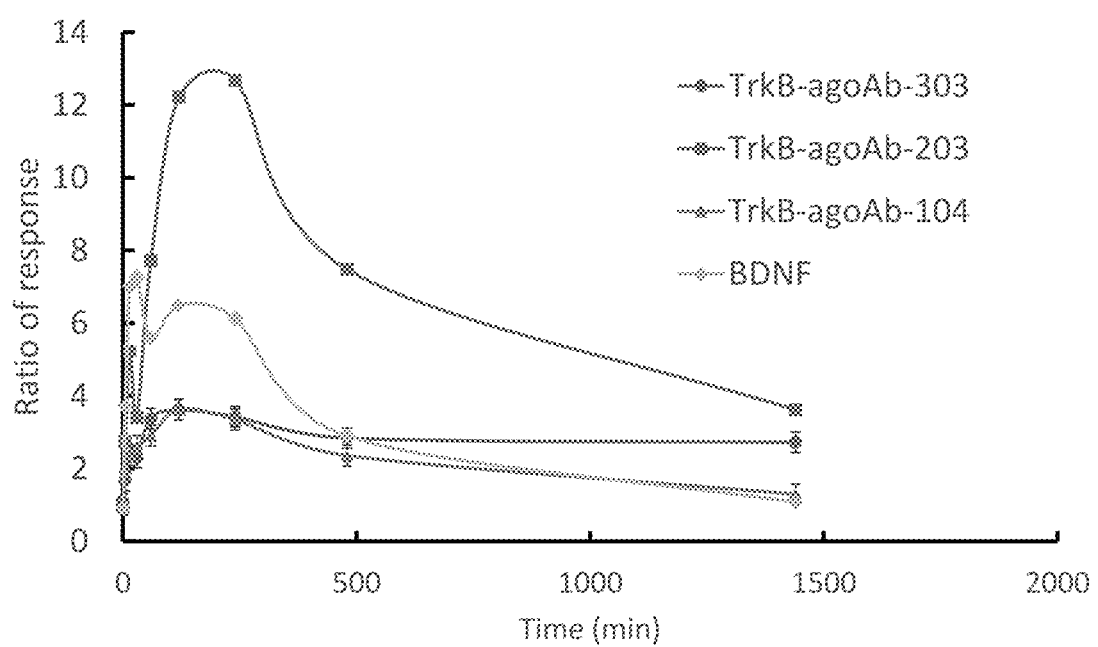
FIG. 5 illustrates a time course curve of the calculated based on the TrkB phosphorylation on Try515. X-axis represents time (minute), and Y-axis represents ratio of response.

According to the dose curves (see FIG. 4), the 50% effective concentration (EC50) were calculated (see Table 4), then we treated cells with the concentrations determined by the value of EC50. Protein samples were collected from the treated cells at different time points to measure the phosphorylation using Alphalisa method and a time course curve was calculated (see FIG. 5). We then calculated the in vitro half life ($T_{1/2}$) by means of the time course curve (see Table 5).

TABLE 5

| Antibody | $T_{1/2}$ (h) |
|---|---|
| TrkB-agoAb104 | 12-24 |
| TrkB-agoAb203 | >24 |
| TrkB-agoAb303 | >24 |
| BDNF | 4-8 |

3.5 TrkB Agonist Antibody Signaling Pathway Activation

Figure 6E:
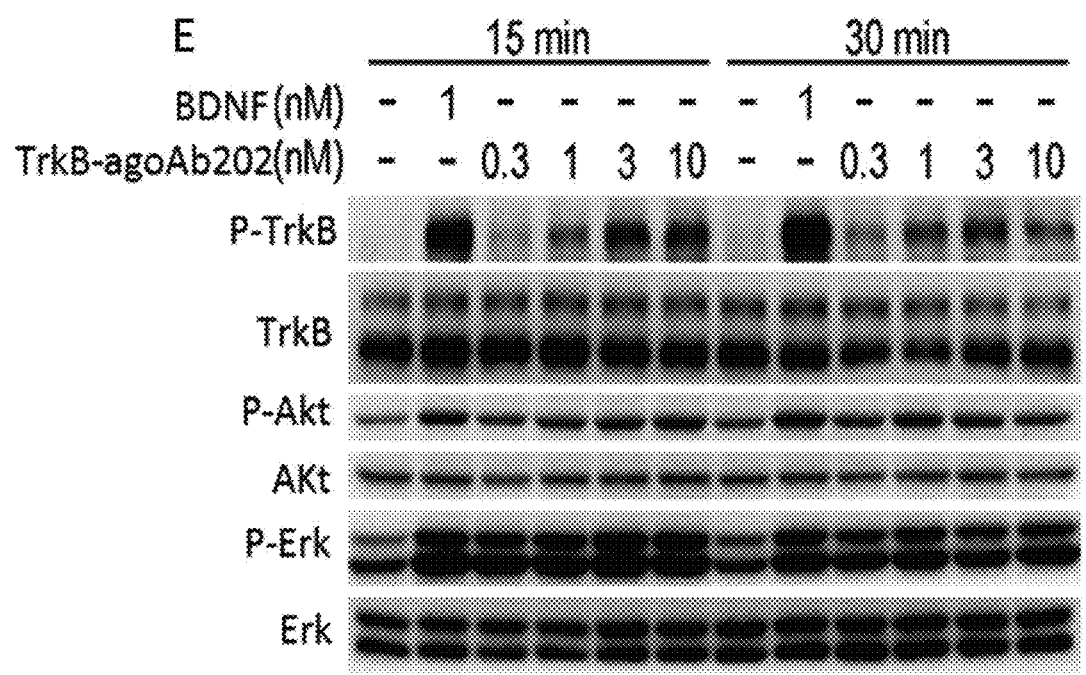

TrkB is activated by intracellular tyrosine residues phosphorylation, and the TrkB activation induces kinase signaling pathways MAPK, PI3K and PLCγ. The phosphorylation level of Erk42/44, Akt, and PLCγ can indicated these three signaling pathways' activation respectively. When hTrkB-CHO cell density reached 60-70%, we treated cell with BDNF (1 nM) or TrkB agonist antibodies (TrkB-agoAb101, TrkB-agoAb104, TrkB-agoAb303, TrkB-agoAb203, TrkB-agoAb202, see FIGS. 6A-6E) and collected samples at different time within 24 hours. The phosphorylation levels of TrkB (Tyr515), Erk44/42 (Thr202/Tyr204), Akt (Ser473) and PLCγ (Tyr783) were tested by western blot. The results showed that TrkB-AgoAb104 can also activate the TrkB signaling pathways as BDNF (see FIG. 6).

Example 4

Antibody Characterization-Cell Biology 4.1 Cell Survival Experiment
4.1.1 PC12 Cell Human TrkB-expressing PC12 cell line were used to conduct the cell survival assay. Human TrkB-PC12 cell were seeded in 96 well plate for 1 day, then the medium was changed to serum free medium which can induce PC12 cell death. BDNF or TrkB-agoAb202 may protect cell from the starved cell death. Caspase3-substrate kit (Promega, G7573) and cellomics array scan were used to quantify the cell survival quality.

4.1.2 Hippocampal Neuron

Aβ (25-35) as a well-known neuronal toxin was used to treat the cultured rat hippocampal neurons to establish AD cell model. According to previous studies, Aβ (25-35) can mimic Aβ (1-42) as the a cell toxin either in vivo or in vitro experiment, therefore we used Aβ (25-35) (GL Biochem) to treat cultured rat hippocampal neurons to establish in vitro AD cell model, and tested the neuron protecting function of the TrkB-AgoAbs. We treated the neurons with different concentrations of Aβ (25-35) for 48 hours, and used Cell titer-Glo kit to test ATP level which indicated the number of living cells. The results showed that the ATP level of 5-40 μM Aβ (25-35) treated cells is about 60-70% to control (Aβ (25-35) untreated hippocampal neurons) (FIG. 7A). Then we used Aβ (25-35) at the toxin concentration at 5 μM because the rescue effect would be better at this percentage of cell death.

In this cell survival experiment, after E18 rat hippocampal neurons were cultured in vitro for 8 days, BDNF or TrkB-AgoAbs (TrkB-agoAb1104, TrkB-agoAb2908 and TrkB-agoAbB901) were added to pretreat for 30 min, then 5M Aβ (25-35) was added into the medium and neurons were further cultured for 48 h. Cell titer-Glo kit was used to test cell survival level. Either TrkB-AgoAbs or BDNF can significantly protect hippocampal neurons at EC50 (see FIG. 7B). ***p<0.001, data are presented as mean±SEM and analyzed with one-way ANOVA.

4.1.3 Motor Neurons

Figure 8:
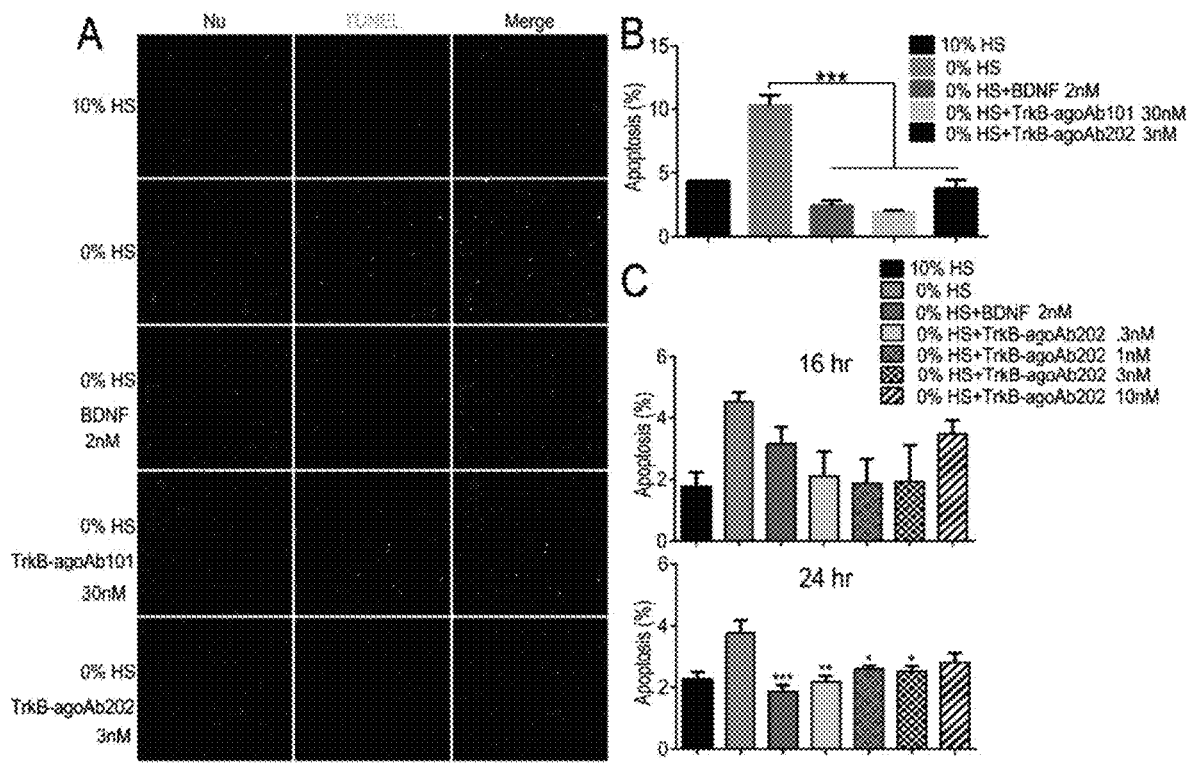
FIGS. 8A-8C indicate the cell viability of motor neurons isolated from mice can be improved by the TrkB-agoAbs at serum deprivation condition.

To investigate the effects of TrkB antibody agonist on motoneurons, an in vitro model was established. Motoneurons were isolated from 13 days old embryonic mice, and cultured in vitro. Serum deprivation has been reported to cause motoneuron death in vitro (Wiese et al., 2010). The motoneurons were cultured for 3 days (DIV 3), then the medium (referred in Method) was replaced with serum (Horse serum, HS)—free medium. Cell viability was estimated by number of remaining cells and percentage of apoptotic cells 16 or 24 hours later. Apoptosis was determined by transferase-mediated deoxyuridine triphosphate-biotin nick end labeling (TUNEL) assay. Consistent with previous report, serum deprivation led to remarkable cell loss and elevated apoptosis (see FIG. 8A-8C). The nucleus (Nu) of the cells were stained with DAPI. More TUNEL-labeled cells were detected in serum-deprived group compared to control that are cultured without serum-deprivation, while BDNF treatment significantly reduced the percentage of apoptotic cells. We tested two agonist antibodies for TrkB, TrkB-agoAb102 and TrkB-agoAb202. Both agonist antibodies showed neuronal protective effects, as demonstrated by reduced apoptosis (see FIG. 8C). *p<0.05, p<0.01, *p<0.001. Data are presented as mean±SEM and analyzed with one-way ANOVA.

4.1.4 Retinal Ganglion Cells

Figure 9:
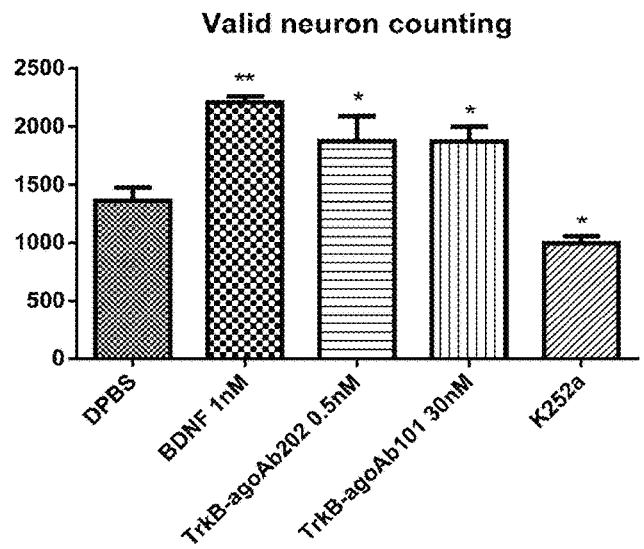
FIG. 9 presents the retinal ganglion cells (RGCs) survival assay using BDNF or TrkB agonist antibodies.

Retinal ganglion cells (RGCs) were prepared from BALB/c mice at postnatal 7 days using immunopanning method. RGCs with purity of 90% were obtained. RGCs will die without the neurotrophic factors, therefore cell survival assay was conducted by adding BDNF and TrkB agonist antibodies. In order to identify the function of selected antibody TrkB-AgoAb102 and TrkB-agoAb202, we preformed RGCs survival assay for functional analysis (see FIG. 9). RGCs are treated separately by BNDF 1 nM (n=6), TrkB-agoAb202 0.5 nM (n=6) and TrkB-agoAb101 30 nM (n=6); DPBS (n=9) as null control and K252a (n=6) as negative control every other day. Treatment with 0.5 nM TrkB-Ago202 or 30 nM TrkB-agoAb101 increased survival rate. *p<0.05, **p<0.01. Data are presented as mean±SEM and analyzed with one-way ANOVA.

4.2 Neurite Out-Growth 4.2.1 PC12 Cell

Human TrkB expression PC12 cell line will be used to perform the neurite out-growth assay. PC12 cells do not have neurite in normal condition, but neurite appears when PC12 cells are stimulated by NGF. Human TrkB-PC12 cells have the same effect after BDNF stimulation. Human TrkB-PC12 cell will be seeded in 96 well plate for 1 day, then the medium will be changed to 1% house serum medium added with BDNF or TrkB-AgoAb. After 72 hour treatment, cells will be tested by cellomics arrays can to quantify the cell neurite.

4.2.2 Hippocampal Neuron

Figure 17:
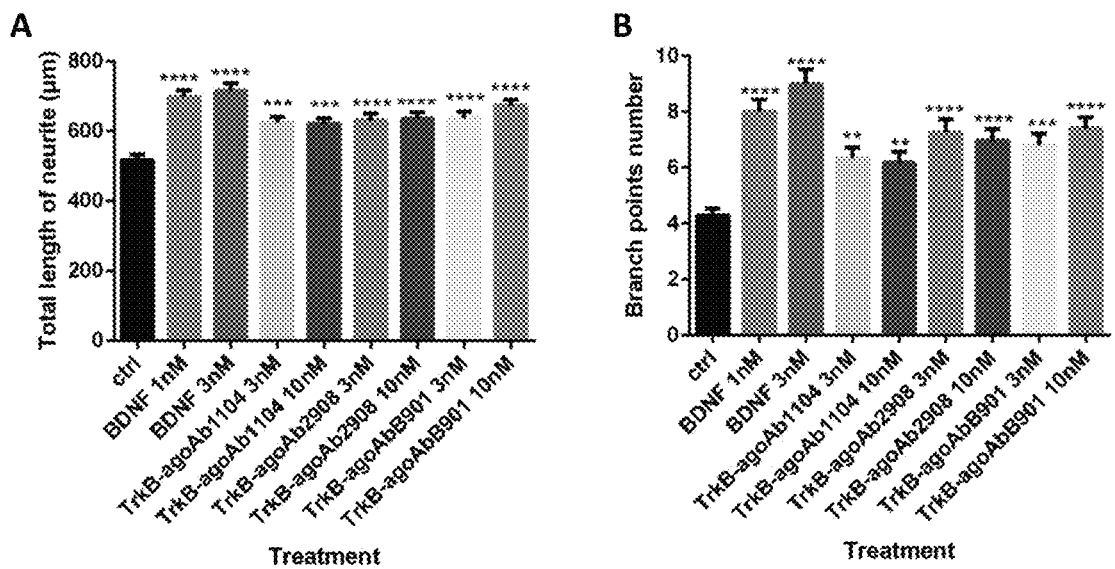
FIGS. 17A and 17B represent hippocampal neuronal neurite outgrowth after adding BDNF or various TrkB antibodies (TrkB-agoAbs).

After E18 rat hippocampal neuron were cultured in vitro for 2 days, BDNF or TrkB-AgoAbs were added to neuron and cultured for another 48 h. We fixed cultures and immunostained the neurons with antibody against MAP2 (Millipore, MAB3418) for morphometric analysis using fluorescence microscope. Neurite growth was quantified by two parameters: total neurite length and number of branch points. Either BDNF or TrkB-agoAbs can increase total length of neurites and branch point number (FIGS. 17A and 17B).p<0.01, *p<0.001, ****p<0.0001. Data are presented as mean±SEM and analyzed with one-way ANOVA.

Example 5

Antibody Characterization-Animal Model 5.1 ALS Animal Model

Figure 10:
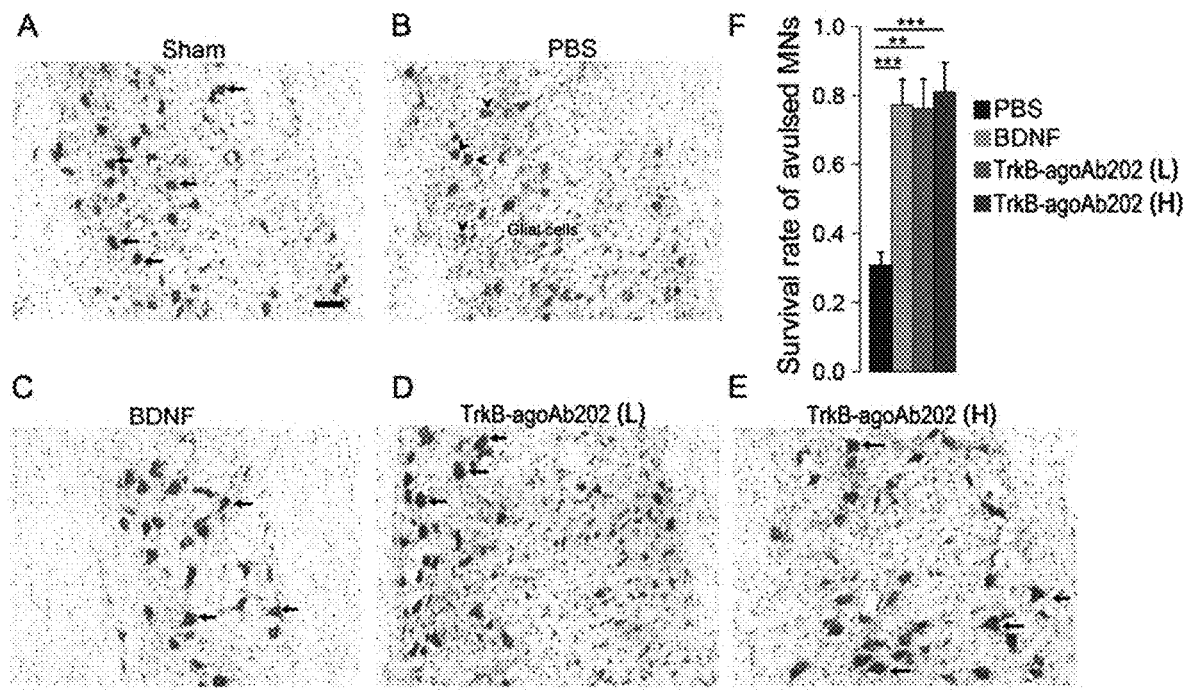
FIGS. 10A-10F show survival rate of avulsed motoneurons in rat ALS model when treated with TrkB-agoAb202 at different concentrations as shown in the experiment protocol in Example 1.

A spinal root avulsion injury was used to mimic the motor neuron injury of ALS. We utilized BDNF and TrkB-agoAb202 to restore the BDNF signaling. Two weeks after avulsion, while only 30.7% of injured motoneurons stayed alive in PBS treated animals, BDNF treatment enabled 77.2% of them surviving. Similar to BDNF, both low (TrkB-agoAb202 (L)) and high (TrkB-agoAb202 (H)) doses (referred in methods) of TrkB agonist demonstrated high efficiency in rescuing lesioned motoneurons, with 76.2% and 80.9% of them surviving, respectively (see FIG. 10F). In addition, in BDNF and TrkB-A treated motoneurons, healthy subcellular architectures including big nuclei, dark stained rough endoplasmic reticulum and big cytoplasm, were well displayed by Nissl staining (see FIGS. 10A, 10C, 10D and 10E). In contrast, abnormal cellular appearances were observed in PBS treated cells, without recognizable subcellular structure. Moreover, a lot of glial cells existed in the gray matter of PBS treated spinal cord (FIG. 10B) but fewer were detected in BDNF or TrkB-agoAb202 treated spinal cord. A few motoneurons from BDNF and TrkB-agoAb202 treated groups exhibited hypertrophy, but no statistical differences among groups were observed on the cellular diameter. ***p<0.001. Data are presented as mean±SEM and analyzed with one-way ANOVA.

5.2 Glaucoma Animal Model

Figure 11:
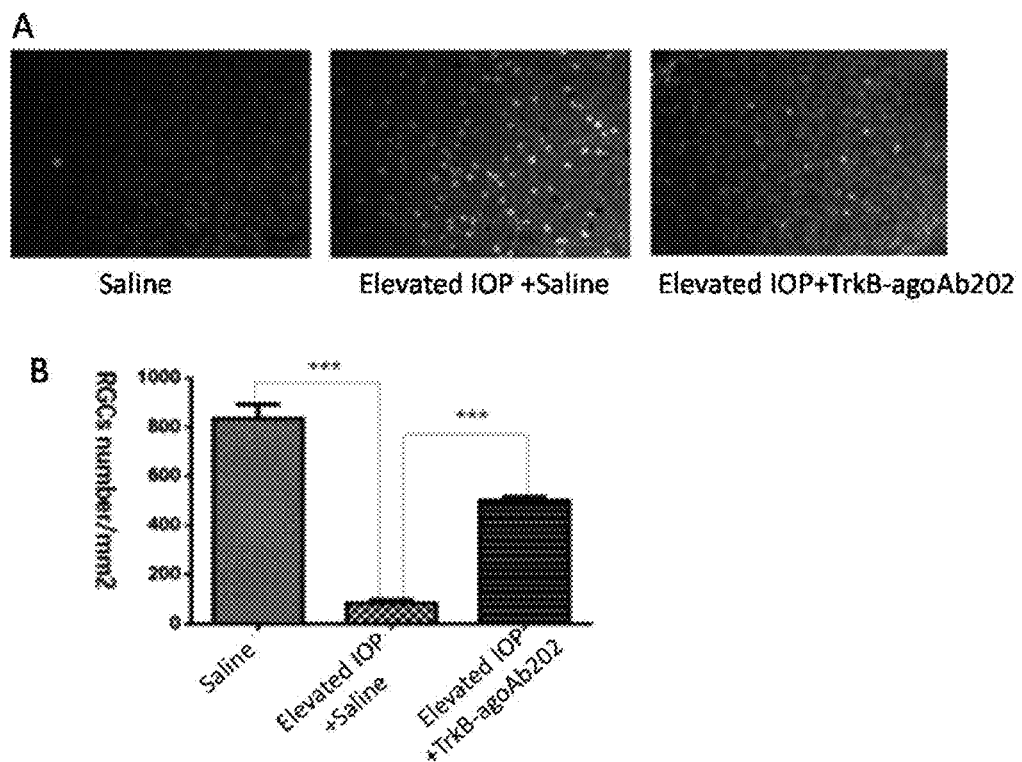
FIGS. 11A and 11B show survival of RGC treated with TrkB-agoAb202 in mice Glaucoma model.

Elevated Intraocular pressure (TOP) induced by intraocular injections of paramagnetic beads was used to establish glaucoma animal model. Before injections, RGCs was labeled by fluorescent marker. 4% Fluorogold solution was selected for retrograde labeling by bilateral brain stereotactic injection in superior colliculus. A 30-gauge needle was used to conduct intraocular injection of paramagnetic beads. The paramagnetic beads was guided to the anterior angle by magnet. The eye on the other side was injected with 20 µl saline to make negative control. After intraocular injection, animals were rested in homecage, and IOP will be tested every other day. After two weeks of intraocular injection of microbeads, both eyes will be intraocular injected with 1 µl saline or TrkB-agoAb202 (1 µg). All mouse will be sacrificed 1 month later, and retina floating tablets will be made. Based on the fluorescence signaling exerted by retrograded labeling (see FIG. 11A), RGCs number were counted. TrkB-agoAb202 showed a significant enhance on RGCs survival (see FIG. 11B). ***p<0.001. Data are presented as mean±SEM and analyzed with one-way ANOVA.

5.3 Stroke

Sprague Dawley rats (~200 g) were subjected to 2 hours of right middle cerebral artery occlusion followed by reperfusion (FR) and administered with PBS (sham operation), 1 mg/kg body weight normal rabbit IgG, 1 mg/kg TrkB-agoAb202 and 0.2 mg/kg TrkB-agoAb202, respectively. Animals were tested for sensory and motor functions for 14 days and euthanized for infarct volume measurement. An additional set of animals were euthanized at day 3 for Western blot assays.

To measure the infarct volume, triphenyl tetrazolium chloride (TTC) was used to stain the brain slices. In normal tissues, TTC turns red in the presence of dehydrogenase in the respiratory chain while it remains white in dead tissues. At day 14 after ischemia, 1 mg/kg TrkB-agoAb202 significantly reduced the infarct volume as compared with the normal IgG treatment. (*P<0.05. n≥7 in each group. Data are presented as mean±SEM and analyzed with one-way ANOVA.) 0.2 mg/kg TrkB-agoAb202 also reduced the infarct volume although not statistically significant (see FIGS. 12A and 12B).

We then evaluated the behavioral outcomes after ischemia by the adhesive-removal test. The time to sense and remove the adhesive inversely indicates the status of sensorimotor function regulated by the according hemisphere of the brain. In the first 5 days after surgery, animals subjected to ischemia/reperfusion all showed impairment in the sensorimotor functions of the left forelimb comparing to the sham. However, compared with the normal IgG treatment, 1 mg/kg TrkB-agoAb202 treatment accelerated the improvement of the sensory function on day 3 and day 5 while shortened time-to-remove on day 5, which indicates better improvement in motor function. This indicates TrkB-agoAb202 facilitated functional recovery after stroke (see FIGS. 13A and 13B). *P<0.05, **P<0.01. n≥9 in each group. Data are presented as mean±SEM and analyzed with two-way ANOVA.

Figure 14:
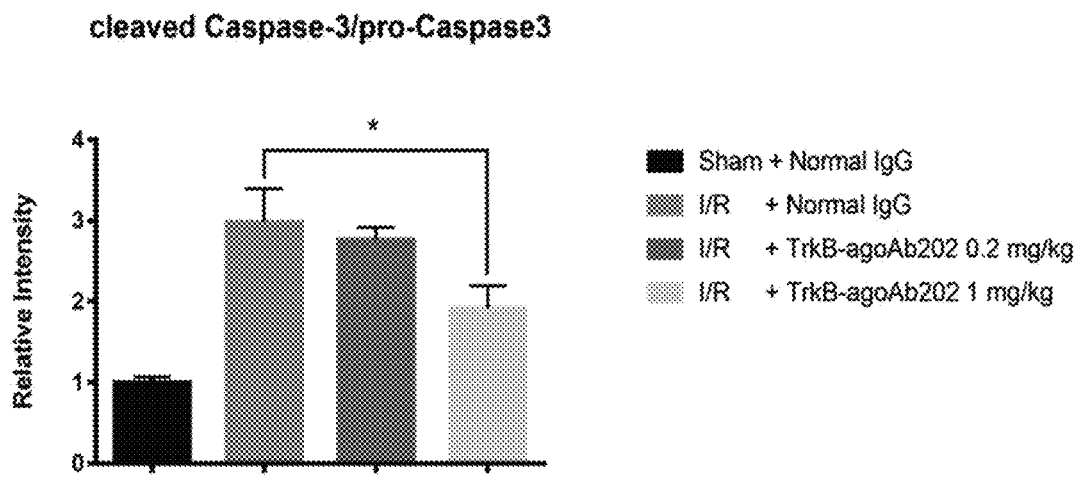
FIG. 14 presents apoptosis suppressed by TrkB-agoAb202 as measured by relative intensity of cleaved caspase-3/pro-caspase 3.

To analyze the possible mechanism of TrkB-agoAb202 action, we sought to discover whether TrkB-agoAb202 affects the apoptotic pathway. Caspase-3 is the executor of apoptosis and is often used as a marker of this type of cell death. Upon activation, the 32 kDa pro-Caspase-3 is cleaved and thus brings out the activated 17 kDa form. Comparing the semi-quantitative result from Western blot, it is indicated that TrkB-agoAb202 reduces cell death partly via the apoptotic pathway (see FIG. 14). *p<0.05, n≥5 in each group. Data are presented as mean±SEM and analyzed with one-way ANOVA.

Figure 15:
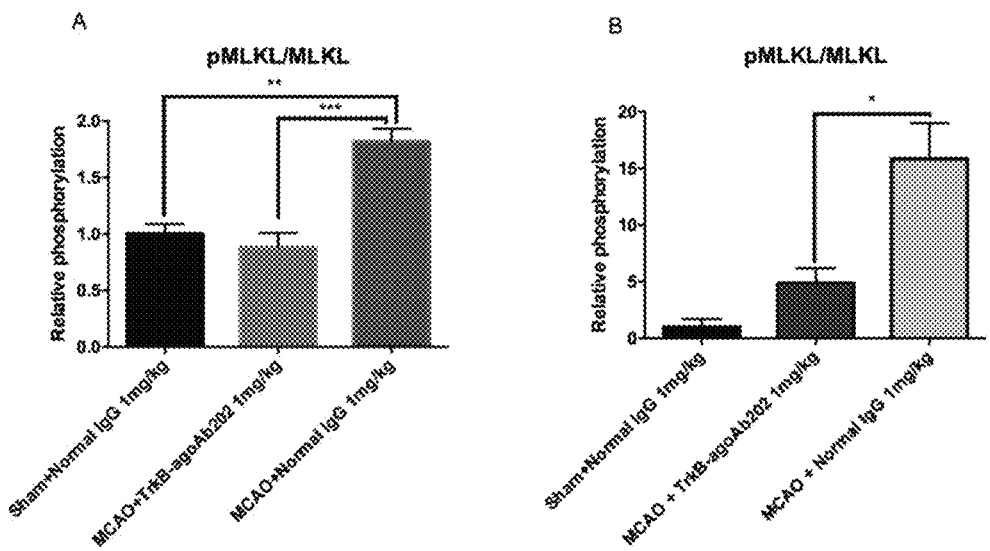
FIGS. 15A and 15B show that TrkB-agoAb administration confers reduced MLKL phosphorylation.

Mixed lineage kinase domain-like (MLKL) is a component of the necrosome whose activation is dependent on the phosphorylation of MLKL. In the cortical tissues experienced either ischemia/reperfusion or permanent ischemia, MLKL phosphorylation was significantly reduced by TrkB-agoAb202 treatment (see FIGS. 15A and 15B). This indicates that activating the TrkB signaling pathway by TrkB-agoAb suppresses the necrosis/necroptosis pathway.

5.4 Pharmacokinetics of TrkB-agoAbs in Plasma and Brain Tissue

Figure 18:
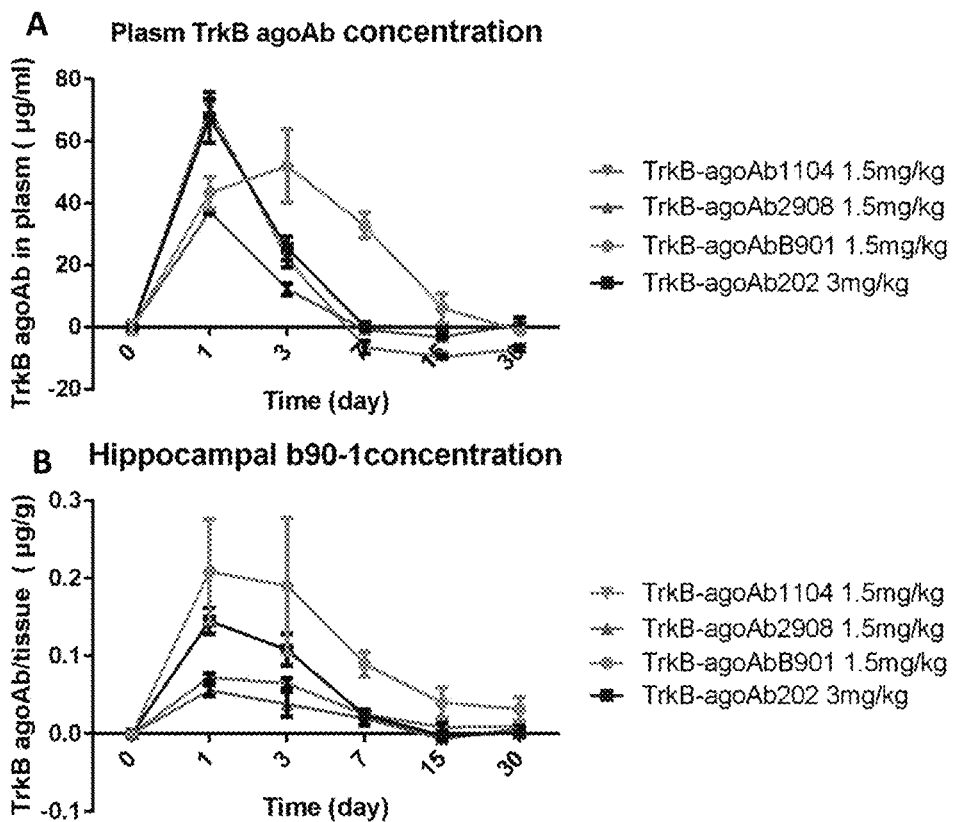
FIGS. 18A and 18B show the pharmacokinetics of TrkB-agoAbs in plasma and brain tissue. The concentrations of the TrkB-agoAbs measured at different time points in the plasm (FIG. 18A) and brain tissue (FIG. 18B) were shown.

To determine the pharmacokinetics of TrkB-agoAbs (TrkB-agoAb1104, TrkB-agoAb2908, TrkB-agoAbB901, and TrkB-agoAb202) in plasma and brain tissue, C57BL/6 mice were dosed by injection through tail vein. 3 mice per group was sacrificed in different time points (1st day, 3rd day, 7th day, 15th day and 30th day) to collect blood samples and brain tissues. Plasma was prepared from the blood samples immediately. Before collecting brain tissues, the mice was perfused by at least 20 ml PBS. Plasma samples and brain tissues were quickly freezed by liquid nitrogen and stored at −80 degree refrigerator. After collecting all samples of different time points, ELISA method was used to detect the antibody concentration of each sample. The baseline (0) of concentration was determined by the control mice (no injection). According to FIG. 18, TrkB-agoAbs are cleared from blood after 7-30 days (see FIG. 18A) and brain after more than 15 days (see FIG. 18B). There is about 0.1-0.5% of the concentration of blood TrkB-agoAb penetrated into brain tissues through brain blood barrier (BBB), and the concentration in the brain is an effective concentration to activate TrkB phosphorylation and downstream kinase signaling pathways, and promote neural survival. For example, when the blood TrkB-agoAb concentration is 3 mg/kg, the concentration penetrated into the brain tissue is 0.1-0.2 µg/g or higher (corresponding to about 1 nM), while in vitro concentration of TrkB-agoAb at 0.3-1 nM is sufficiently effective (see FIGS. 6 and 8).

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. An isolated tropomyosin receptor kinase B (TrkB) agonist antibody or an antigen-binding fragment thereof that specifically binds to an epitope in the D5 domain of TrkB having the sequence of SEQ ID NO: 6 and is capable of activating TrkB, comprising a heavy chain variable region (VH) comprising three heavy chain complementary determining regions (HCDR1, HCDR2 and HCDR3) and a light chain variable region (VL) comprising three light chain complementary determining regions (LCDR1, LCDR2 and LCDR3), wherein the HCDRs1-3 comprise the amino acid sequences of SEQ ID NOs: 48-50 respectively and the LCDRs1-3 comprise the amino acid sequences of SEQ ID NOs: 45-47 respectively.

2. The antibody or the antigen-binding fragment thereof of claim 1, wherein the VH comprises the amino acid sequence of SEQ ID NO: 52 and the VL comprises the amino acid sequence of SEQ ID NO: 51.

3. The antibody or the antigen-binding fragment thereof according to claim 2, wherein the antibody is humanized.

4. The antibody or the antigen-binding fragment thereof of claim 1, wherein the antigen binding fragment is selected from the group consisting of a diabody, a scFv, an scFv dimer, a dsFv, a (dsFv)2, a dsFv-dsFv', an Fv fragment, a Fab, a Fab', a F(ab')2, a ds diabody and a bivalent domain antibody.

5. A pharmaceutical composition comprising a therapeutically effective amount of the antibody or the antigen-binding fragment thereof of claim 1 and a pharmaceutical carrier.

6. The pharmaceutical composition of claim 5, further comprises a second therapeutic agent comprising brain-derived neurotrophic factor (BDNF) and/or neurotrophin-4 (NT-4).

7. A kit comprising the antibody or the antigen-binding fragment thereof of claim 1.

8. A kit comprising the antibody or the antigen-binding fragment thereof of claim 1 for detecting the presence or the level of TrkB in a biological sample, wherein the biological sample is a cell or a tissue.

9. An antibody-conjugate comprising the antibody or the antigen-binding fragment thereof of claim 1, wherein the antibody or the antigen-binding fragment thereof is linked to one or more conjugate moieties, wherein the conjugate moiety is selected from the group consisting of a detectable label, a pharmacokinetic modifying moiety to increase half-life of the antibody and a purification moiety.

10. The antibody-conjugate according to claim 9, wherein the detectable label is selected from the group consisting of biotin, a fluorescent label, a radioactive label and an enzymatic label.

11. The antibody-conjugate according to claim 9, wherein the pharmacokinetic modifying moiety is selected from the group consisting of polyethylene glycol (PEG), carboxymethylcellulose, dextran, polyvinyl alcohol, polyvinyl pyrrolidone and copolymers of ethylene glycol/propylene glycol.

12. The antibody-conjugate according to claim 9, wherein the purification moiety is a magnetic bead.

13. A method for enhancing cell survival, enhancing neural injury repairing, protecting neural cells from apoptosis and/or necroptosis in neural cells expressing TrkB or promoting sensorimotor function in a TrkB associated condition in a subject in need thereof, comprising administering to the subject the antibody or the antigen-binding fragment thereof of claim 1, thereby enhancing cell survival, enhancing neural injury repairing, protecting neural cells from apoptosis and/or necroptosis in neural cells expressing TrkB or promoting sensorimotor function in the subject having the TrkB associated condition, wherein the TrkB associated condition is selected from the group consisting of stroke and a motoneuron injury.

14. A method of enhancing neuronal differentiation, enhancing synaptic development, enhancing neurite branching, enhancing cell survival or protecting cells from apoptosis and/or necroptosis in a biological sample comprising neural cells expressing TrkB, comprising contacting the biological sample with the antibody or the antigen-binding fragment thereof of claim 1, wherein the neural cells are selected from the group consisting of PC12 cells, hippocampal neurons, motor neurons and retinal ganglion cells (RGCs).

15. A method for enhancing survival of retinal ganglion cells (RGCs) in glaucoma in a subject in need thereof, comprising administering to the subject a composition comprising the antibody or the antigen-binding fragment thereof of claim 1, thereby enhancing RGCs survival.

* * * * *